(12) United States Patent
Liu et al.

(10) Patent No.: US 7,867,494 B2
(45) Date of Patent: Jan. 11, 2011

(54) ANTI-IGE ANTIBODIES

(75) Inventors: Wai Liu, Sandwich (GB); Mike Yeadon, Sandwich (GB); Isabelle de Mendez, Cambridge (GB); Alison Logan, Old Saybrook, CT (US); Gerald F. Casperson, Ballwin, MO (US); Arvind Rajpal, Chesterfield, MO (US); Mark A. Moffat, Saint Louis, MO (US); Wei Liao, Chesterfield, MO (US); Caroline Brown, Sandwich (GB); Nurten Beyaz-Kavuncu, Chesterfield, MO (US); Judith Diaz-Collier, Manchester (GB); Sirid-Aimee Kellermann, Menlo Park, CA (US)

(73) Assignees: Amgen Fremont Inc., Fremont, CA (US); Pfizer Inc., New York, NY (US)

( * ) Notice: Subject to any disclaimer, the term of this patent is extended or adjusted under 35 U.S.C. 154(b) by 164 days.

(21) Appl. No.: 12/080,419

(22) Filed: Apr. 1, 2008

(65) Prior Publication Data

US 2009/0117124 A1 May 7, 2009

Related U.S. Application Data

(60) Provisional application No. 60/921,546, filed on Apr. 2, 2007, provisional application No. 61/008,755, filed on Dec. 20, 2007.

(51) Int. Cl.
*A61K 39/395* (2006.01)
(52) U.S. Cl. .............. 424/133.1; 424/141.1; 424/141.2; 424/152.1; 424/805
(58) Field of Classification Search ........................ None
See application file for complete search history.

(56) References Cited

U.S. PATENT DOCUMENTS

| | | | |
|---|---|---|---|
| 5,223,409 A | 6/1993 | Ladner et al. | |
| 5,543,144 A | 8/1996 | Chang | |
| 5,916,771 A | 6/1999 | Hori et al. | |
| 5,939,598 A | 8/1999 | Kucherlapati et al. | |
| 5,958,708 A * | 9/1999 | Hardman et al. ............ | 435/7.21 |
| 5,985,615 A | 11/1999 | Jakobovits et al. | |
| 5,994,619 A | 11/1999 | Stice et al. | |
| 5,998,209 A | 12/1999 | Jokobovits et al. | |
| 6,075,181 A | 6/2000 | Kucherlapati et al. | |
| 6,091,001 A | 7/2000 | Jakobovits et al. | |
| 6,114,598 A | 9/2000 | Kucherlapati et al. | |
| 6,130,364 A | 10/2000 | Jakobovits et al. | |
| 6,150,584 A | 11/2000 | Kucherlapati et al. | |
| 6,162,963 A | 12/2000 | Kucherlapati et al. | |
| 6,172,213 B1 * | 1/2001 | Lowman et al. .......... | 536/23.53 |
| 6,685,939 B2 | 2/2004 | Jardieu et al. | |
| 2005/0169909 A1 * | 8/2005 | Singh et al. .............. | 424/130.1 |

FOREIGN PATENT DOCUMENTS

| | | |
|---|---|---|
| WO | WO91/10741 | 7/1991 |
| WO | WO91/17271 | 11/1991 |
| WO | WO92/01047 | 6/1992 |
| WO | WO92/09690 | 6/1992 |
| WO | WO92/15679 | 9/1992 |
| WO | WO92/18619 | 10/1992 |
| WO | WO 9217207 A1 * | 10/1992 |
| WO | WO92/20791 | 11/1992 |
| WO | WO93/01288 | 1/1993 |
| WO | WO93/06213 | 4/1993 |
| WO | WO94/02602 | 2/1994 |
| WO | WO96/33735 | 10/1996 |
| WO | WO96/34096 | 10/1996 |
| WO | WO98/16654 | 4/1998 |
| WO | WO98/24893 | 6/1998 |
| WO | WO98/50433 | 11/1998 |
| WO | WO98/52976 | 11/1998 |
| WO | WO99/45031 | 9/1999 |
| WO | WO99/53049 | 10/1999 |
| WO | WO00/09560 | 2/2000 |
| WO | WO00/34317 | 6/2000 |
| WO | WO00/37504 | 6/2000 |
| WO | WO03/048731 | 6/2003 |

OTHER PUBLICATIONS

Portolano et al., J Immunol. Feb. 1, 1993;150(3):880-7.*
Rudikoff et al., Proc Natl Acad Sci U S A. Mar. 1982;79(6):1979-83.*
Janeway et al., Immunobiology, $3^{rd}$ edition, 1997, Garland Press, pp. 3:7-3:11.*
William E. Paul, M.D., editor, Fundamental Immunology, 3d ed. Raven Press, 1993, p. 242.*
Babcook et al., A novel strategy for generating monoclonal antibodies from single, isolated lymphocytes producing antibodies of defined specificities, Proc. Natl. Acad. Sci. USA 93:7843-7348 (1996).
Barbas et al., Assembly of combinatorial antibody libraries on phage surfaces: The gene III site, Proc. Natl. Acad. Sci. USA 88:7978-7982 (1991).
Bird et al., Single-chain antigen-binding proteins, Science 242:423-426 (1988).
Dibbern et al., RBL cells expressing human Fc epsilon RI are a sensitive tool for exploring functional IgE-allergen interactions: studies with sera from peanut-sensitive patients, J. Immunol Methods. 274(1-2):37-45 (2003).
Fuchs et al., Targeting recombinant antibodies to the surface of *Escherichia coli*: fusion to a peptidoglycan associated lipoprotein, Bio/Technology 9:1370-1372 (1991).
Garrad et al., Fab assembly and enrichment in a monovalent phage display system, Bio/Technology 9:1373-1377 (1991).

(Continued)

*Primary Examiner*—Michael Szperka
(74) *Attorney, Agent, or Firm*—Ropes & Gray LLP

(57) ABSTRACT

The present invention relates to novel human antibodies specifically directed against human immunoglobulin E (anti-IgE). The present invention also relates to pharmaceutical compositions and methods for treating asthma, in particular allergic asthma, as well as other IgE-mediated disorders including allergic rhinitis and food allergies.

14 Claims, 5 Drawing Sheets

OTHER PUBLICATIONS

Gram et al., In vitro selection and affinity maturation of antibodies from a naive combinatorial immunoglobulin library, Proc. Natl. Acad. Sci. USA 89:3576-3580 (1992).

Green and Jakobovits, Regulation of B cell development by variable gene complexity in mice reconstituted with human immunoglobulin yeast artificial chromosomes, J. Exp. Med. 188:483-495 (1998).

Green et al., Antigen-specific human monoclonal antibodies from mice engineered with human Ig heavy and light chain YACs, Nature Genetics 7:13-21 (1994).

Griffiths et al., Human anti-self antibodies with high specificity from phage display libraries, EMBO J. 12:725-734 (1993).

Hawkins et al., Selection of phage antibodies by binding affinity. Mimicking affinity maturation, J. Mol. Biol. 226:889-896 (1992).

Hay et al., Bacteriophage cloning and Escherichia coli expression of a human IgM Fab, Hum. Antibod. Hybridomas 3:81-85 (1992).

Holliger et al., "Diabodies": small bivalent and bispecific antibody fragments, Proc. Natl. Acad. Sci. USA 90:6444-6448 (1993).

Hoogenboom et al., Multi-subunit proteins on the surface of filamentous phage: methodologies for displaying antibody (Fab) heavy and light chains, Nuc. Acid Res. 19:4133-4137 (1991).

Huse et al., Generation of a large combinatorial library of the immunoglobulin repertoire in phage lambda, Science 246:1275-1281 (1989).

Huston et al., Protein engineering of antibody binding sites: recovery of specific activity in an anti-digoxin single-chain Fv analogue produced in Escherichia coli, Proc. Natl. Acad. Sci. USA 85:5879-5883 (1988).

McCafferty et al., Phage antibodies: filamentous phage displaying antibody variable domains, Nature 348:552-554 (1990).

Mendez et al., Functional transplant of megabase human immunoglobulin loci recapitulates human antibody response in mice, Nature Genetics 15:146-156 (1997).

Poljak et al., Production and structure of diabodies, Structure 2:1121-1123 (1994).

Presta et al., Humanization of an antibody directed against IgE, J. Immunol. 151(5):2623-2632 (1993).

Tabcharani et al., Phosphorylation-regulated Cl- channel in CHO cells stably expressing the cystic fibrosis gene, Nature 352:624-628 (1991).

Wiegand et al., High-affinity oligonucleotide ligands to human IgE inhibit binding to Fc epsilon receptor I, J. Immunol. 157(1):221-230 (1996).

* cited by examiner

Figure 1: Agonist activity of anti-IgE antibodies of the invention in RBL-2H3 (FcεR1) cell assay.
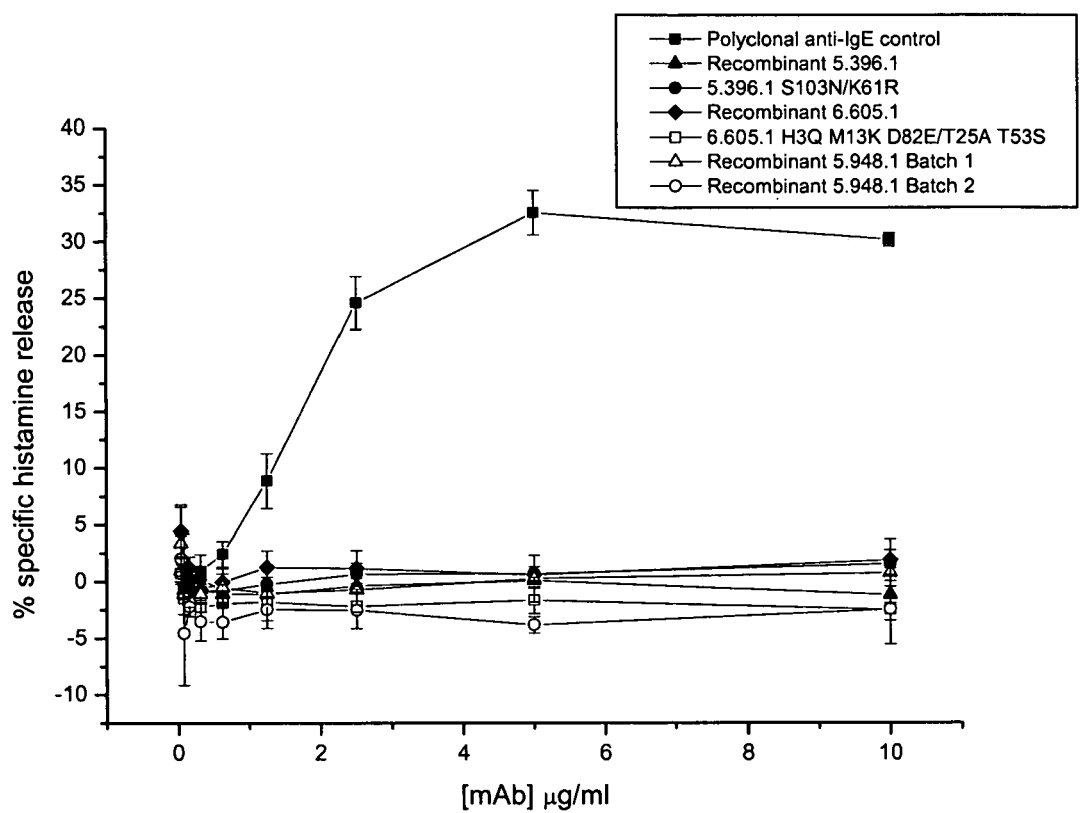

Figure 2: Agonist activity of anti-IgE antibodies of the invention in RBL-2H3 (FcεR1) cell assay.
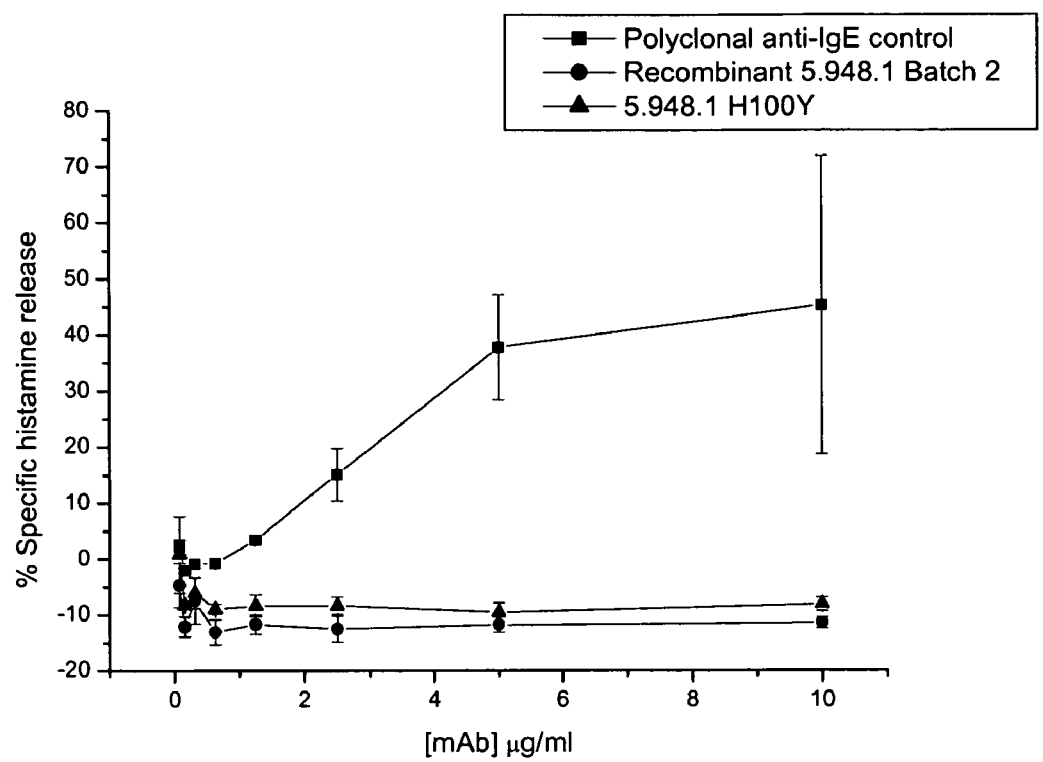

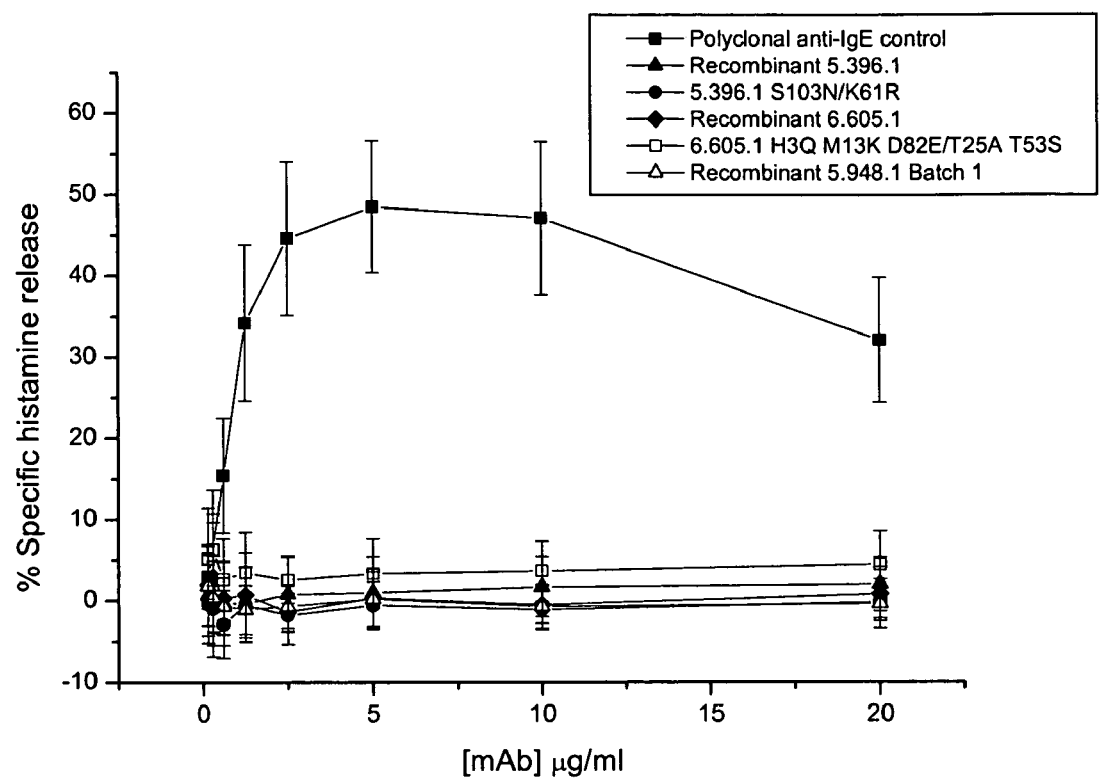
Figure 3: Agonist activity of anti-IgE antibodies of the invention in human blood basophil assay. Data are mean +/- SEM of 4 donors.

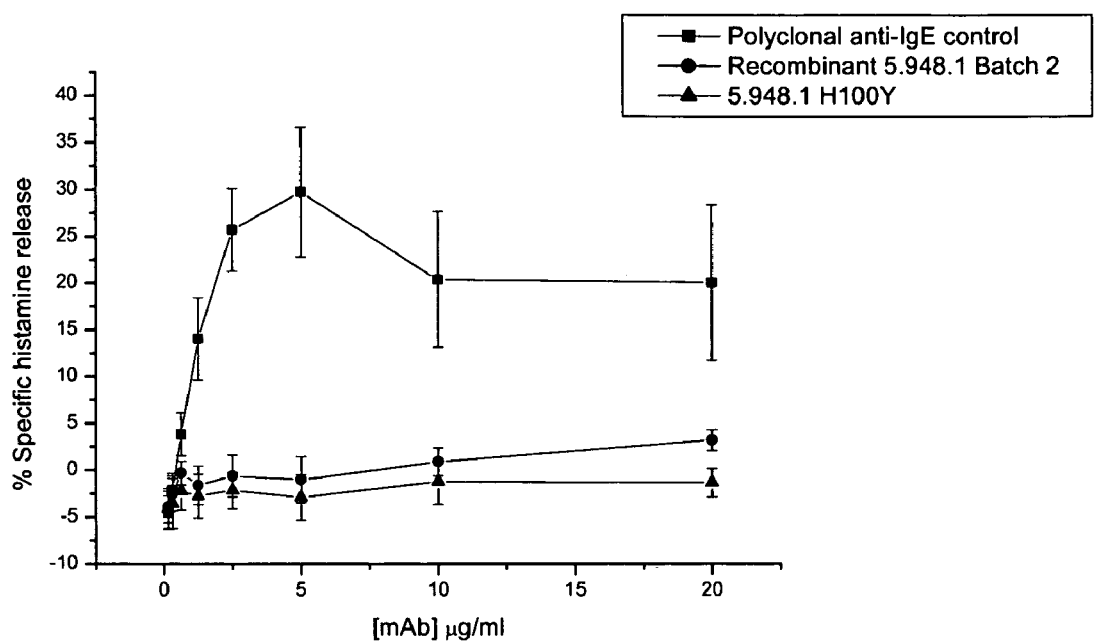
Figure 4: Agonist activity of anti-IgE antibodies of the invention in human blood basophil assay. Data are mean +/- SEM of 4 donors.

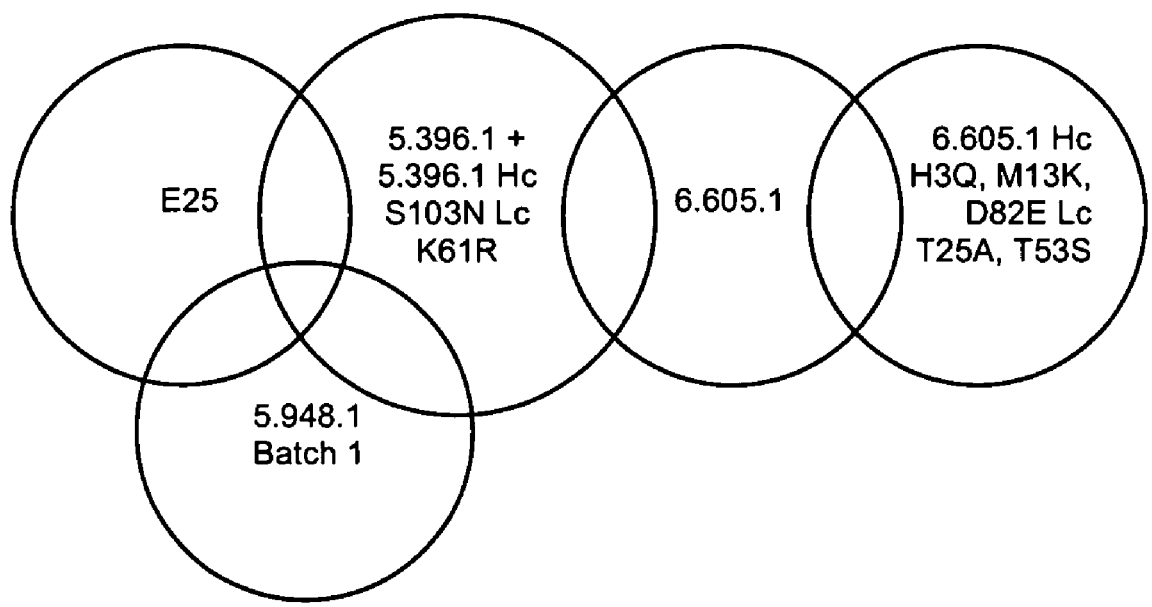
Figure 5: Epitope binning map

SEQUENCE LISTING

<160> NUMBER OF SEQ ID NOS: 174

<210> SEQ ID NO 1
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg gcctggagtg gattggggaa atccatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcgag agacaactgg     300
aacgactctt tctactacta ctacggtatg gacgtctggg gccaagggac cacggtcacc     360
gtctcctcag cctccaccaa gggcccatcg gtcttccccc tggcgccctg ctccaggagc     420
acctccgaga gcacagcggc cctgggctgc ctggtcaagg actacttccc cgaaccggtg     480
acggtgtcgt ggaactcagg cgctctgacc agcggcgtgc acaccttccc ggctgtccta     540
cagtcctcag gactctactc cctcagcagc gtagtgaccg tgccctccag caacttcggc     600
acccagacct acacctgcaa cgtagatcac aagcccagca acaccaaggt ggacaagaca     660
gttgagcgca aatgttgtgt cgagtgccca ccgtgcccag caccacctgt ggcaggaccg     720
tcagtcttcc tcttcccccc aaaacccaag gacaccctca tgatctcccg gacccctgag     780
gtcacgtgcg tggtggtgga cgtgagccac gaagacccca ggtccagtt caactggtac     840
```

```
gtggacggcg tggaggtgca taatgccaag acaaagccac gggaggagca gttcaacagc    900
acgttccgtg tggtcagcgt cctcaccgtc gtgcaccagg actggctgaa cggcaaggag    960
tacaagtgca aggtctccaa caaaggcctc ccagccccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctacccag cgacatcgcc    1140 gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacacag   1320
aagagcctct ccctgtctcc gggtaaa                                       1347
```

<210> SEQ ID NO 2
<211> LENGTH: 449
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 2

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asn Trp Asn Asp Ser Phe Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
        290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 3
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atccatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcgag agacaactgg     300
aacgactctt tctactacta ctacggtatg gacgtctggg gccaagggac cacggtcacc     360
gtctcctca                                                             369

<210> SEQ ID NO 4
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
```

```
                35                  40                  45
Gly Glu Ile His His Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Asn Trp Asn Asp Ser Phe Tyr Tyr Tyr Gly Met Asp Val
             100                 105                 110

Trp Gly Gln Gly Thr Thr Val Thr Val Ser Ser
        115                 120

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggttactact ggagc                                                      15

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Tyr Trp Ser
1               5

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaaatccatc atagtggaag caccaactac aacccgtccc tcaagagt                  48

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Ile His His Ser Gly Ser Thr Asn Tyr Asn Pro Ser Leu Lys Ser
1               5                   10                  15

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 9
gacaactgga acgactcttt ctactactac tacggtatgg acgtc   45

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Asn Trp Asn Asp Ser Phe Tyr Tyr Tyr Tyr Gly Met Asp Val
1               5                   10                  15

<210> SEQ ID NO 11
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gacatccaga tgacccagtc tccatcatca ctgtctgcat ctgtaggaga cagagtcacc   60
atcacatgtc gggcgagtca gggcattagc aatcatttag cctggtttca gcagaaacca  120
gggaaagccc ctaagtccct gatctatgct gcatccagtt tgcaaagtgg ggtcccatca  180
aagttcagcg gcagtggatc tgggacagat ttcactctca ccatcagcag cctgcagcct  240
gaagattttg caacttatta ctgccaacag tataataggc acccattcac tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga aaacacaaa gtctacgcct gcgaagtcac ccatcagggc  600
ctgagctcgc ccgtcacaaa gagcttcaac aggggagagt gt                    642

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn His
                20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Lys Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Arg His Pro Phe

```
                85                  90                  95
Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 13
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gacatccaga tgacccagtc tccatcatca ctgtctgcat ctgtaggaga cagagtcacc    60
atcacatgtc gggcgagtca gggcattagc aatcatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataataggc acccattcac tttcggccct   300
gggaccaaag tggatatcaa a                                             321

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn His
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Arg His Pro Phe
                85                  90                  95

Thr Phe Gly Pro Gly Thr Lys Val Asp Ile Lys
            100                 105
```

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgggcgagtc agggcattag caatcattta gcc                               33

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ala Ser Gln Gly Ile Ser Asn His Leu Ala
1               5                   10

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gctgcatcca gtttgcaaag t                                            21

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Ser Ser Leu Gln Ser
1               5

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caacagtata ataggcaccc attcact                                      27

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Tyr Asn Arg His Pro Phe Thr
1               5

<210> SEQ ID NO 21
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg gctggagtg gattgggaa atccatcata gtggaagcac caactacaac      180
ccgtccctca agagtcgagt caccatatca gtagacacgt ccaagaacca gttctccctg     240
aagctgagct ctgtgaccgc cgcggacacg gctgtgtatt actgtgcgag agacaactgg     300
aacgacaact tctactacta ctacggtatg gacgtctggg gccaagggac cacggtcacc     360
gtctcctcag cctccaccaa gggcccatcg gtcttccccc tggcgccctg ctccaggagc     420
acctccgaga gcacagcggc cctgggctgc ctggtcaagg actacttccc cgaaccggtg     480
acggtgtcgt ggaactcagg cgctctgacc agcggcgtgc acaccttccc ggctgtccta     540
cagtcctcag gactctactc cctcagcagc gtagtgaccg tgccctccag caacttcggc     600
acccagacct acacctgcaa cgtagatcac aagcccagca acaccaaggt ggacaagaca     660
gttgagcgca aatgttgtgt cgagtgccca ccgtgcccag caccacctgt ggcaggaccg     720
tcagtcttcc tcttcccccc aaaacccaag gacaccctca tgatctcccg gacccctgag     780
gtcacgtgcg tggtggtgga cgtgagccac gaagacccccg aggtccagtt caactggtac     840
gtggacggcg tggaggtgca taatgccaag acaaagccac gggaggagca gttcaacagc     900
acgttccgtg tggtcagcgt cctcaccgtc gtgcaccagg actggctgaa cggcaaggag     960
tacaagtgca aggtctccaa caaaggcctc ccagccccca tcgagaaaac catctccaaa    1020
accaaagggc agccccgaga accacaggtg tacaccctgc ccccatcccg ggaggagatg    1080
accaagaacc aggtcagcct gacctgcctg gtcaaaggct tctacccag cgacatcgcc    1140
gtggagtggg agagcaatgg gcagccggag aacaactaca agaccacacc tcccatgctg    1200
gactccgacg gctccttctt cctctacagc aagctcaccg tggacaagag caggtggcag    1260
caggggaacg tcttctcatg ctccgtgatg catgaggctc tgcacaacca ctacacacag    1320
aagagcctct ccctgtctcc gggtaaa                                        1347
```

<210> SEQ ID NO 22
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile

-continued

```
                35                  40                  45
Gly Glu Ile His His Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Asn Trp Asn Asp Asn Phe Tyr Tyr Tyr Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
            210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Phe Arg Val
            290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 23
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atccatcata gtggaagcac caactacaac     180
ccgtccctca gagtcgagt caccatatca gtagacacgt ccaagaacca gttctccctg     240
aagctgagct ctgtgaccgc cgcggacacg gctgtgtatt actgtgcgag agacaactgg     300
aacgacaact tctactacta ctacggtatg gacgtctggg gccaagggac cacggtcacc     360
gtctcctca                                                             369

<210> SEQ ID NO 24
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asn Trp Asn Asp Asn Phe Tyr Tyr Tyr Gly Met Asp Val
            100                 105                 110

Trp Gly Gln Gly Thr Thr Val Thr Val Ser Ser
        115                 120

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggttactact ggagc                                                       15

<210> SEQ ID NO 26
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 26

Gly Tyr Tyr Trp Ser
1               5

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaaatccatc atagtggaag caccaactac aacccgtccc tcaagagt                48

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Ile His His Ser Gly Ser Thr Asn Tyr Asn Pro Ser Leu Lys Ser
1               5                   10                  15

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gacaactgga acgacaactt ctactactac tacggtatgg acgtc               45

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Asn Trp Asn Asp Asn Phe Tyr Tyr Tyr Tyr Gly Met Asp Val
1               5                   10                  15

<210> SEQ ID NO 31
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacatccaga tgacccagtc tccatcatca ctgtctgcat ctgtaggaga cagagtcacc     60
atcacatgtc gggcgagtca gggcattagc aatcatttag cctggtttca gcagaaacca    120
gggaaagccc ctaagtccct gatctatgct gcatccagtt tgcaaagtgg ggtcccatca    180

```
aggttcagcg gcagtggatc tgggacagat tcactctca ccatcagcag cctgcagcct    240
gaagattttg caacttatta ctgccaacag tataataggc acccattcac tttcggccct    300
gggaccaaag tggatatcaa acgaactgtg ctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn His
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Arg His Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 33

```
gacatccaga tgacccagtc tccatcatca ctgtctgcat ctgtaggaga cagagtcacc    60
atcacatgtc gggcgagtca gggcattagc aatcatttag cctggtttca gcagaaacca   120
gggaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataataggc acccattcac tttcggccct   300
gggaccaaag tggatatcaa a                                              321
```

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn His
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Arg His Pro Phe
                85                  90                  95

Thr Phe Gly Pro Gly Thr Lys Val Asp Ile Lys
            100                 105
```

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 35

```
cgggcgagtc agggcattag caatcattta gcc                                  33
```

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 36

```
Arg Ala Ser Gln Gly Ile Ser Asn His Leu Ala
1               5                   10
```

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
gctgcatcca gtttgcaaag t                                              21

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ala Ser Ser Leu Gln Ser
1               5

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
caacagtata ataggcaccc attcact                                        27

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Tyr Asn Arg His Pro Phe Thr
1               5

<210> SEQ ID NO 41
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggttcacc tggtgcagtc tggagctgag gtgaagatgc ctggggcctc agtgaaggtc      60
tcctgcaagg cttctggtta caccttacc agctatggta tcagctgggt gcgacaggcc     120
cctggacaag ggcttgagtg gatgggatgg atcagcgctt acaatggtaa cacaaactat     180
gcacagaagc tccagggcag aatcaccatg accacagaca tccacgag cacagcctac      240 atggacctga ggagcctgag atctgacgac acggccgtgt attactgtgc gagagatggg     300
gattactatg atccttttga ctactggggc cagggaaccc tggtcaccgt ctcctcagcc     360
tccaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttcccgg ctgtcctaca gtcctcagga     540
ctctactccc tcagcagcgt agtgaccgtg ccctccagca acttcggcac ccagacctac     600
acctgcaacg tagatcacaa gcccagcaac accaaggtgg acaagacagt tgagcgcaaa     660

```
tgttgtgtcg agtgcccacc gtgcccagca ccacctgtgg caggaccgtc agtcttcctc    720 ttcccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgtcgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacacagaa gagcctctcc   1320
ctgtctccgg gtaaa                                                    1335
```

<210> SEQ ID NO 42
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Gln Val His Leu Val Gln Ser Gly Ala Glu Val Lys Met Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Ile Thr Met Thr Thr Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Asp Gly Asp Tyr Tyr Asp Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
```

```
                225                 230                 235                 240
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 43
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
caggttcacc tggtgcagtc tggagctgag gtgaagatgc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatggtaa cacaaactat     180
gcacagaagc tccagggcag aatcaccatg accacagaca catccacgag cacagcctac     240
atggacctga ggagcctgag atctgacgac acggccgtgt attactgtgc gagagatggg     300
gattactatg atccttttga ctactggggc cagggaaccc tggtcaccgt ctcctca       357

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val His Leu Val Gln Ser Gly Ala Glu Val Lys Met Pro Gly Ala
1               5                   10                  15

Ser Val Lys Val Ser Cys Lys Ala Ser Gly Tyr Thr Phe Thr Ser Tyr
```

```
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Ile Thr Met Thr Thr Asp Thr Ser Thr Ser Thr Ala Tyr
65                  70                  75                  80
Met Asp Leu Arg Ser Leu Arg Ser Asp Thr Ala Val Tyr Tyr Cys
                85                  90                  95
Ala Arg Asp Gly Asp Tyr Tyr Asp Pro Phe Asp Tyr Trp Gly Gln Gly
            100                 105                 110
Thr Leu Val Thr Val Ser Ser
        115
```

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agctatggta tcagc                                                      15

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ser Tyr Gly Ile Ser
1               5
```

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tggatcagcg cttacaatgg taacacaaac tatgcacaga agctccaggg c              51

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Trp Ile Ser Ala Tyr Asn Gly Asn Thr Asn Tyr Ala Gln Lys Leu Gln
1               5                   10                  15

Gly
```

<210> SEQ ID NO 49
<211> LENGTH: 30

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 gatgggatt actatgatcc ttttgactac                                    30

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Gly Asp Tyr Tyr Asp Pro Phe Asp Tyr
1               5                   10

<210> SEQ ID NO 51
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gacatccaga tgacccagtc tccatcctcc ctgtctgcat ctgtaggaga cagagtcacc    60
atcacttgcc ggacaagtca gagtattagc aactggttaa attggtatca gcagaaacca   120
gggaaagccc ctaaactcct gatctatggt gcctccactt tgaaaagtgg ggtcccatca   180
aggttcagtg gcagtgaatc tgggacagat ttcactctca ccatcagcag tctgcaacct   240
gaagattttg caacttacta ctgtcaacag agttacagta cccctccgac gttcggccaa   300
gggaccaagg tggaaatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540 ctgagcaaag cagactacga gaaacacaaa gtctacgcct gcgaagtcac ccatcagggc   600
ctgagctcgc ccgtcacaaa gagcttcaac aggggagagt gt                     642

<210> SEQ ID NO 52
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Gly Ala Ser Thr Leu Lys Ser Gly Val Pro Ser Arg Phe Ser Gly
    50                  55                  60
```

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 53
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gacatccaga tgacccagtc tccatcctcc ctgtctgcat ctgtaggaga cagagtcacc      60
atcacttgcc ggacaagtca gagtattagc aactggttaa attggtatca gcagaaacca     120
gggaaagccc ctaaactcct gatctatggt gcctccactt tgaaaagtgg ggtcccatca     180
aggttcagtg gcagtgaatc tgggacagat ttcactctca ccatcagcag tctgcaacct     240
gaagattttg caacttacta ctgtcaacag agttacagta cccctccgac gttcggccaa     300
gggaccaagg tggaaatcaa a                                               321

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Gly Ala Ser Thr Leu Lys Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Pro Pro
            85                  90                  95
Thr Phe Gly Gln Gly Thr Lys Val Glu Ile Lys
            100                 105

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cggacaagtc agagtattag caactggtta aat                                33

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Thr Ser Gln Ser Ile Ser Asn Trp Leu Asn
1               5                   10

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggtgcctcca ctttgaaaag t                                             21

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ala Ser Thr Leu Lys Ser
1               5

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
caacagagtt acagtacccc tccgacg                                       27

<210> SEQ ID NO 60
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 60

Gln Gln Ser Tyr Ser Thr Pro Pro Thr
1               5

<210> SEQ ID NO 61
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caggtccagc tggtgcagtc tggagctgag gtgaagaagc ctggggcctc agtgaaggtc      60
tcctgcaagg cttctggtta ccctttacc agctatggta tcagctgggt gcgacaggcc     120
cctggacaag gcttgagtg gatgggatgg atcagcgctt acaatggtaa cacaaactat     180
gcacagaagc tccagggcag aatcaccatg accacagaca catccacgag cacagcctac     240
atggaactga ggagcctgag atctgacgac acggccgtgt attactgtgc gagagatggg     300
gattactatg atcctttga ctactgggc agggaaccc tggtcaccgt ctcctcagcc     360
tccaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttcccgg ctgtcctaca gtcctcagga     540
ctctactccc tcagcagcgt agtgaccgtg ccctccagca cttcggcac ccagacctac     600 acctgcaacg tagatcacaa gcccagcaac accaaggtgg acaagacagt tgagcgcaaa     660
tgttgtgtcg agtgcccacc gtgcccagca ccacctgtgg caggaccgtc agtcttcctc     720
ttccccccaa aacccaagga caccctcatg atctcccgga cccctgaggt cacgtgcgtg     780
gtggtggacg tgagccacga agaccccgag gtccagttca actggtacgt ggacggcgtg     840
gaggtgcata atgccaagac aaagccacgg gaggagcagt tcaacagcac gttccgtgtg     900
gtcagcgtcc tcaccgtcgt gcaccaggac tggctgaacg gcaaggagta caagtgcaag     960
gtctccaaca aaggcctccc agcccccatc gagaaaacca tctccaaaac caagggcag    1020 ccccgagaac cacaggtgta caccctgccc ccatcccggg aggagatgac caagaaccag    1080
gtcagcctga cctgcctggt caaaggcttc taccccagcg acatcgccgt ggagtgggag    1140
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacacagaa gagcctctcc    1320
ctgtctccgg gtaaa                                                     1335

<210> SEQ ID NO 62
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
             20                  25                  30
Gly Ile Ser Trp Val Arg Gln Ala Pro Gly Gln Gly Leu Glu Trp Met
         35                  40                  45
Gly Trp Ile Ser Ala Tyr Asn Gly Asn Thr Asn Tyr Ala Gln Lys Leu
     50                  55                  60
Gln Gly Arg Ile Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Asp Gly Asp Tyr Tyr Asp Pro Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Asn Phe Gly Thr Gln Thr Tyr Thr Cys Asn Val Asp His Lys Pro
        195                 200                 205
Ser Asn Thr Lys Val Asp Lys Thr Val Glu Arg Lys Cys Cys Val Glu
    210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Phe Arg Val Val Ser Val Leu
    290                 295                 300
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
        435                 440                 445

<210> SEQ ID NO 63
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
caggtccagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatggtaa cacaaactat      180
gcacagaagc tccagggcag aatcaccatg accacagaca catccacgag cacagcctac     240
atggaactga ggagcctgag atctgacgac acggccgtgt attactgtgc gagagatggg     300
gattactatg atccttttga ctactggggc cagggaaccc tggtcaccgt ctcctca       357

<210> SEQ ID NO 64
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Ile Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Asp Tyr Tyr Asp Pro Phe Asp Tyr Trp Gly Gln Gly
            100                 105                 110

Thr Leu Val Thr Val Ser Ser
        115

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agctatggta tcagc                                                       15

<210> SEQ ID NO 66
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 66

Ser Tyr Gly Ile Ser
1               5

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tggatcagcg cttacaatgg taacacaaac tatgcacaga agctccaggg c           51

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Trp Ile Ser Ala Tyr Asn Gly Asn Thr Asn Tyr Ala Gln Lys Leu Gln
1               5                   10                  15
Gly

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gatggggatt actatgatcc ttttgactac                                   30

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Gly Asp Tyr Tyr Asp Pro Phe Asp Tyr
1               5                   10

<210> SEQ ID NO 71
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gacatccaga tgacccagtc tccatcctcc ctgtctgcat ctgtaggaga cagagtcacc    60
atcacttgcc gggcaagtca gagtattagc aactggttaa attggtatca gcagaaacca   120
```

-continued

```
gggaaagccc ctaaactcct gatctatggt gcctccagtt tgaaaagtgg ggtcccatca      180
aggttcagtg gcagtgaatc tgggacagat ttcactctca ccatcagcag tctgcaacct      240
gaagattttg caacttacta ctgtcaacag agttacagta cccctccgac gttcggccaa      300
gggaccaagg tggaaatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cacccctgacg      540 ctgagcaaag cagactacga gaaacacaaa gtctacgcct gcgaagtcac ccatcagggc      600
ctgagctcgc ccgtcacaaa gagcttcaac aggggagagt gt                         642
```

<210> SEQ ID NO 72
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Gly Ala Ser Ser Leu Lys Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 73
<211> LENGTH: 321
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 73

| gacatccaga tgacccagtc tccatcctcc ctgtctgcat ctgtaggaga cagagtcacc | 60 |
| atcacttgcc gggcaagtca gagtattagc aactggttaa attggtatca gcagaaacca | 120 |
| gggaaagccc ctaaactcct gatctatggt gcctccagtt tgaaaagtgg ggtcccatca | 180 |
| aggttcagtg gcagtgaatc tgggacagat ttcactctca ccatcagcag tctgcaacct | 240 |
| gaagattttg caacttacta ctgtcaacag agttacagta cccctccgac gttcggccaa | 300 |
| gggaccaagg tggaaatcaa a | 321 |

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Gly Ala Ser Ser Leu Lys Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cgggcaagtc agagtattag caactggtta aat                                33

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ala Ser Gln Ser Ile Ser Asn Trp Leu Asn
1               5                   10

<210> SEQ ID NO 77
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 77
ggtgcctcca gtttgaaaag t                                             21

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ala Ser Ser Leu Lys Ser
1               5

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
caacagagtt acagtacccc tccgacg                                       27

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Ser Tyr Ser Thr Pro Pro Thr
1               5

<210> SEQ ID NO 81
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag gcttgagtg gatgggatgg atggacccta acagtggtaa cacaggctat    180
gcacagaagt tccagggcag agtcaccatg accaggaaca cctccataag cacagcctac   240
atggagctga gcagcctgag atctgaggac acggccgtgt attactgtgc gagaggccac   300
tatgatagtg atggttatta ctccttctcc ggtatggacg tctggggcca agggaccacg   360
gtcaccgtct cctcagcctc caccaagggc ccatcggtct tccccctggc gccctgctcc   420
aggagcacct ccgagagcac agcggccctg ggctgcctgg tcaaggacta cttccccgaa   480
ccggtgacgg tgtcgtggaa ctcaggcgct ctgaccagcg gcgtgcacac cttcccggct   540
```

-continued

```
gtcctacagt cctcaggact ctactccctc agcagcgtag tgaccgtgcc ctccagcaac      600
ttcggcaccc agacctacac ctgcaacgta gatcacaagc ccagcaacac caaggtggac      660
aagacagttg agcgcaaatg ttgtgtcgag tgcccaccgt gcccagcacc acctgtggca      720
ggaccgtcag tcttcctctt ccccccaaaa cccaaggaca ccctcatgat ctcccggacc      780
cctgaggtca cgtgcgtggt ggtggacgtg agccacgaag accccgaggt ccagttcaac      840
tggtacgtgg acggcgtgga ggtgcataat gccaagacaa agccacggga ggagcagttc      900
aacagcacgt tccgtgtggt cagcgtcctc accgtcgtgc accaggactg gctgaacggc      960
aaggagtaca agtgcaaggt ctccaacaaa ggcctcccag cccccatcga gaaaaccatc      1020
tccaaaacca aagggcagcc ccgagaacca caggtgtaca ccctgccccc atcccgggag      1080
gagatgacca agaaccaggt cagcctgacc tgcctggtca aaggcttcta ccccagcgac      1140
atcgccgtgg agtgggagag caatgggcag ccggagaaca actacaagac cacacctccc      1200
atgctggact ccgacggctc cttcttcctc tacagcaagc tcaccgtgga caagagcagg      1260
tggcagcagg ggaacgtctt ctcatgctcc gtgatgcatg aggctctgca caaccactac      1320
acacagaaga gcctctccct gtctccgggt aaa                                  1353
```

<210> SEQ ID NO 82
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Tyr Asp Ser Asp Gly Tyr Tyr Ser Phe Ser Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
```

|   |   |   | 210 |   |   |   | 215 |   |   |   | 220 |   |
|---|---|---|---|---|---|---|---|---|---|---|---|---|
| Arg | Lys | Cys | Cys | Val | Glu | Cys | Pro | Pro | Cys | Pro | Ala | Pro | Pro | Val | Ala |
| 225 |   |   |   | 230 |   |   |   | 235 |   |   |   | 240 |

| Gly | Pro | Ser | Val | Phe | Leu | Phe | Pro | Pro | Lys | Pro | Lys | Asp | Thr | Leu | Met |
|---|---|---|---|---|---|---|---|---|---|---|---|---|---|---|---|
|   |   |   | 245 |   |   |   | 250 |   |   |   | 255 |

| Ile | Ser | Arg | Thr | Pro | Glu | Val | Thr | Cys | Val | Val | Val | Asp | Val | Ser | His |
|---|---|---|---|---|---|---|---|---|---|---|---|---|---|---|---|
|   |   |   | 260 |   |   |   | 265 |   |   |   | 270 |

| Glu | Asp | Pro | Glu | Val | Gln | Phe | Asn | Trp | Tyr | Val | Asp | Gly | Val | Glu | Val |
|---|---|---|---|---|---|---|---|---|---|---|---|---|---|---|---|
|   |   |   | 275 |   |   |   | 280 |   |   |   | 285 |

| His | Asn | Ala | Lys | Thr | Lys | Pro | Arg | Glu | Glu | Gln | Phe | Asn | Ser | Thr | Phe |
|---|---|---|---|---|---|---|---|---|---|---|---|---|---|---|---|
| 290 |   |   |   | 295 |   |   |   | 300 |

| Arg | Val | Val | Ser | Val | Leu | Thr | Val | Val | His | Gln | Asp | Trp | Leu | Asn | Gly |
|---|---|---|---|---|---|---|---|---|---|---|---|---|---|---|---|
| 305 |   |   |   | 310 |   |   |   | 315 |   |   |   | 320 |

| Lys | Glu | Tyr | Lys | Cys | Lys | Val | Ser | Asn | Lys | Gly | Leu | Pro | Ala | Pro | Ile |
|---|---|---|---|---|---|---|---|---|---|---|---|---|---|---|---|
|   |   |   | 325 |   |   |   | 330 |   |   |   | 335 |

| Glu | Lys | Thr | Ile | Ser | Lys | Thr | Lys | Gly | Gln | Pro | Arg | Glu | Pro | Gln | Val |
|---|---|---|---|---|---|---|---|---|---|---|---|---|---|---|---|
|   |   |   | 340 |   |   |   | 345 |   |   |   | 350 |

| Tyr | Thr | Leu | Pro | Pro | Ser | Arg | Glu | Glu | Met | Thr | Lys | Asn | Gln | Val | Ser |
|---|---|---|---|---|---|---|---|---|---|---|---|---|---|---|---|
|   |   | 355 |   |   |   | 360 |   |   |   | 365 |

| Leu | Thr | Cys | Leu | Val | Lys | Gly | Phe | Tyr | Pro | Ser | Asp | Ile | Ala | Val | Glu |
|---|---|---|---|---|---|---|---|---|---|---|---|---|---|---|---|
| 370 |   |   |   | 375 |   |   |   | 380 |

| Trp | Glu | Ser | Asn | Gly | Gln | Pro | Glu | Asn | Asn | Tyr | Lys | Thr | Thr | Pro | Pro |
|---|---|---|---|---|---|---|---|---|---|---|---|---|---|---|---|
| 385 |   |   |   | 390 |   |   |   | 395 |   |   |   | 400 |

| Met | Leu | Asp | Ser | Asp | Gly | Ser | Phe | Phe | Leu | Tyr | Ser | Lys | Leu | Thr | Val |
|---|---|---|---|---|---|---|---|---|---|---|---|---|---|---|---|
|   |   |   | 405 |   |   |   | 410 |   |   |   | 415 |

| Asp | Lys | Ser | Arg | Trp | Gln | Gln | Gly | Asn | Val | Phe | Ser | Cys | Ser | Val | Met |
|---|---|---|---|---|---|---|---|---|---|---|---|---|---|---|---|
|   |   |   | 420 |   |   |   | 425 |   |   |   | 430 |

| His | Glu | Ala | Leu | His | Asn | His | Tyr | Thr | Gln | Lys | Ser | Leu | Ser | Leu | Ser |
|---|---|---|---|---|---|---|---|---|---|---|---|---|---|---|---|
|   |   |   | 435 |   |   |   | 440 |   |   |   | 445 |

| Pro | Gly | Lys |
|---|---|---|
|   | 450 |

```
<210> SEQ ID NO 83
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag gcttgagtg gatgggatgg atggacccta acagtggtaa cacaggctat     180
gcacagaagt tccagggcag agtcaccatg accaggaaca cctccataag cacagcctac     240
atggagctga gcagcctgag atctgaggac acggccgtgt attactgtgc gagaggccac     300
tatgatagtg atggttatta ctccttctcc ggtatggacg tctggggcca agggaccacg     360
gtcaccgtct cctca                                                      375

<210> SEQ ID NO 84
<211> LENGTH: 125
<212> TYPE: PRT
<213> ORGANISM: Artificial Sequence
<220> FEATURE:
<223> OTHER INFORMATION: Description of Artificial Sequence: Synthetic
```

-continued

```
    polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Tyr Asp Ser Asp Gly Tyr Tyr Ser Phe Ser Gly Met
            100                 105                 110

Asp Val Trp Gly Gln Gly Thr Thr Val Thr Val Ser Ser
        115                 120                 125

<210> SEQ ID NO 85
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agttatgata tcaac                                                          15

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Tyr Asp Ile Asn
1               5

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tggatggacc ctaacagtgg taacacaggc tatgcacaga gttccaggg c                   51

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

```
Trp Met Asp Pro Asn Ser Gly Asn Thr Gly Tyr Ala Gln Lys Phe Gln
1               5                   10                  15

Gly

<210> SEQ ID NO 89
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ggccactatg atagtgatgg ttattactcc ttctccggta tggacgtc              48

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly His Tyr Asp Ser Asp Gly Tyr Tyr Ser Phe Ser Gly Met Asp Val
1               5                   10                  15

<210> SEQ ID NO 91
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gatattgtga tgactcagtc tccactctcc ctgcccgtca cccctggaga gccggcctcc    60
atctcctgta ggtctagtca gagcctcctg cataggaatg gatacaacta cttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc    240 agcagagtgg aggctgagga tgttggggtt tattactgca tgcaagctct acaaactcct   300
ccggccactt tcggcggagg gaccaaggtg gagatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc    600 gaagtcaccc atcagggcct gagctcgccc gtcacaaaga gcttcaacag gggagagtgt   660

<210> SEQ ID NO 92
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                85                  90                  95

Leu Gln Thr Pro Pro Ala Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 93
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gatattgtga tgactcagtc tccactctcc ctgcccgtca cccctggaga gccggcctcc    60
atctcctgta ggtctagtca gagcctcctg cataggaatg gatacaacta cttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
ccggccactt tcggcggagg gaccaaggtg gagatcaaa                          339

<210> SEQ ID NO 94
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Arg
            20                  25                  30
```

```
Asn Gly Tyr Asn Tyr Leu Asp Trp Tyr Leu Gln Lys Pro Gly Gln Ser
         35                  40                  45
Pro Gln Leu Leu Ile Tyr Leu Gly Ser Asn Arg Ala Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Pro Ala Thr Phe Gly Gly Gly Thr Lys Val Glu Ile
            100                 105                 110
Lys

<210> SEQ ID NO 95
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aggtctagtc agagcctcct gcataggaat ggatacaact acttggat              48

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ser Ser Gln Ser Leu Leu His Arg Asn Gly Tyr Asn Tyr Leu Asp
 1               5                  10                  15

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ttgggttcta atcgggcctc c                                           21

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Gly Ser Asn Arg Ala Ser
 1               5

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 99
atgcaagctc tacaaactcc tccggccact                                      30

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Met Gln Ala Leu Gln Thr Pro Pro Ala Thr
1               5                   10

<210> SEQ ID NO 101
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg gctggagtg gattggggaa atccatcata gtggaagcac caactacaac      180
ccgtccctca gagtcgagt caccatatca gtagacacgt ccaagaacca gttctccctg      240
aagctgagct ctgtgaccgc cgcggacacg gctgtgtatt actgtgcgag agacaactgg      300
aacgactctt tctactacta ctacggtatg gacgtctggg gccaagggac cacggtcacc      360
gtctcctcag cctccaccaa gggcccatcg gtcttccccc tggcgccctg ctccaggagc      420
acctccgaga gcacagcggc cctgggctgc ctggtcaagg actacttccc cgaaccggtg      480
acggtgtcgt ggaactcagg cgctctgacc agcggcgtgc acaccttccc agctgtccta      540
cagtcctcag gactctactc cctcagcagc gtggtgaccg tgccctccag caacttcggc      600
acccagacct acacctgcaa cgtagatcac aagcccagca caccaaggt ggacaagaca       660 gttgagcgca aatgttgtgt cgagtgccca ccgtgcccag caccacctgt ggcaggaccg      720
tcagtcttcc tcttcccccc aaaacccaag gacaccctca tgatctcccg gacccctgag      780
gtcacgtgcg tggtggtgga cgtgagccac gaagaccccg aggtccagtt caactggtac      840
gtggacggcg tggaggtgca taatgccaag acaaagccac gggaggagca gttcaacagc      900
acgttccgtg tggtcagcgt cctcaccgtt gtgcaccagg actggctgaa cggcaaggag      960
tacaagtgca aggtctccaa caaaggcctc ccagccccca tcgagaaaac catctccaaa     1020
accaaagggc agccccgaga accacaggtg tacaccctgc ccccatcccg ggaggagatg     1080
accaagaacc aggtcagcct gacctgcctg gtcaaaggct tctacccag cgacatcgcc       1140 gtggagtggg agagcaatgg gcagccggag aacaactaca agaccacacc tcccatgctg      1200
gactccgacg gctccttctt cctctacagc aagctcaccg tggacaagag caggtggcag      1260
caggggaacg tcttctcatg ctccgtgatg catgaggctc tgcacaacca ctacacgcag      1320
aagagcctct ccctgtctcc gggtaaa                                         1347

<210> SEQ ID NO 102
<211> LENGTH: 449

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102
```

| | | | | | | | | | | | | | | | |
|---|---|---|---|---|---|---|---|---|---|---|---|---|---|---|---|
| Gln | Val | Gln | Leu | Gln | Gln | Trp | Gly | Ala | Gly | Leu | Leu | Lys | Pro | Ser | Glu |
| 1 | | | | 5 | | | | | 10 | | | | | 15 | |
| Thr | Leu | Ser | Leu | Thr | Cys | Ala | Val | Tyr | Gly | Gly | Ser | Phe | Ser | Gly | Tyr |
| | | | 20 | | | | | 25 | | | | | 30 | | |
| Tyr | Trp | Ser | Trp | Ile | Arg | Gln | Pro | Pro | Gly | Lys | Gly | Leu | Glu | Trp | Ile |
| | | 35 | | | | | 40 | | | | | 45 | | | |
| Gly | Glu | Ile | His | His | Ser | Gly | Ser | Thr | Asn | Tyr | Asn | Pro | Ser | Leu | Lys |
| | 50 | | | | | 55 | | | | | 60 | | | | |
| Ser | Arg | Val | Thr | Ile | Ser | Val | Asp | Thr | Ser | Lys | Asn | Gln | Phe | Ser | Leu |
| 65 | | | | | 70 | | | | | 75 | | | | | 80 |
| Lys | Leu | Ser | Ser | Val | Thr | Ala | Ala | Asp | Thr | Ala | Val | Tyr | Tyr | Cys | Ala |
| | | | | 85 | | | | | 90 | | | | | 95 | |
| Arg | Asp | Asn | Trp | Asn | Asp | Ser | Phe | Tyr | Tyr | Tyr | Gly | Met | Asp | Val | |
| | | | 100 | | | | | 105 | | | | | 110 | | |
| Trp | Gly | Gln | Gly | Thr | Thr | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Cys | Ser | Arg | Ser | Thr | Ser | Glu | Ser |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Asn | Phe | Gly | Thr | Gln | Thr | Tyr | Thr | Cys | Asn | Val |
| | | 195 | | | | | 200 | | | | | 205 | | | |
| Asp | His | Lys | Pro | Ser | Asn | Thr | Lys | Val | Asp | Lys | Thr | Val | Glu | Arg | Lys |
| | 210 | | | | | 215 | | | | | 220 | | | | |
| Cys | Cys | Val | Glu | Cys | Pro | Pro | Cys | Pro | Ala | Pro | Pro | Val | Ala | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Gln | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Phe | Asn | Ser | Thr | Phe | Arg | Val |
| | 290 | | | | | 295 | | | | | 300 | | | | |
| Val | Ser | Val | Leu | Thr | Val | Val | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Gly | Leu | Pro | Ala | Pro | Ile | Glu | Lys |
| | | | | 325 | | | | | 330 | | | | | 335 | |
| Thr | Ile | Ser | Lys | Thr | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |

-continued

```
Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 103
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gacatccaga tgacccagtc tccatcatca ctgtctgcat ctgtaggaga cagagtcacc    60
atcacatgtc gggcgagtca gggcattagc aatcatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataataggc acccattcac tttcggccct   300
gggaccaaag tggatatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc   600
ctgagctcgc ccgtcacaaa gagcttcaac aggggagagt gt                      642

<210> SEQ ID NO 104
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn His
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Arg His Pro Phe
                85                  90                  95

Thr Phe Gly Pro Gly Thr Lys Val Asp Ile Lys Arg Thr Val Ala Ala
            100                 105                 110
```

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 105
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
caggttcacc tggtgcagtc tggagctgag gtgaagatgc ctggggcctc agtgaaggtc        60
tcctgcaagg cttctggtta cacctttacc agctatggta tcagctgggt gcgacaggcc       120
cctggacaag gcttgagtg gatgggatgg atcagcgctt acaatggtaa cacaaactat        180
gcacagaagc tccagggcag aatcaccatg accacagaca catccacgag cacagcctac       240
atggacctga ggagcctgag atctgacgac acggccgtgt attactgtgc gagagatggg       300
gattactatg atccttttga ctactggggc cagggaaccc tggtcaccgt ctcctcagcc       360
tccaccaagg gcccatcggt cttccccctg gcgccctgct ccaggagcac ctccgagagc       420
acagcggccc tgggctgcct ggtcaaggac tacttccccg aaccggtgac ggtgtcgtgg       480
aactcaggcg ctctgaccag cggcgtgcac accttcccag ctgtcctaca gtcctcagga       540
ctctactccc tcagcagcgt ggtgaccgtg ccctccagca acttcggcac ccagacctac       600
acctgcaacg tagatcacaa gcccagcaac accaaggtgg acaagacagt tgagcgcaaa       660
tgttgtgtcg agtgcccacc gtgcccagca ccacctgtgg caggaccgtc agtcttcctc       720
ttccccccaa aacccaagga caccctcatg atctcccgga cccctgaggt cacgtgcgtg       780
gtggtggacg tgagccacga agaccccgag gtccagttca actggtacgt ggacggcgtg       840
gaggtgcata atgccaagac aaagccacgg gaggagcagt tcaacagcac gttccgtgtg       900
gtcagcgtcc tcaccgttgt gcaccaggac tggctgaacg gcaaggagta caagtgcaag       960
gtctccaaca aaggcctccc agcccccatc gagaaaacca tctccaaaac caaagggcag      1020
ccccgagaac cacaggtgta caccctgccc ccatcccggg aggagatgac caagaaccag      1080
gtcagcctga cctgcctggt caaaggcttc taccccagcg acatcgccgt ggagtgggag      1140
agcaatgggc agccggagaa caactacaag accacacctc ccatgctgga ctccgacggc      1200
tccttcttcc tctacagcaa gctcaccgtg gacaagagca ggtggcagca ggggaacgtc      1260
ttctcatgct ccgtgatgca tgaggctctg cacaaccact acacgcagaa gagcctctcc      1320
ctgtctccgg gtaaa                                                      1335

<210> SEQ ID NO 106
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Gln Val His Leu Val Gln Ser Gly Ala Glu Val Lys Met Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Ile Thr Met Thr Thr Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Asp Gly Asp Tyr Tyr Asp Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 107
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
gacatccaga tgacccagtc tccatcctcc ctgtctgcat ctgtaggaga cagagtcacc      60
atcacttgcc ggacaagtca gagtattagc aactggttaa attggtatca gcagaaacca    120
gggaaagccc ctaaactcct gatctatggt gcctccactt tgaaaagtgg ggtcccatca    180
aggttcagtg gcagtgaatc tgggacagat ttcactctca ccatcagcag tctgcaacct    240
gaagattttg caacttacta ctgtcaacag agttacagta cccctccgac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 108
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Gly Ala Ser Thr Leu Lys Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
```

```
                100              105              110
Pro Ser Val Phe Ile Phe Pro Pro Ser Asp Glu Gln Leu Lys Ser Gly
        115                  120                  125

Thr Ala Ser Val Val Cys Leu Leu Asn Asn Phe Tyr Pro Arg Glu Ala
    130                  135                  140

Lys Val Gln Trp Lys Val Asp Asn Ala Leu Gln Ser Gly Asn Ser Gln
145                  150                  155                  160

Glu Ser Val Thr Glu Gln Asp Ser Lys Asp Ser Thr Tyr Ser Leu Ser
                165                  170                  175

Ser Thr Leu Thr Leu Ser Lys Ala Asp Tyr Glu Lys His Lys Val Tyr
        180                  185                  190

Ala Cys Glu Val Thr His Gln Gly Leu Ser Ser Pro Val Thr Lys Ser
    195                  200                  205

Phe Asn Arg Gly Glu Cys
    210
```

<210> SEQ ID NO 109
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag gcttgagtg gatgggatgg atggacccta cagtggtaa cacaggctat    180
gcacagaagt tccagggcag agtcaccatg accaggaaca cctccataag cacagcctac   240
atggagctga gcagcctgag atctgaggac acggccgtgt attactgtgc gagaggccac   300
tatgatagtg atggttatta ctccttctcc ggtatggacg tctggggcca agggaccacg   360
gtcaccgtct cctcagcctc caccaagggc ccatcggtct tccccctggc gccctgctcc   420
aggagcacct ccgagagcac agcggccctg ggctgcctgg tcaaggacta cttccccgaa   480
ccggtgacgg tgtcgtggaa ctcaggcgct ctgaccagcg gcgtgcacac cttcccagct   540
gtcctacagt cctcaggact ctactccctc agcagcgtgg tgaccgtgcc ctccagcaac   600
ttcggcaccc agacctacac ctgcaacgta gatcacaagc ccagcaacac caaggtggac   660
aagacagttg agcgcaaatg ttgtgtcgag tgcccaccgt gcccagcacc acctgtggca   720
ggaccgtcag tcttcctctt ccccccaaaa cccaaggaca cctcatgat ctcccggacc    780
cctgaggtca cgtgcgtggt ggtggacgtg agccacgaag accccgaggt ccagttcaac   840
tggtacgtgg acggcgtgga ggtgcataat gccaagacaa agccacggga ggagcagttc   900
aacagcacgt tccgtgtggt cagcgtcctc accgttgtgc accaggactg gctgaacggc   960
aaggagtaca agtgcaaggt ctccaacaaa ggcctcccag cccccatcga gaaaaccatc  1020
tccaaaacca aagggcagcc ccgagaacca caggtgtaca ccctgccccc atcccgggag  1080
gagatgacca agaaccaggt cagcctgacc tgcctggtca aaggcttcta ccccagcgac  1140
atcgccgtgg agtgggagag caatgggcag ccggagaaca actacaagac cacacctccc  1200
atgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                                1353
```

<210> SEQ ID NO 110
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Tyr Asp Ser Asp Gly Tyr Tyr Ser Phe Ser Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
```

```
                355                 360                 365
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 111
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gatattgtga tgactcagtc tccactctcc ctgcccgtca cccctggaga gccggcctcc        60
atctcctgta ggtctagtca gagcctcctg cataggaatg gatacaacta cttggattgg      120
tacctgcaga agccagggca gtctccacag ctcctgatct atttgggttc taatcgggcc      180
tccggggtcc ctgacaggtt cagtggcagt ggatcaggca cagattttac actgaaaatc      240
agcagagtgg aggctgagga tgttggggtt tattactgca tgcaagctct acaaactcct      300
ccggccactt tcggcggagg gaccaaggtg gagatcaaac gaactgtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660

<210> SEQ ID NO 112
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ala
            85                  90                  95

Leu Gln Thr Pro Pro Ala Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

-continued

<400> SEQUENCE: 120

000

<210> SEQ ID NO 121
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag ggcttgagtg gatgggatgg atggacccta cagtggtaa cacaggctat      180
gcacagaagt tccagggcag agtcaccatg accaggaaca cctccataag cacagcctac     240
atggagctga gcagcctgag atctgaggac acggccgtgt attactgtgc gagaggctac     300
tatgatagtg atggttatta ctccttctcc ggtatggacg tctggggcca agggaccacg     360
gtcaccgtct cctcagcctc caccaagggc ccatcggtct tccccctggc gccctgctcc     420
aggagcacct ccgagagcac agcggccctg ggctgcctgg tcaaggacta cttccccgaa     480
ccggtgacgg tgtcgtggaa ctcaggcgct ctgaccagcg gcgtgcacac cttcccggct     540
gtcctacagt cctcaggact ctactccctc agcagcgtag tgaccgtgcc ctccagcaac     600
ttcggcaccc agacctacac ctgcaacgta gatcacaagc ccagcaacac caaggtggac     660
aagacagttg agcgcaaatg ttgtgtcgag tgcccaccgt gcccagcacc acctgtggca     720
ggaccgtcag tcttcctctt ccccccaaaa cccaaggaca cctcatgat ctcccggacc      780
cctgaggtca cgtgcgtggt ggtggacgtg agccacgaag accccgaggt ccagttcaac     840
tggtacgtgg acggcgtgga ggtgcataat gccaagacaa agccacggga ggagcagttc     900
aacagcacgt tccgtgtggt cagcgtcctc accgtcgtgc accaggactg gctgaacggc     960
aaggagtaca agtgcaaggt ctccaacaaa ggcctcccag cccccatcga gaaaaccatc    1020
tccaaaacca agggcagcc cgagaaccag gtgtaca ccctgccccc atcccgggag         1080
gagatgacca gaaccaggt cagcctgacc tgcctggtca aaggcttcta ccccagcgac     1140
atcgccgtgg agtgggagag caatgggcag ccggagaaca actacaagac cacacctccc    1200
atgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acacagaaga gcctctccct gtctccgggt aaa                                 1353
```

<210> SEQ ID NO 122
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met

-continued

```
                 35                  40                  45
Gly Trp Met Asp Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Tyr Asp Ser Asp Gly Tyr Tyr Ser Phe Ser Gly Met
                100                 105                 110

Asp Val Trp Gly Gln Gly Thr Thr Val Thr Val Ser Ser Ala Ser Thr
                115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Asn Phe Gly Thr Gln Thr Tyr Thr Cys
                195                 200                 205

Asn Val Asp His Lys Pro Ser Asn Thr Lys Val Asp Lys Thr Val Glu
                210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Phe Asn Ser Thr Phe
                290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450
```

<210> SEQ ID NO 123
<211> LENGTH: 375
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 123
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag gcttgagtg gatgggatgg atggacccta acagtggtaa cacaggctat      180
gcacagaagt tccagggcag agtcaccatg accaggaaca cctccataag cacagcctac     240
atggagctga gcagcctgag atctgaggac acggccgtgt attactgtgc gagaggctac     300
tatgatagtg atggttatta ctccttctcc ggtatggacg tctggggcca agggaccacg     360
gtcaccgtct cctca                                                      375

<210> SEQ ID NO 124
<211> LENGTH: 125
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Asp Ser Asp Gly Tyr Tyr Ser Phe Ser Gly Met
            100                 105                 110

Asp Val Trp Gly Gln Gly Thr Thr Val Thr Val Ser Ser
        115                 120                 125

<210> SEQ ID NO 125
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 125
agttatgata tcaac                                                       15

<210> SEQ ID NO 126
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 126

Ser Tyr Asp Ile Asn
1               5

<210> SEQ ID NO 127
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tggatggacc ctaacagtgg taacacaggc tatgcacaga agttccaggg c           51

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Trp Met Asp Pro Asn Ser Gly Asn Thr Gly Tyr Ala Gln Lys Phe Gln
1               5                   10                  15

Gly

<210> SEQ ID NO 129
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggctactatg atagtgatgg ttattactcc ttctccggta tggacgtc                48

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Tyr Asp Ser Asp Gly Tyr Tyr Ser Phe Ser Gly Met Asp Val
1               5                   10                  15

<210> SEQ ID NO 131
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
gatattgtga tgactcagtc tccactctcc ctgcccgtca cccctggaga gccggcctcc    60
atctcctgta ggtctagtca gagcctcctg cataggaatg gatacaacta cttggattgg   120
```

```
tacctgcaga agccagggca gtctccacag ctcctgatct atttgggttc taatcgggcc      180 tccgggtcc ctgacaggtt cagtggcagt ggatcaggca cagattttac actgaaaatc      240
agcagagtgg aggctgagga tgttggggtt tattactgca tgcaagctct acaaactcct      300
ccggccactt tcggcggagg gaccaaggtg gagatcaaac gaactgtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
```

<210> SEQ ID NO 132
<211> LENGTH: 220
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 132

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Ala Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 133
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
gatattgtga tgactcagtc tccactctcc ctgcccgtca ccctggaga gccggcctcc      60
atctcctgta ggtctagtca gagcctcctg cataggaatg gatacaacta cttggattgg    120
tacctgcaga agccagggca gtctccacag ctcctgatct atttgggttc taatcgggcc    180
tccggggtcc ctgacaggtt cagtggcagt ggatcaggca cagatttttac actgaaaatc   240
agcagagtgg aggctgagga tgttggggtt tattactgca tgcaagctct acaaactcct    300
ccggccactt tcggcggagg gaccaaggtg gagatcaaa                           339
```

<210> SEQ ID NO 134
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Arg
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Pro Ala Thr Phe Gly Gly Gly Thr Lys Val Glu Ile
            100                 105                 110
Lys
```

<210> SEQ ID NO 135
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135

```
aggtctagtc agagcctcct gcataggaat ggatacaact acttggat                  48
```

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

```
Arg Ser Ser Gln Ser Leu Leu His Arg Asn Gly Tyr Asn Tyr Leu Asp
1               5                   10                  15
```

<210> SEQ ID NO 137

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ttgggttcta atcgggcctc c                                              21

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Gly Ser Asn Arg Ala Ser
1               5

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atgcaagctc tacaaactcc tccggccact                                     30

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Met Gln Ala Leu Gln Thr Pro Pro Ala Thr
1               5                   10

<210> SEQ ID NO 141
<211> LENGTH: 317
<212> TYPE: PRT
<213> ORGANISM: Homo sapiens

<400> SEQUENCE: 141

Pro Thr Val Lys Ile Leu Gln Ser Ser Cys Asp Gly Gly Gly His Phe
1               5                   10                  15

Pro Pro Thr Ile Gln Leu Leu Cys Leu Val Ser Gly Tyr Thr Pro Gly
                20                  25                  30

Thr Ile Asn Ile Thr Trp Leu Glu Asp Gly Gln Val Met Asp Val Asp
            35                  40                  45

Leu Ser Thr Ala Ser Thr Thr Gln Glu Gly Glu Leu Ala Ser Thr Gln
        50                  55                  60

Ser Glu Leu Thr Leu Ser Gln Lys His Trp Leu Ser Asp Arg Thr Tyr
65                  70                  75                  80

Thr Cys Gln Val Thr Tyr Gln Gly His Thr Phe Glu Asp Ser Thr Lys
                85                  90                  95

Lys Cys Ala Asp Ser Asn Pro Arg Gly Val Ser Ala Tyr Leu Ser Arg
```

```
                100                 105                 110
Pro Ser Pro Phe Asp Leu Phe Ile Arg Lys Ser Pro Thr Ile Thr Cys
        115                 120                 125

Leu Val Val Asp Leu Ala Pro Ser Lys Gly Thr Val Asn Leu Thr Trp
    130                 135                 140

Ser Arg Ala Ser Gly Lys Pro Val Asn His Ser Thr Arg Lys Glu Glu
145                 150                 155                 160

Lys Gln Arg Asn Gly Thr Leu Thr Val Thr Ser Thr Leu Pro Val Gly
                165                 170                 175

Thr Arg Asp Trp Ile Glu Gly Glu Thr Tyr Gln Cys Arg Val Thr His
            180                 185                 190

Pro His Leu Pro Arg Ala Leu Met Arg Ser Thr Thr Lys Thr Ser Gly
        195                 200                 205

Pro Arg Ala Ala Pro Glu Val Tyr Ala Phe Ala Thr Pro Glu Trp Pro
    210                 215                 220

Gly Ser Arg Asp Lys Arg Thr Leu Ala Cys Leu Ile Gln Asn Phe Met
225                 230                 235                 240

Pro Glu Asp Ile Ser Val Gln Trp Leu His Asn Glu Val Gln Leu Pro
                245                 250                 255

Asp Ala Arg His Ser Thr Thr Gln Pro Arg Lys Thr Lys Gly Ser Gly
            260                 265                 270

Phe Phe Val Phe Ser Arg Leu Glu Val Thr Arg Ala Glu Trp Glu Gln
        275                 280                 285

Lys Asp Glu Phe Ile Cys Arg Ala Val His Glu Ala Ala Ser Pro Ser
    290                 295                 300

Gln Thr Val Gln Arg Ala Val Ser Val Asn Pro Gly Lys
305                 310                 315

<210> SEQ ID NO 142
<211> LENGTH: 220
<212> TYPE: PRT
<213> ORGANISM: Homo sapiens

<400> SEQUENCE: 142

Cys Ala Asp Ser Asn Pro Arg Gly Val Ser Ala Tyr Leu Ser Arg Pro
1               5                   10                  15

Ser Pro Phe Asp Leu Phe Ile Arg Lys Ser Pro Thr Ile Thr Cys Leu
                20                  25                  30

Val Val Asp Leu Ala Pro Ser Lys Gly Thr Val Asn Leu Thr Trp Ser
            35                  40                  45

Arg Ala Ser Gly Lys Pro Val Asn His Ser Thr Arg Lys Glu Glu Lys
        50                  55                  60

Gln Arg Asn Gly Thr Leu Thr Val Thr Ser Thr Leu Pro Val Gly Thr
65                  70                  75                  80

Arg Asp Trp Ile Glu Gly Glu Thr Tyr Gln Cys Arg Val Thr His Pro
                85                  90                  95

His Leu Pro Arg Ala Leu Met Arg Ser Thr Thr Lys Thr Ser Gly Pro
            100                 105                 110

Arg Ala Ala Pro Glu Val Tyr Ala Phe Ala Thr Pro Glu Trp Pro Gly
        115                 120                 125

Ser Arg Asp Lys Arg Thr Leu Ala Cys Leu Ile Gln Asn Phe Met Pro
    130                 135                 140

Glu Asp Ile Ser Val Gln Trp Leu His Asn Glu Val Gln Leu Pro Asp
145                 150                 155                 160
```

Ala Arg His Ser Thr Thr Gln Pro Arg Lys Thr Lys Gly Ser Gly Phe
            165                 170                 175

Phe Val Phe Ser Arg Leu Glu Val Thr Arg Ala Glu Trp Glu Gln Lys
        180                 185                 190

Asp Glu Phe Ile Cys Arg Ala Val His Glu Ala Ala Ser Pro Ser Gln
    195                 200                 205

Thr Val Gln Arg Ala Val Ser Val Asn Pro Gly Lys
210                 215                 220

<210> SEQ ID NO 143
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cctttctctc cacaggcgcg cactcccagg tgcagctaca gcagtgg                47

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tacgtgccaa gcatcctcgc                                               20

<210> SEQ ID NO 145
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ctttctctcc acaggcgtgc actccgacat ccagatgacc cagtctcc               48

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
aggctggaac tgaggagcag gtg                                           23

<210> SEQ ID NO 147
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cctttctctc cacaggcgcg cactcccagg ttcacctggt gcagtct                47

<210> SEQ ID NO 148

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ctttctctcc acaggcgtgc actccgacat ccagatgacc cagtct            46

<210> SEQ ID NO 149
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cctttctctc cacaggcgcg cactcccagg tgcagctggt gcagtct           47

<210> SEQ ID NO 150
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ctttctctcc acaggcgtgc actccgatat tgtgatgact cagtctccac         50

<210> SEQ ID NO 151
<211> LENGTH: 121
<212> TYPE: PRT
<213> ORGANISM: Homo sapiens

<400> SEQUENCE: 151
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asn Trp Asn Asp Tyr Tyr Tyr Gly Met Asp Val Trp Gly
            100                 105                 110

Gln Gly Thr Thr Val Thr Val Ser Ser
        115                 120

```
<210> SEQ ID NO 152
<211> LENGTH: 107
<212> TYPE: PRT
<213> ORGANISM: Homo sapiens

<400> SEQUENCE: 152
```

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Pro Gly Thr Lys Val Asp Ile Lys
            100                 105

<210> SEQ ID NO 153
<211> LENGTH: 123
<212> TYPE: PRT
<213> ORGANISM: Homo sapiens

<400> SEQUENCE: 153

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Tyr Asp Ser Ser Gly Tyr Tyr Tyr Phe Asp Tyr
            100                 105                 110

Trp Gly Gln Gly Thr Leu Val Thr Val Ser Ser
        115                 120

<210> SEQ ID NO 154
<211> LENGTH: 107
<212> TYPE: PRT
<213> ORGANISM: Homo sapiens

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105
```

<210> SEQ ID NO 155
<211> LENGTH: 120
<212> TYPE: PRT
<213> ORGANISM: Homo sapiens

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ser Tyr Tyr Tyr Gly Met Asp Val Trp Gly Gln
            100                 105                 110

Gly Thr Thr Val Thr Val Ser Ser
        115                 120

<210> SEQ ID NO 156
<211> LENGTH: 111
<212> TYPE: PRT
<213> ORGANISM: Homo sapiens

<400> SEQUENCE: 156

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Thr Phe Gly Gly Gly Thr Lys Val Glu Ile Lys
            100                 105                 110

<210> SEQ ID NO 157
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
actcacctga ggagacggtg accgtggtcc c                              31

<210> SEQ ID NO 158
<211> LENGTH: 58
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 158
cctattcctt aattaagtta ttctactcac gtttgatatc cactttggtc ccagggcc        58

<210> SEQ ID NO 159
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
actcacctga ggagacggtg accagggttc c                                     31

<210> SEQ ID NO 160
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
cctattcctt aattaagtta ttctactcac gtttgatttc caccttggtc ccttggcc        58

<210> SEQ ID NO 161
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
actcacctga ggagacggtg accgtggt                                         28

<210> SEQ ID NO 162
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
tatattcctt aattaagtta ttctactcac gtttgatctc caccttggtc cct             53

<210> SEQ ID NO 163
<211> LENGTH: 97
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
actcacctga ggagacggtg accgtggtcc cttggcccca gacgtccata ccgtagtagt      60
agtagaagtt gtcgttccag ttgtctctcg cacagta                               97

<210> SEQ ID NO 164
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ttgcaaagtg gggtcccatc aaggttcagc ggcagtggat ctggg              45

<210> SEQ ID NO 165
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cccagatcca ctgccgctga accttgatgg gaccccactt tgcaa              45

<210> SEQ ID NO 166
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cctttctctc cacaggcgcg cactcccagg ttcacctggt gcagtctgga gctgaggtga   60
agaagcctgg ggcctcagtg aaggtc                                        86

<210> SEQ ID NO 167
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gacacatcca cgagcacagc ctacatggaa ctgaggagcc tgagatctga cgac         54

<210> SEQ ID NO 168
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gtcgtcagat ctcaggctcc tcagttccat gtaggctgtg ctcgtggatg tgtc         54

<210> SEQ ID NO 169
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
cctttctctc cacaggcgcg cactcccagg tccagctggt gcagtct                47

<210> SEQ ID NO 170
```

```
-continued

<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ggagacagag tcaccatcac ttgccgggca agtcagagta ttagcaactg gtta        54

<210> SEQ ID NO 171
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
taaccagttg ctaatactct gacttgcccg gcaagtgatg gtgactctgt ctcc        54

<210> SEQ ID NO 172
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
aaactcctga tctatggtgc ctccagtttg aaaagtgggg tcccatcaag g           51

<210> SEQ ID NO 173
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccttgatggg accccacttt tcaaactgga ggcaccatag atcaggagtt t           51

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Gly Gly Gly Ser Gly Gly Gly Gly Ser Gly Gly Gly Gly Ser
1               5                   10                  15
```

ANTI-IGE ANTIBODIES

CROSS-REFERENCE TO RELATED APPLICATIONS

This application claims the priority benefit of the U.S. Provisional Application Ser. No. 60/921,546, filed Apr. 2, 2007; and U.S. Provisional Application Ser. No. 61/008,755, filed Dec. 20, 2007, both of which are hereby incorporated by reference in their entirety.

SEQUENCE LISTING

The instant application contains a Sequence Listing which has been submitted via EFS-Web and is hereby incorporated by reference in its entirety. Said ASCII copy, created on Jun. 10, 2010, is named ABX-PF10.txt, and is 136,938 bytes in size.

FIELD OF THE INVENTION

The present invention relates to novel human antibodies specifically directed against human immunoglobulin E (anti-IgE). The antibodies of the invention are especially suitable for treating asthma, in particular allergic asthma, as well as other IgE-mediated disorders including allergic rhinitis and food allergies.

BACKGROUND OF THE INVENTION

Asthma is a chronic inflammatory disorder of the airways causing recurrent episodes of wheezing, breathlessness, chest tightness, and/or coughing in susceptible individuals. Those skilled in the art distinguish various types of asthma, including: allergic asthma, which is thought to arise in patients having developed a hypersensitivity to environmental allergens; drug-induced asthma, typically triggered by sensitivity to aspirin or other COX inhibitors; exercise-induced asthma; near-fatal and hyperacute asthma; nocturnal asthma; occupational asthma, generally caused by exposure to certain chemicals in the workplace. Thus asthma can be triggered by various stimuli, including: airborne allergens, such as dust-mites, pollens, animal dander, fungal spores, feathers . . . (extrinsic asthma); non specific irritants, such as tobacco smoke, chemical fumes, pollution, sulphur dioxide . . . (intrinsic asthma).

Immunoglobulin E (IgE) has been shown to be involved in allergic reactions, in particular in allergic asthma. Very recently, a monoclonal antibody (omalizumab, also termed E25, marketed under the trade name Xolair®; Presta et al. *J Immunol.* 1993 Sep. 1; 151(5):2623-32.) gained approval from several agencies around the world. Despite showing efficacy against severe asthma, this antibody still has some drawbacks. Firstly this is a humanized murine monoclonal antibody, and as such, does not entirely preclude immunological reactions in human patients, thus possibly raising some safety concerns. Secondly, the dose of omalizumab used in treating severe asthma is based on both body weight and the level of circulating free IgE. Patients whose body weight and circulating free IgE that deviate from a specified range are recommended not to use this treatment. Those patients that can be treated may require to receive up to three subcutaneous injections once every two weeks. This heavily impacts on the costs of treatment, as well as on the quality of life of the patients.

It is desirable to provide a fully human anti-IgE monoclonal antibody, which would minimize any concern as to the use of murine antibodies in human patients. Further, it is desirable to provide a more potent anti-IgE monoclonal antibody. Increased potency would typically result in the following benefits: lower doses required to achieve clinical benefits, lower volume of injection required (for subcutaneous administration), lower cost of treatment, increased chances of treatment success, decreased frequency of administration in the treatment regimen, thus providing access to treatment to a wider population of patients, including patients with higher body weight and/or high levels of circulating IgE, and improving patients' quality of life.

SUMMARY OF THE INVENTION

The present invention relates to a human antibody directed against human IgE (herein sometimes referred to as anti-IgE antibody), or an antigen binding portion thereof.

In another embodiment, the anti-IgE antibody or portion thereof directed against human IgE has an IC50 of 0.5 µg/mL or less as measured by their ability to reduce IgE binding in a cell binding assay using an RBL-2H3 cell line transfected with the human FcεR1.

In a further embodiment, the anti-IgE antibody or portion thereof has an IC50 of 0.5 µg/mL or less as measured by their ability to inhibit IgE-mediated degranulation of a RBL-2H3 cell line transfected with the human FcεR1, in which RBL-2H3 (FcεR1) cells were cultured with the anti-IgE antibody and human IgE for 48 hours, were washed to remove anti-IgE:IgE complexes, leaving IgE bound to FcεR1, then stimulated with a polyclonal anti-IgE antibody which crosslinks bound IgE, resulting in IgE-mediated degranulation. In a further embodiment, said IC50 is less than 0.2 µg/mL, less than 0.1 µg/mL, less than 0.08 µg/mL or less than 0.02 µg/mL.

In another embodiment, the antibody or antigen-binding portion thereof directed against human IgE does not crosslink receptor-bound IgE and does not stimulate IgE-dependent degranulation of RBL-2H3 (FcεR1) cells cultured with human IgE for 48 hours then washed to remove unbound IgE. The antibody or antigen-binding portion thereof directed against human IgE of the invention do not have agonist activity with isolated RBL-2H3 (FcεR1).

In another embodiment, the antibody or antigen-binding portion thereof directed against human IgE does not crosslink receptor-bound IgE and do not stimulate IgE-dependent degranulation of human blood basophils cultured overnight with human IgE. The antibody or antigen-binding portion thereof directed against human IgE of the invention do not have agonist activity with isolated human blood basophils.

In another embodiment, the antibody or antigen-binding portion thereof directed against human IgE are highly selective for IgE over human IgA, IgG1 and IgG3.

In another embodiment, the antibody or antigen-binding portion thereof binds to the full length of human IgE with an Affinity Constant, $K_D$, of 15 nM or less as measured by surface plasmon resonance (BIAcore). In a further embodiment, the $K_D$ value is of less than 10 nM, less than 5 nM or less than 3 nM as measured by surface plasmon resonance. In certain embodiments, the $K_D$ is from 1 pM to 100 nM. In other embodiments, the $K_D$ is from 1 pM to 5 nM. In other embodiments $K_D$ value is of from 1 pM to 300 pM, or from 1 pM to 200 pM or less than 160 pM. In another embodiment, the antibody or portion thereof has an off rate (kOff) for human IgE of $2 \times 10^{-4}$ $s^{-1}$ or smaller as measured by surface plasmon resonance. For example, in certain embodiments the antibody or portion has a kOff for human IgE of less than $1.5 \times 10^{-4}$ $s^{-1}$, less than $9 \times 10^{-5}$ $s^{-1}$, less than $5 \times 10^{-5}$ $s^{-1}$ or less than $2.5 \times 10^{-5}$ $s^{-1}$. In another embodiment, the antibody or portion thereof has an on rate ($k_a$) for human IgE of more than $1 \times 10^4$ $M^{-1} s^{-1}$, more than $2\times10^4 M^{-1} s^{-1}$, more than $3\times10^4 M^{-1} s^{-1}$, more than $1\times10^5 M^{-1} s^{-1}$ or more than $1.5\times10^5 M^{-1} s^{-1}$.

Such K values can be measured by any technique known those of skill in the art, such as by ELISAs, RIAs, flow cytometry, or surface plasmon resonance, such as BIA-CORE™.

In another embodiment, the antibody or antigen-binding portion thereof directed against human IgE cross-reacts with cynomolgus IgE.

In another embodiment, the anti-IgE antibody or portion thereof competes for binding to human IgE with an antibody selected from the group consisting of recombinant 5.396.1; 5.396.1 Hc-S103N Lc-K61R; recombinant 6.605.1; 6.605.1 (H3Q,M13K,D82E-T25A, T53S); recombinant 5.948.1. and 5.948.1 H100Y.

In another embodiment, the anti-IgE antibody or portion thereof binds to the same epitope of human IgE as an antibody selected from the group consisting of recombinant 5.396.1; 5.396.1 Hc-S103N Lc-K61R; recombinant 6.605.1; 6.605.1 (H3Q,M13K,D82E-T25A, T53S); recombinant 5.948.1. and 5.948.1H100Y.

In one aspect, the present invention provides a human antibody directed against human IgE, or an antigen-binding portion thereof, wherein said antibody has an $IC_{25\ ng/mL}$ (100-5000 ng/mL) of about 0.1-30 µg/mL, wherein the $IC_{25\ ng/mL}$ (100-5000 ng/mL) is defined as the in vitro concentration of antibody required to reduce the free IgE concentration in a serum sample from an initial concentration in the range of about 100-5000 ng/mL to a concentration of about 25 ng/mL.

In another aspect, the present invention provides a human antibody directed against human IgE, or an antigen-binding portion thereof, wherein said antibody has an $IC_{25\ ng/mL}$ (500-1500 ng/mL) of about 1-25 µg/mL, wherein the $IC_{25\ ng/mL}$ (500-1500 ng/mL) is defined as the in vitro concentration of antibody required to reduce the free IgE concentration in a serum sample from an initial concentration in the range of about 500-1500 ng/mL to a concentration of about 25 ng/mL.

In one embodiment, the anti-IgE antibody or portion thereof comprises a H-CDR3 having a sequence selected from the group consisting of SEQ ID NO: 10, 30, 50, 70, 90 and 130.

In one embodiment, the anti-IgE antibody or portion thereof comprises an L-CDR3 having a sequence selected from the group consisting of SEQ ID NO: 20, 40, 60, 80, 100 and 140.

In one embodiment, the anti-IgE antibody or portion is selected from the group consisting of:
   an antibody comprising an H-CDR3 having the sequence of SEQ ID NO: 10 and an LCDR3 having the sequence of SEQ ID NO: 20;
   an antibody comprising an H-CDR3 having the sequence of SEQ ID NO: 30 and an LCDR3 having the sequence of SEQ ID NO: 40;
   an antibody comprising an H-CDR3 having the sequence of SEQ ID NO: 50 and an LCDR3 having the sequence of SEQ ID NO: 60;
   an antibody comprising an H-CDR3 having the sequence of SEQ ID NO: 70 and an LCDR3 having the sequence of SEQ ID NO: 80; and
   an antibody comprising an H-CDR3 having the sequence of SEQ ID NO: 90 and an LCDR3 having the sequence of SEQ ID NO: 100
   an antibody comprising an H-CDR3 having the sequence of SEQ ID NO: 130 and an LCDR3 having the sequence of SEQ ID NO: 140

In another embodiment, the anti-IgE antibody or portion is selected from the group consisting of:
   an antibody comprising a H-CDR set of H-CDRs (H-CDR1, H-CDR2, H-CDR3) respectively having the sequences of SEQ ID NO: 6, 8, 10;
   an antibody comprising a H-CDR set of H-CDRs (H-CDR1, H-CDR2, H-CDR3) respectively having the sequences of SEQ ID NO: 26, 28, 30;
   an antibody comprising a H-CDR set of H-CDRs (H-CDR1, H-CDR2, H-CDR3) respectively having the sequences of SEQ ID NO: 46, 48, 50;
   an antibody comprising a H-CDR set of H-CDRs (H-CDR1, H-CDR2, H-CDR3) respectively having the sequences of SEQ ID NO: 66, 68, 70;
   an antibody comprising a H-CDR set of H-CDRs (H-CDR1, H-CDR2, H-CDR3) respectively having the sequences of SEQ ID NO: 86, 88, 90; and
   an antibody comprising a H-CDR set of H-CDRs (H-CDR1, H-CDR2, H-CDR3) respectively having the sequences of SEQ ID NO: 126, 128, 130.

In another embodiment, the anti-IgE antibody or portion thereof is selected from the group consisting of:
   an antibody comprising an L-CDR set of L-CDRs (L-CDR1, L-CDR2, L-CDR3) respectively having the sequences of SEQ ID NO: 16, 18, 20;
   an antibody comprising an L-CDR set of L-CDRs (L-CDR1, L-CDR2, L-CDR3) respectively having the sequences of SEQ ID NO: 36, 38, 40;
   an antibody comprising an L-CDR set of L-CDRs (L-CDR1, L-CDR2, L-CDR3) respectively having the sequences of SEQ ID NO: 56, 58, 60;
   an antibody comprising an L-CDR set of L-CDRs (L-CDR1, L-CDR2, L-CDR3) respectively having the sequences of SEQ ID NO: 76, 78, 80;
   an antibody comprising an L-CDR set of L-CDRs (L-CDR1, L-CDR2, L-CDR3) respectively having the sequences of SEQ ID NO: 96, 98, 100; and
   an antibody comprising an L-CDR set of L-CDRs (L-CDR1, L-CDR2, L-CDR3) respectively having the sequences of SEQ ID NO: 136, 138, 140.

In another embodiment, the anti-IgE antibody or portion thereof is selected from the group consisting of:
   an antibody comprising a H-CDR set of H-CDRs (H-CDR1, H-CDR2, H-CDR3) respectively having the sequences of SEQ ID NO: 6, 8, 10; and a L-CDR set of L-CDRs (L-CDR1, L-CDR2, L-CDR3) respectively having the sequences of SEQ ID NO: 16, 18, 20;
   an antibody comprising a H-CDR set of H-CDRs (H-CDR1, H-CDR2, H-CDR3) respectively having the sequences of SEQ ID NO: 26, 28, 30; and a L-CDR set of L-CDRs (L-CDR1, L-CDR2, L-CDR3) respectively having the sequences of SEQ ID NO: 36, 38, 40;
   an antibody comprising a H-CDR set of H-CDRs (H-CDR1, H-CDR2, H-CDR3) respectively having the sequences of SEQ ID NO: 46, 48, 50; and a L-CDR set of L-CDRs (L-CDR1, L-CDR2, L-CDR3) respectively having the sequences of SEQ ID NO: 56, 58, 60;
   an antibody comprising a H-CDR set of H-CDRs (H-CDR1, H-CDR2, H-CDR3) respectively having the sequences of SEQ ID NO: 56, 58, 60; and a L-CDR set of L-CDRs (L-CDR1, L-CDR2, L-CDR3) respectively having the sequences of SEQ ID NO: 66, 68, 70;
   an antibody comprising a H-CDR set of H-CDRs (H-CDR1, H-CDR2, H-CDR3) respectively having the sequences of SEQ ID NO: 66, 68, 70; and a L-CDR set of L-CDRs (L-CDR1, L-CDR2, L-CDR3) respectively having the sequences of SEQ ID NO: 76, 78, 80;
   an antibody comprising a H-CDR set of H-CDRs (H-CDR1, H-CDR2, H-CDR3) respectively having the sequences of SEQ ID NO: 86, 88, 90; and a L-CDR set of L-CDRs (L-CDR1, L-CDR2, L-CDR3) respectively having the sequences of SEQ ID NO: 96, 98, 100; and an antibody comprising a H-CDR set of H-CDRs (H-CDR1, H-CDR2, H-CDR3) respectively having the sequences of SEQ ID NO: 126, 128, 130; and a L-CDR set of L-CDRs (L-CDR1, L-CDR2, L-CDR3) respectively having the sequences of SEQ ID NO: 136, 138, 140.

In another embodiment, the anti-IgE antibody or portion thereof is selected from the group consisting of:

an antibody comprising a H-variable domain having the sequence of SEQ ID NO: 4;

an antibody comprising a H-variable domain having the sequence of SEQ ID NO: 24;

an antibody comprising a H-variable domain having the sequence of SEQ ID NO: 44;

an antibody comprising a H-variable domain having the sequence of SEQ ID NO: 64;

an antibody comprising a H-variable domain having the sequence of SEQ ID NO: 84; and an antibody comprising a H-variable domain having the sequence of SEQ ID NO: 124.

In another embodiment, the anti-IgE antibody or portion thereof is selected from the group consisting of:

an antibody comprising an L-variable domain having the sequence of SEQ ID NO: 14;

an antibody comprising an L-variable domain having the sequence of SEQ ID NO: 34;

an antibody comprising an L-variable domain having the sequence of SEQ ID NO: 54;

an antibody comprising an L-variable domain having the sequence of SEQ ID NO: 74;

an antibody comprising an L-variable domain having the sequence of SEQ ID NO: 94; and an antibody comprising an L-variable domain having the sequence of SEQ ID NO: 134.

In another embodiment, the anti-IgE antibody or portion thereof is selected from the group consisting of:

an antibody comprising a H-variable domain having the sequence of SEQ ID NO: 4; and a L-variable domain having the sequence of SEQ ID NO: 14;

an antibody comprising a H-variable domain having the sequence of SEQ ID NO: 24; and a L-variable domain having the sequence of SEQ ID NO: 14;

an antibody comprising a H-variable domain having the sequence of SEQ ID NO: 24; and a L-variable domain having the sequence of SEQ ID NO: 34;

an antibody comprising a H-variable domain having the sequence of SEQ ID NO: 4; and a L-variable domain having the sequence of SEQ ID NO: 34;

an antibody comprising a H-variable domain having the sequence of SEQ ID NO: 44; and a L-variable domain having the sequence of SEQ ID NO: 54;

an antibody comprising a H-variable domain having the sequence of SEQ ID NO: 64; and a L-variable domain having the sequence of SEQ ID NO: 54;

an antibody comprising a H-variable domain having the sequence of SEQ ID NO: 44; and a L-variable domain having the sequence of SEQ ID NO: 74;

an antibody comprising a H-variable domain having the sequence of SEQ ID NO: 64; and a L-variable domain having the sequence of SEQ ID NO: 74;

an antibody comprising a H-variable domain having the sequence of SEQ ID NO: 84; and a L-variable domain having the sequence of SEQ ID NO: 94;

an antibody comprising a H-variable domain having the sequence of SEQ ID NO: 124; and a L-variable domain having the sequence of SEQ ID NO: 94;

an antibody comprising a H-variable domain having the sequence of SEQ ID NO: 84; and a L-variable domain having the sequence of SEQ ID NO: 134; and an antibody comprising a H-variable domain having the sequence of SEQ ID NO: 124; and a L-variable domain having the sequence of SEQ ID NO: 134.

In another embodiment, the anti-IgE antibody or portion thereof is selected from the group consisting of:

an antibody comprising a H-chain having the sequence of SEQ ID NO: 2;

an antibody comprising a H-chain having the sequence of SEQ ID NO: 22;

an antibody comprising a H-chain having the sequence of SEQ ID NO: 42;

an antibody comprising a H-chain having the sequence of SEQ ID NO: 62;

an antibody comprising a H-chain having the sequence of SEQ ID NO: 82; and an antibody comprising a H-chain having the sequence of SEQ ID NO: 122.

In another embodiment, the anti-IgE antibody or portion thereof is selected from the group consisting of:

an antibody comprising an L-chain having the sequence of SEQ ID NO: 12;

an antibody comprising an L-chain having the sequence of SEQ ID NO: 32;

an antibody comprising an L-chain having the sequence of SEQ ID NO: 52;

an antibody comprising an L-chain having the sequence of SEQ ID NO: 72;

an antibody comprising an L-chain having the sequence of SEQ ID NO: 92; and an antibody comprising an L-chain having the sequence of SEQ ID NO: 132.

In another embodiment, the anti-IgE antibody or portion thereof is selected from the group consisting of:

an antibody comprising a H-chain having the sequence of SEQ ID NO: 2; and a L-chain having the sequence of SEQ ID NO: 12;

an antibody comprising a H-chain having the sequence of SEQ ID NO: 22; and a L-chain having the sequence of SEQ ID NO: 12;

an antibody comprising a H-chain having the sequence of SEQ ID NO: 22; and a L-chain having the sequence of SEQ ID NO: 32;

an antibody comprising a H-chain having the sequence of SEQ ID NO: 2; and a L-chain having the sequence of SEQ ID NO: 32;

an antibody comprising a H-chain having the sequence of SEQ ID NO: 42; and a L-chain having the sequence of SEQ ID NO: 52;

an antibody comprising a H-chain having the sequence of SEQ ID NO: 62; and a L-chain having the sequence of SEQ ID NO: 52;

an antibody comprising a H-chain having the sequence of SEQ ID NO:62; and a L-chain having the sequence of SEQ ID NO: 72;

an antibody comprising a H-chain having the sequence of SEQ ID NO: 42; and a L-chain having the sequence of SEQ ID NO: 72;

an antibody comprising a H-chain having the sequence of SEQ ID NO: 82; and a L-chain having the sequence of SEQ ID NO: 92;

an antibody comprising a H-chain having the sequence of SEQ ID NO: 82; and a L-chain having the sequence of SEQ ID NO: 132;

an antibody comprising a H-chain having the sequence of SEQ ID NO: 122; and a L-chain having the sequence of SEQ ID NO: 92; and an antibody comprising a H-chain having the sequence of SEQ ID NO: 122; and a L-chain having the sequence of SEQ ID NO: 132.

In a further embodiment, the anti-IgE antibody or portion thereof is selected from the group consisting of:

an antibody comprising a H-chain sequence encoded by a nucleic acid sequence of SEQ ID NO: 1; and a L-chain sequence encoded by a nucleic acid sequence of SEQ ID NO: 11;

an antibody comprising a H-chain sequence encoded by a nucleic acid sequence of SEQ ID NO: 21; and a L-chain sequence encoded by a nucleic acid sequence of SEQ ID NO: 31;

an antibody comprising a H-chain sequence encoded by a nucleic acid sequence of SEQ ID NO: 41; and a L-chain sequence encoded by a nucleic acid sequence of SEQ ID NO: 51;

an antibody comprising a H-chain sequence encoded by a nucleic acid sequence of SEQ ID NO: 61; and a L-chain sequence encoded by a nucleic acid sequence of SEQ ID NO: 71;

an antibody comprising a H-chain sequence encoded by a nucleic acid sequence of SEQ ID NO: 81; and a L-chain sequence encoded by a nucleic acid sequence of SEQ ID NO: 91; and an antibody comprising a H-chain sequence encoded by a nucleic acid sequence of SEQ ID NO: 121; and a L-chain sequence encoded by a nucleic acid sequence of SEQ ID NO: 131.

In another embodiment, the anti-IgE antibody or portion thereof (to the extent that said portion comprises at least part of a heavy chain constant region) is of the IgG1 or IgG2 subtype.

In another aspect, the present invention provides a variant of an antibody or portion as described above, wherein said variant differs from the antibody or portion by 1, 2, 3, 4, 5, 6, 7, 8, 9 or 10 amino acid substitutions.

In another aspect, the present invention provides a nucleic acid sequence encoding one of the chains of an antibody or portion as described above.

In a further aspect, the present invention provides a vector comprising a nucleic acid sequence encoding one of the chains of an antibody or portion as described above.

In a further aspect, the present invention provides a vector suitable for expressing one of the chains of an antibody or portion as described above.

In another aspect, the present invention provides a cell expressing one of the chains of an antibody or portion as described above.

In another aspect, the present invention provides a method for making an antibody or portion as described above, comprising culturing a cell as described above, and retrieving said antibody or portion thereof.

In one aspect, the antibody or portion thereof is for use as a medicament.

In another aspect, the antibody or portion thereof is for use in the treatment of an IgE-mediated disorder selected from the group consisting of asthma, allergic asthma, allergic rhinitis and food allergies.

In one aspect, the present invention provides a pharmaceutical composition comprising an antibody or portion thereof as described above.

In one embodiment, said pharmaceutical composition is for use in the treatment of an IgE-mediated disorder selected from the group consisting of asthma, allergic asthma, allergic rhinitis and food allergies.

In another aspect, the present invention provides a method for treating an IgE-mediated disorder selected from the group consisting of asthma, allergic asthma, allergic rhinitis and food allergies in a subject in need thereof, comprising administering to said subject a therapeutically effective amount of an antibody or portion thereof as described above.

In another aspect, the present invention provides the use of an antibody or portion thereof as described above in the manufacture of a medicament for treating an IgE-mediated disorder selected from the group consisting of asthma, allergic asthma, allergic rhinitis and food allergies.

In one aspect, the present invention provides a nucleic acid sequence selected from the group consisting of SEQ ID NO: 1, 3, 11, 13, 21, 23, 31, 33, 41, 43, 51, 53, 61, 63, 71, 73, 81, 83, 91, 93, 101, 103, 105, 107, 109, 111, 121, 123, 131 and 133.

In one aspect, the present invention provides an antibody directed against human IgE, wherein said antibody is selected from the group consisting of:

an antibody comprising a H-variable domain having the sequence of SEQ ID NO: 4; and a L-variable domain having the sequence of SEQ ID NO: 14;

an antibody comprising a H-variable domain having the sequence of SEQ ID NO: 24; and a L-variable domain having the sequence of SEQ ID NO: 34;

an antibody comprising a H-variable domain having the sequence of SEQ ID NO: 44; and a L-variable domain having the sequence of SEQ ID NO: 54;

an antibody comprising a H-variable domain having the sequence of SEQ ID NO: 64; and a L-variable domain having the sequence of SEQ ID NO: 74; and an antibody comprising a H-variable domain having the sequence of SEQ ID NO: 84; and a L-variable domain having the sequence of SEQ ID NO: 94; and an antibody comprising a H-variable domain having the sequence of SEQ ID NO: 124; and a L-variable domain having the sequence of SEQ ID NO: 134.

In one aspect, the present invention provides an antibody directed against human IgE, wherein said antibody comprises a H-chain having the sequence of SEQ ID NO: 2; and a L-chain having the sequence of SEQ ID NO: 12.

In another aspect, the present invention provides an antibody directed against human IgE, wherein said antibody comprises a H-chain having the sequence of SEQ ID NO: 22; and a L-chain having the sequence of SEQ ID NO: 32.

In another aspect, the present invention provides an antibody directed against human IgE, wherein said antibody comprises a H-chain having the sequence of SEQ ID NO: 42; and a L-chain having the sequence of SEQ ID NO: 52.

In another aspect, the present invention provides an antibody directed against human IgE, wherein said antibody comprises a H-chain having the sequence of SEQ ID NO: 62; and a L-chain having the sequence of SEQ ID NO: 72.

In another aspect, the present invention provides an antibody directed against human IgE, wherein said antibody comprises a H-chain having the sequence of SEQ ID NO: 82; and a L-chain having the sequence of SEQ ID NO: 92.

In another aspect, the present invention provides an antibody directed against human IgE, wherein said antibody comprises a H-chain having the sequence of SEQ ID NO: 122; and a L-chain having the sequence of SEQ ID NO: 132.

In one aspect, the present invention provides an antibody directed against human IgE, wherein said antibody comprises a H-chain encoded by the insert of ATCC deposit PTA-7977; and a L-chain encoded by the insert of ATCC deposit PTA-7982; wherein said deposits were with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7981; and a L-chain encoded by the insert of ATCC deposit PTA-7980; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7985; and a L-chain encoded by the insert of ATCC deposit PTA-7984; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7983; and a L-chain encoded by the insert of ATCC deposit PTA-7978; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7979; and a L-chain encoded by the insert of ATCC deposit PTA-7986; wherein said deposits were made with the American Type Culture Collection (ATCC), P.O. Box 1549, Manassas, Va. 20108, USA on Nov. 7, 2006, in accordance with the Budapest Treaty.

In one aspect, the above antibody of the invention is for use as a medicament.

In another aspect, the above antibody of the invention is for use in the treatment of an IgE-mediated disorder selected from the group consisting of asthma, allergic asthma, allergic rhinitis and food allergies. In one aspect, the present invention provides a pharmaceutical composition comprising an antibody as described above.

In another aspect, said pharmaceutical composition is for use in the treatment of an IgE-mediated disorder selected from the group consisting of asthma, allergic asthma, allergic rhinitis and food allergies.

In one aspect, the present invention provides a method for treating an IgE-mediated disorder selected from the group consisting of asthma, allergic asthma, allergic rhinitis and food allergies in a subject in need thereof, comprising administering to said subject a therapeutically effective amount of an antibody as described above.

In another aspect, the present invention provides the use of an antibody as described above in the manufacture of a medicament for treating an IgE-mediated disorder selected from the group consisting of asthma, allergic asthma, allergic rhinitis and food allergies.

BRIEF DESCRIPTION OF THE DRAWINGS

FIGS. 1 and 2 show results from an agonist activity assay (RBL-2H3 (FcεR1) cell assay) for exemplary anti-IgE antibodies of the invention;

FIGS. 3 and 4 show results from an agonist activity assay (human blood basophil assay) for exemplary anti-IgE antibodies of the invention; and FIG. 5 shows an epitope binning map for exemplary anti-IgE antibodies of the invention.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

Throughout this specification and claims, the word "comprise," or variations such as "comprises" or "comprising," will be understood to imply the inclusion of a stated integer or group of integers but not the exclusion of any other integer or group of integers.

Antibody-Related Definitions

As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence.

As used herein, the term "ELISA" refers to an enzyme-linked immunosorbent assay. This assay is well known to those of skill in the art. Examples of this assay can be found in Vaughan, T. J. et al., *Nature Biotech.* 14:309-314 (1996), as well as in the Examples of the present application.

The term "surface plasmon resonance", as used herein, refers to an optical phenomenon that allows for the analysis of real-time biospecific interactions by detection of alterations in protein concentrations within a biosensor matrix, for example using the BIAcore™ system (Pharmacia Biosensor AB, Uppsala, Sweden and Piscataway, N.J.). For further descriptions, see Jonsson et al., *Ann. Biol. Clin.* 51:19-26 (1993); Jonsson et al., *Biotechniques* 11:620-627 (1991); Jonsson et al., *J. Mol. Recognit.* 8:125-131 (1995); and Johnsson et al., *Anal. Biochem.* 198:268-277 (1991).

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind an antigen when the $K_D$ is $\leqq 1$ mM, preferably $\leqq 100$ nM. A $K_D$ binding affinity constant can be measured by surface plasmon resonance, for example using the BIAcore™ system as discussed in the below Examples.

The term "$k_{off}$" refers to the dissociation rate constant of a particular antibody-antigen interaction. A dissociation rate constant can be measured by surface plasmon resonance, for example using the BIAcore™ system as discussed in the below Examples.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e. the antibodies compete for binding to the antigen.

One can determine whether an antibody binds to the same epitope or cross competes for binding with an anti-IgE antibody by using methods known in the art. In one embodiment, one allows the anti-IgE antibody of the invention to bind to IgE under saturating conditions and then measures the ability of the test antibody to bind to IgE. If the test antibody is able to bind to IgE at the same time as the reference anti-IgE antibody, then the test antibody binds to a different epitope than the reference anti-IgE antibody. However, if the test antibody is not able to bind to IgE at the same time, then the test antibody binds to the same epitope, an overlapping epitope, or an epitope that is in close proximity to the epitope bound by the anti-IgE antibody of the invention. This experiment can be performed using ELISA, RIA, BIACORE™, or flow cytometry. To test whether an anti-IgE antibody cross-competes with another anti-IgE antibody, one may use the competition method described above in two directions, i.e. determining if the known antibody blocks the test antibody and vice versa. In a preferred embodiment, the experiment is performed using BIACORE™.

A high throughput process for "binning" antibodies based upon their cross-competition is described in International Patent Application No. WO 03/48731.

As used herein, the term "binning" refers to a method to group antibodies based on their antigen binding characteristics. The assignment of bins is somewhat arbitrary, depending on how different are the observed binding patterns for all the antibodies tested. Therefore, bins do not always correlate with epitopes determined by other means and should not be used to define epitopes.

Anti-IgE Antibodies of the Invention

The present invention relates to a human antibody directed against human IgE, or an antigen binding portion thereof.

Unless otherwise stated, as used herein, "IgE" refers to human IgE (human immunoglobulin E).

The term (intact) "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. There are only two types of light chain: A and K. In humans they are similar, but only one type is present in each antibody. Heavy chains are classified as mu, delta, gamma, alpha, or epsilon, and define the antibody's isotype as IgM, IgD, IgG, IgA, and IgE, respectively. See generally, *Fundamental Immunology* Ch. 7 (Paul, W., ed., 2nd ed. Raven Press, N.Y. (1989)).

Each heavy chain (herein sometimes referred to as H-chain or Hc) is comprised of a heavy chain variable domain ($V_H$, or H-variable domain) and a heavy chain constant region ($C_H$). The heavy chain constant region is comprised of three domains, CH1, CH2 and CH3. Each light chain (herein sometimes referred to as L-chain or Lc) is comprised of a light chain variable domain ($V_L$, or L-variable domain) and a light chain constant region. The light chain constant region is comprised of one domain, $C_L$. Within light and heavy chains, the variable and constant regions are joined by a "J" region of about 12 or more amino acids, with the heavy chain also including a "D" region of about 3 or more amino acids. The $V_H$ and $V_L$ regions can be further subdivided into regions of hypervariability, termed "complementarity determining regions" (CDR), interspersed with regions that are more conserved, termed "framework regions" (FR). Each $V_H$ and $V_L$ is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md. (1987 and 1991)), or Chothia & Lesk, *J. Mol. Biol.* 196:901-917 (1987); Chothia et al., *Nature* 342:878-883 (1989).

The variable domains of each heavy/light chain pair ($V_H$ and $V_L$) form the antibody binding site that interacts with an antigen. Thus, an intact IgG antibody, for example, has two binding sites. Except in bifunctional or bispecific antibodies, the two binding sites are the same. The constant regions of the antibodies may mediate the binding of the immunoglobulin to host tissues or factors, including various cells of the immune system (e.g., effector cells) and the first component (Clq) of the classical complement system.

Antibodies must have enough antigen-binding diversity to recognize every possible antigen (many V regions) while maintaining the biological effectiveness of their C regions (few C regions). Ig genes are randomly spliced together from gene segments that allow many V regions to be used with a few C regions. Gene segments encoding Ig H, kappa and lambda chains are found on three different chromosomes. During B cell development, recombinase enzymes remove introns and some exons from the DNA and splice segments into functional Ig genes.

Ig gene segments in mammals are arranged in groups of "variable" (V), "diversity" (D), "joining" (J), and "constant" (C) exons. V kappa (Vκ) segments each encode the first two CDR and three FR of the kappa chain V region, plus a few residues of CDR3. J kappa (Jκ) segments each encode the remainder of CDR3 and the fourth FR. C kappa (Cκ) encodes the complete C region of the kappa light chain. DNA encoding human kappa chain includes approximately 40 functional V kappa (Vκ) segments, five J kappa (Jκ) segments, and one C kappa (Cκ) gene segment, as well as some gene segments which contain stop codons ("pseudogenes"). Human lambda (λ) chain DNA contains approximately 30 functional V lambda (Vλ) segments and four functional sets of J lambda (Jλ) and C lambda (Cλ) segments. A particular J lambda (Jλ) always pairs with its corresponding C lambda (Cλ), unlike J kappa (Jκ) which all pair with the same C kappa (Cκ). DNA for human H chain includes approximately 50 functional $V_H$ segments, 30 $D_H$ segments, and six $J_H$ segments. The first two CDR and three FR of the heavy chain variable domain are encoded by $V_H$. CDR3 is encoded by a few nucleotides of $V_H$, all of $D_H$, and part of $J_H$, while FR4 is encoded by the remainder of the $J_H$ gene segment. There are also individual gene segments in the DNA for each heavy chain domain and membrane region of each isotype, arranged in the order in which they are expressed by B cells.

In various embodiments of the invention, the heavy and light chains of the anti-IgE antibodies may optionally include a signal sequence. The term "signal sequence," also called signal peptide, or leader peptide, refers to a segment of about 15 to 30 amino acids at the N terminus of a protein that enables the protein to be secreted (pass through a cell membrane). The signal sequence is removed as the protein is secreted.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Examples of isolated antibodies include, but not limited to, an anti-IgE antibody that has been affinity purified using IgE, and an anti-IgE antibody that has been synthesized by a cell line in vitro.

As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term also encompasses such antibodies produced recombinantly in non-human cells, which might impart glycosylation not typical of human cells.

These antibodies may be prepared in a variety of ways, as described below. In particular, they are obtainable e.g. from non-human animals bearing human immunoglobulin loci, or a fully human immune system.

The term "antigen-binding portion" of an antibody (or simply "antibody portion"), as used herein, refers to one or more fragments of an antibody that retain the ability to specifically bind to an antigen (e.g., human IgE, or a portion thereof, including epsilon Hc C2-C4 (Cε2-Cε4) and epsilon Hc C3-C4 (Cε3-Cε4) domains. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Also within the invention are antigen-binding molecules comprising a $V_H$ and/or a $V_L$, In the case of a $V_H$, the molecule may also comprise one or more of a CH1, hinge, CH2 or CH3 region. Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al. Structure 2:1121-1123 (1994)).

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al. Human Antibodies and Hybridomas 6:93-101 (1995)) and use of a cysteine residue, a marker peptide and a C-terminal polyhistidine tag to make bivalent and biotinylated scFv molecules (Kipriyanov et al. Mol. Immunol. 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

In one embodiment, the antibody of the invention is a monoclonal antibody. As used herein, the acronym "mAb" refers to a monoclonal antibody, i.e. an antibody synthesized and secreted by an individual clonal population of cells. The clonal population can be a clonal population of immortalized cells. In some embodiments, the immortalized cells in the clonal population are hybrid cells—hybridomas—typically produced by the fusion of individual B lymphocytes from an immunized animal with individual cells from a lymphocytic tumour.

As used herein, a monoclonal antibody that is referred to by number is a monoclonal antibody (mAb) that is obtained from the hybridoma of the same number. For example, monoclonal antibody 6.605.1 is obtained from hybridoma 6.605.1.

In another embodiment, the monoclonal antibody of the invention is a recombinant antibody (see below). The class and subclass of anti-IgE antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

The class of an anti-IgE antibody obtained as described above may be switched with another. In one aspect of the invention, a nucleic acid molecule encoding $V_L$ or $V_H$ is isolated using methods well-known in the art such that it does not include nucleic acid sequences encoding $C_L$ or $C_H$. "Antibody Engineering" (Kontermann & Dubel, Eds., Springer-Verlag, Berlin (2001)). The nucleic acid molecules encoding $V_L$ or $V_H$ are then operatively linked to a nucleic acid sequence encoding a $C_L$ or $C_H$, respectively, from a different class of immunoglobulin molecule. This may be achieved using a vector or nucleic acid molecule that comprises a $C_L$ or $C_H$ chain, as described above. For example, an anti-IgE antibody that was originally IgM may be class switched to an IgG. Further, the class switching may be used to convert one IgG subclass to another, e.g., from IgG1 to IgG2. A preferred method for producing an antibody of the invention comprising a desired isotype comprises the steps of isolating a nucleic acid molecule encoding the heavy chain of an anti-IgE antibody and a nucleic acid molecule encoding the light chain of an anti-IgE antibody, obtaining the variable domain of the heavy chain, ligating the variable domain of the heavy chain with the constant domain of a heavy chain of the desired isotype, expressing the light chain and the ligated heavy chain in a cell, and collecting the anti-IgE antibody with the desired isotype.

The anti-IgE antibody of the invention can be an IgG, an IgM, an IgE, an IgA, or an IgD molecule. In a preferred embodiment, the anti-IgE antibody is an IgG and is an IgG1, IgG2, IgG3, or IgG4 subclass. In another preferred embodiment, the antibody is subclass IgG2.

Examples of isolated antibodies of the invention include, but not limited to, an anti-IgE antibody that has been affinity purified using human IgE, and an anti-IgE antibody that has been synthesized by a cell line in vitro.

Serum Depletion Assay

In one aspect, the present invention provides a human antibody directed against human IgE, or an antigen-binding portion thereof, wherein said antibody has an $IC_{25\ ng/mL}$ (100-5000 ng/mL) of about 0.1-30 µg/mL, wherein the $IC_{25\ ng/mL}$ (100-5000 ng/mL) is defined as the in vitro concentration of antibody required to reduce the free IgE concentration in a serum sample from an initial concentration in the range of about 100-5000 ng/mL to a concentration of about 25 ng/mL. In one embodiment, the antibody or portion thereof has an $IC_{25\ ng/mL}$ (100-5000 ng/mL) of about 0.1-25 µg/mL, preferably 0.1-20 µg/mL, preferably 0.1-17 µg/mL, preferably 0.1-15 µg/mL, preferably 0.1-11 µg/mL, most preferably 0.1-2 µg/mL.

In one embodiment, the antibody or portion thereof has an $IC_{25\ ng/mL}$ (100-1500 ng/mL) of about 1-25 µg/mL, preferably 1-5 µg/mL, preferably 1-2 µg/mL.

More generally, the $IC_{25\ ng/mL}$ (x-y ng/mL) is defined herein as the in vitro concentration of antibody required to reduce the free IgE concentration in a serum sample from an initial concentration in the range of about x-y ng/mL to a concentration of about 25 ng/mL.

In another aspect, the present invention provides a human antibody directed against human IgE, or an antigen-binding portion thereof, wherein said antibody has an $IC_{25\ ng/mL}$ (500-1500 ng/mL) of about 1-25 µg/mL, wherein the $IC_{25\ ng/mL}$ (500-1500 ng/mL) is defined as the in vitro concentration of antibody required to reduce the free IgE concentration in a serum sample from an initial concentration in the range of about 500-1500 ng/mL to a concentration of about 25 ng/mL. In one embodiment, the antibody or portion thereof has an $IC_{25\ ng/mL}$ (500-1500 ng/mL) of about 1-20 µg/mL, preferably 1-15 µg/mL, preferably 1-10 µg/mL, preferably 1-5 µg/mL, most preferably 2 µg/mL.

In another aspect, the present invention provides a human antibody directed against human IgE, or an antigen-binding portion thereof, wherein said antibody has an $IC_{25\ ng/mL}$ (100-500 ng/mL) of about 0.1-15 µg/mL, wherein the $IC_{25\ ng/mL}$ (100-500 ng/mL) is defined as the in vitro concentration of antibody required to reduce the free IgE concentration in a serum sample from an initial concentration in the range of about 100-500 ng/mL to a concentration of about 25 ng/mL. In one embodiment, the antibody or portion thereof has an $IC_{25\ ng/mL}$ (100-500 ng/mL) of about 0.1-10 µg/mL, 0.1-8 µg/mL, preferably 0.1-5 µg/mL, preferably 0.1-4 µg/mL, preferably 0.1-3 µg/mL, preferably 1.2 µg/mL.

In another aspect, the present invention provides a human antibody directed against human IgE, or an antigen-binding portion thereof, wherein said antibody has an $IC_{25\ ng/mL}$ (1500-5000 ng/mL) of about 1-30 µg/mL, wherein the $IC_{25\ ng/mL}$ (1500-5000 ng/mL) is defined as the in vitro concentration of antibody required to reduce the free IgE concentration in a serum sample from an initial concentration in the range of about 1500-5000 ng/mL to a concentration of about 25 ng/mL. In one embodiment, the antibody or portion thereof has an $IC_{25\ ng/mL}$ (1500-5000 ng/mL) of about 1-28 µg/mL, preferably 1-27 µg/mL, preferably 2-26 µg/mL, preferably 2-25 µg/mL.

The $IC_{25\ ng/mL}$ (x-y ng/mL) of a given test-antibody may be determined by a free IgE serum depletion test. The underlying principle is to incubate a serum sample with said test-antibody, to allow binding of serum free IgE to said test-antibody. The amount (fraction) of IgE not bound to said test-antibody can thereafter be detected and measured, e.g. using an ELISA detection assay after removal of the (test-antibody)-IgE complexes previously formed.

Free IgE corresponds to circulating unbound IgE, i.e. IgE not bound to an antibody and not bound to any cell or receptor.

More precisely, the $IC_{25\ ng/mL}$ (x-y ng/mL) can be determined using an assay method comprising the following steps:
a) Providing a human serum sample having an initial free IgE concentration in the range of x-y ng/mL;
b) Providing a test-antibody (test anti-IgE antibody);
c) Preparing an ELISA plate (or any other suitable ELISA solid reagent) using the same test-antibody as the capture reagent coated on said plate;
d) Incubating said serum sample provided in step a) with said test-antibody provided in step b), thus providing an incubation mixture;
e) Incubating the incubation mixture from step d) with the ELISA plate prepared in step c);
f) Washing the ELISA plate of step e);
g) Detecting and measuring the amount of IgE left bound onto said ELISA plate.

Those skilled in the art know how to prepare a serum sample starting from blood samples originating from a human subject. For example, this may involve collecting blood into glass serum tube (e.g. Becton Dickinson cat. No. 366636), allowing to clot for 60 minutes, then centrifuge at 500×g for 10 minutes and collecting serum supernatant. Said human serum sample may be diluted in order to adjust its initial free IgE concentration, for example with the same buffer as being used in ELISA, e.g. 1% BSA/TBS as described in the Examples below. Total IgE concentration can be easily measured using a standard ELISA assay, e.g. using a commercial kit (e.g. IBL or Bethyl market such detection kits). Typically, said initial free IgE concentration is of about 100-5000 ng/mL. In one aspect, said initial free IgE concentration is of about 100-500 ng/mL; or of about 500-1500 ng/mL; or of about 1500-5000 ng/mL. Those skilled in the art also know how to prepare an ELISA plate as provided in step c). This may typically be performed by incubating the desired test-antibody onto suitable well plates (typically, plates wherein the adsorption of the antibody does not interfere with the subsequent desired reaction, e.g. Nunc Maxisorp™ 96-well plates (Fisher Scientific, Cat. No. DIS-971-010P). Said antibody is generally used in solution in a suitable buffer, e.g. TBS. Incubation may last about 10, 12 or 16 hours, generally at around 4° C., to allow suitable coating of the plate, followed by one or several washing steps, e.g. with Tween-TBS buffer. The plate is subsequently blocked, e.g. using 1% BSA-TBS. Blocking can for example be performed for 1 hr at RT, the plate then is washed again (e.g. with Tween-TBS) before use in step d).

The incubation of step d) may be performed for about 10, 12 or 16 hours. The incubation temperature is generally of around 37° C. Incubation conditions typically further include a humidified atmosphere with 5% $CO_2$. Control assays may be used to show that free IgE binds to the capture reagent (ELISA plate of step c)), whereas (test-antibody)-IgE complexes do not.

The incubation of step e) may for example be performed for about 2 h, at RT. Control assays may be used to show that free IgE binds to the capture reagent (ELISA plate of step c)), whereas (test-antibody)-IgE complexes do not.

Washing in step f) may involve one or several washing steps, e.g. with Tween-TBS. This step should ensure that all (test-antibodies)-IgE complexes are removed from the wells on the ELISA plate.

For step g), those skilled in the art may use commercial human IgE standards for calibrating the results. Detection and measurements in step f) can be e.g. performed using a labelled polyclonal anti-IgE antibody. Such polyclonal anti-IgE antibodies are commercially available, especially biotinylated versions. Subsequent detection may then employ a Streptavidin-HRP reagent (also commercially available).

In one embodiment, the anti-IgE antibody or portion thereof according to the invention comprises a H-CDR3 having a sequence selected from the group consisting of SEQ ID NO: 10, 30, 50, 70, 90 and 130.

In one embodiment, the anti-IgE antibody or portion thereof comprises an L-CDR3 having a sequence selected from the group consisting of SEQ ID NO: 20, 40, 60, 80, 100 and 140.

In another embodiment, the anti-IgE antibody or portion is selected from the group consisting of:
an antibody comprising a H-CDR set of H-CDRs (H-CDR1, H-CDR2, H-CDR3) respectively having the sequences of SEQ ID NO: 6, 8, 10;
an antibody comprising a H-CDR set of H-CDRs (H-CDR1, H-CDR2, H-CDR3) respectively having the sequences of SEQ ID NO: 26, 28, 30;
an antibody comprising a H-CDR set of H-CDRs (H-CDR1, H-CDR2, H-CDR3) respectively having the sequences of SEQ ID NO: 46, 48, 50;
an antibody comprising a H-CDR set of H-CDRs (H-CDR1, H-CDR2, H-CDR3) respectively having the sequences of SEQ ID NO: 66, 68, 70;
antibody comprising a H-CDR set of H-CDRs (H-CDR1, H-CDR2, H-CDR3) respectively having the sequences of SEQ ID NO: 86, 88, 90; and
an antibody comprising a H-CDR set of H-CDRs (H-CDR1, H-CDR2, H-CDR3) respectively having the sequences of SEQ ID NO: 126, 128, 130.

In another embodiment, the anti-IgE antibody or portion thereof is selected from the group consisting of:
an antibody comprising an L-CDR set of L-CDRs (L-CDR1, L-CDR2, L-CDR3) respectively having the sequences of SEQ ID NO: 16, 18, 20;
an antibody comprising an L-CDR set of L-CDRs (L-CDR1, L-CDR2, L-CDR3) respectively having the sequences of SEQ ID NO: 36, 38, 40;
an antibody comprising an L-CDR set of L-CDRs (L-CDR1, L-CDR2, L-CDR3) respectively having the sequences of SEQ ID NO: 56, 58, 60;
an antibody comprising an L-CDR set of L-CDRs (L-CDR1, L-CDR2, L-CDR3) respectively having the sequences of SEQ ID NO: 76, 78, 80; and
an antibody comprising an L-CDR set of L-CDRs (L-CDR1, L-CDR2, L-CDR3) respectively having the sequences of SEQ ID NO: 96, 98, 100.
an antibody comprising an L-CDR set of L-CDRs (L-CDR1, L-CDR2, L-CDR3) respectively having the sequences of SEQ ID NO: 136, 138, 140.

In one embodiment, the anti-IgE antibody or portion is selected from the group consisting of:
an antibody comprising an H-CDR3 having the sequence of SEQ ID NO: 10 and an LCDR3 having the sequence of SEQ ID NO: 20;
an antibody comprising an H-CDR3 having the sequence of SEQ ID NO: 30 and an LCDR3 having the sequence of SEQ ID NO: 40;
an antibody comprising an H-CDR3 having the sequence of SEQ ID NO: 50 and an LCDR3 having the sequence of SEQ ID NO: 60;
an antibody comprising an H-CDR3 having the sequence of SEQ ID NO: 70 and an LCDR3 having the sequence of SEQ ID NO: 80;

an antibody comprising an H-CDR3 having the sequence of SEQ ID NO: 90 and an LCDR3 having the sequence of SEQ ID NO: 100;

an antibody comprising an H-CDR3 having the sequence of SEQ ID NO: 130 and an LCDR3 having the sequence of SEQ ID NO: 140

In another embodiment, the anti-IgE antibody or portion thereof is selected from the group consisting of:

an antibody comprising a H-CDR set of H-CDRs (H-CDR1, H-CDR2, H-CDR3) respectively having the sequences of SEQ ID NO: 6, 8, 10; and a L-CDR set of L-CDRs (L-CDR1, L-CDR2, L-CDR3) respectively having the sequences of SEQ ID NO: 16, 18, 20;

an antibody comprising a H-CDR set of H-CDRs (H-CDR1, H-CDR2, H-CDR3) respectively having the sequences of SEQ ID NO: 26, 28, 30; and a L-CDR set of L-CDRs (L-CDR1, L-CDR2, L-CDR3) respectively having the sequences of SEQ ID NO: 36, 38, 40;

an antibody comprising a H-CDR set of H-CDRs (H-CDR1, H-CDR2, H-CDR3) respectively having the sequences of SEQ ID NO: 46, 48, 50; and a L-CDR set of L-CDRs (L-CDR1, L-CDR2, L-CDR3) respectively having the sequences of SEQ ID NO: 56, 58, 60;

an antibody comprising a H-CDR set of H-CDRs (H-CDR1, H-CDR2, H-CDR3) respectively having the sequences of SEQ ID NO: 66, 68, 70; and a L-CDR set of L-CDRs (L-CDR1, L-CDR2, L-CDR3) respectively having the sequences of SEQ ID NO: 76, 78, 80;

an antibody comprising a H-CDR set of H-CDRs (H-CDR1, H-CDR2, H-CDR3) respectively having the sequences of SEQ ID NO: 86, 88, 90; and a L-CDR set of L-CDRs (L-CDR1, L-CDR2, L-CDR3) respectively having the sequences of SEQ ID NO: 96, 98, 100; and an antibody comprising a H-CDR set of H-CDRs (H-CDR1, H-CDR2, H-CDR3) respectively having the sequences of SEQ ID NO: 126, 128, 130; and a L-CDR set of L-CDRs (L-CDR1, L-CDR2, L-CDR3) respectively having the sequences of SEQ ID NO: 136, 138, 140.

In another embodiment, the anti-IgE antibody or portion thereof is selected from the group consisting of:

an antibody comprising a H-variable domain having the sequence of SEQ ID NO: 4;

an antibody comprising a H-variable domain having the sequence of SEQ ID NO: 24;

an antibody comprising a H-variable domain having the sequence of SEQ ID NO: 44;

an antibody comprising a H-variable domain having the sequence of SEQ ID NO: 64;

an antibody comprising a H-variable domain having the sequence of SEQ ID NO: 84; and an antibody comprising a H-variable domain having the sequence of SEQ ID NO: 124.

In another embodiment, the anti-IgE antibody or portion thereof is selected from the group consisting of:

an antibody comprising an L-variable domain having the sequence of SEQ ID NO: 14;

an antibody comprising an L-variable domain having the sequence of SEQ ID NO: 34;

an antibody comprising an L-variable domain having the sequence of SEQ ID NO: 54;

an antibody comprising an L-variable domain having the sequence of SEQ ID NO: 74;

an antibody comprising an L-variable domain having the sequence of SEQ ID NO: 94; and an antibody comprising an L-variable domain having the sequence of SEQ ID NO: 134.

In another embodiment, the anti-IgE antibody or portion thereof is selected from the group consisting of:

an antibody comprising a H-variable domain having the sequence of SEQ ID NO: 4; and a L-variable domain having the sequence of SEQ ID NO: 14;

an antibody comprising a H-variable domain having the sequence of SEQ ID NO: 24; and a L-variable domain having the sequence of SEQ ID NO: 14;

an antibody comprising a H-variable domain having the sequence of SEQ ID NO: 24; and a L-variable domain having the sequence of SEQ ID NO: 34;

an antibody comprising a H-variable domain having the sequence of SEQ ID NO: 4; and a L-variable domain having the sequence of SEQ ID NO: 34;

an antibody comprising a H-variable domain having the sequence of SEQ ID NO: 44; and a L-variable domain having the sequence of SEQ ID NO: 54;

an antibody comprising a H-variable domain having the sequence of SEQ ID NO: 64; and a L-variable domain having the sequence of SEQ ID NO: 54;

an antibody comprising a H-variable domain having the sequence of SEQ ID NO: 44; and a L-variable domain having the sequence of SEQ ID NO: 74;

an antibody comprising a H-variable domain having the sequence of SEQ ID NO: 64; and a L-variable domain having the sequence of SEQ ID NO: 74;

an antibody comprising a H-variable domain having the sequence of SEQ ID NO: 84; and a L-variable domain having the sequence of SEQ ID NO: 94; and an antibody comprising a H-variable domain having the sequence of SEQ ID NO: 124; and a L-variable domain having the sequence of SEQ ID NO: 134.

In another embodiment, the anti-IgE antibody or portion thereof is selected from the group consisting of:

an antibody comprising a H-chain having the sequence of SEQ ID NO: 2;

an antibody comprising a H-chain having the sequence of SEQ ID NO: 22;

an antibody comprising a H-chain having the sequence of SEQ ID NO: 42;

an antibody comprising a H-chain having the sequence of SEQ ID NO: 62;

an antibody comprising a H-chain having the sequence of SEQ ID NO: 82 and;

an antibody comprising a H-chain having the sequence of SEQ ID NO: 122 and;

In another embodiment, the anti-IgE antibody or portion thereof is selected from the group consisting of:

an antibody comprising an L-chain having the sequence of SEQ ID NO: 12;

an antibody comprising an L-chain having the sequence of SEQ ID NO: 32;

an antibody comprising an L-chain having the sequence of SEQ ID NO: 52;

an antibody comprising an L-chain having the sequence of SEQ ID NO: 72;

an antibody comprising an L-chain having the sequence of SEQ ID NO: 92; and an antibody comprising an L-chain having the sequence of SEQ ID NO: 132.

In another embodiment, the anti-IgE antibody or portion is selected from the group consisting of:

an antibody comprising a H-chain having the sequence of SEQ ID NO: 2; and a L-chain having the sequence of SEQ ID NO: 12;

an antibody comprising a H-chain having the sequence of SEQ ID NO: 22; and a L-chain having the sequence of SEQ ID NO: 12;
an antibody comprising a H-chain having the sequence of SEQ ID NO: 22; and a L-chain having the sequence of SEQ ID NO: 32;
an antibody comprising a H-chain having the sequence of SEQ ID NO: 2; and a L-chain having the sequence of SEQ ID NO: 32;
an antibody comprising a H-chain having the sequence of SEQ ID NO: 42; and a L-chain having the sequence of SEQ ID NO: 52;
an antibody comprising a H-chain having the sequence of SEQ ID NO: 62; and a L-chain having the sequence of SEQ ID NO: 52;
an antibody comprising a H-chain having the sequence of SEQ ID NO:62; and a L-chain having the sequence of SEQ ID NO: 72;
an antibody comprising a H-chain having the sequence of SEQ ID NO: 42; and a L-chain having the sequence of SEQ ID NO: 72;
an antibody comprising a H-chain having the sequence of SEQ ID NO: 82; and a L-chain having the sequence of SEQ ID NO: 92;
an antibody comprising a H-chain having the sequence of SEQ ID NO: 82; and a L-chain having the sequence of SEQ ID NO: 132.
an antibody comprising a H-chain having the sequence of SEQ ID NO: 122; and a L-chain having the sequence of SEQ ID NO: 92; and
an antibody comprising a H-chain having the sequence of SEQ ID NO: 122; and a L-chain having the sequence of SEQ ID NO: 132.

In another embodiment, the anti-IgE antibody or portion thereof (to the extent that said portion comprises at least part of a heavy chain constant region) is of the IgG1 or IgG2 subtype.

Exemplary preferred antibodies of the invention include the following antibodies:

mAb 5.396.1 (produced by hybridoma);
recombinant 5.396.1;
5.396.1 Hc-S103N Lc-K61R, also sometimes referred to as 5.396.1 (Hc-S103N Lc-K61R) or as 5.396.1 (S103N/K61R) or as 5.396.1 N/R (i.e. having the same chain sequences as the 5.396.1 mAb, except for the indicated amino acid substitutions in the Heavy Chain Hc and Light Chain Lc);
mAb 6.605.1 (produced by hybridoma);
recombinant 6.605.1;
6.605.1 Hc-H3Q,M13K,D82E Lc-T25A, T53S, also sometimes referred to as 6.605.1 (H3Q,M13K,D82E-T25A, T53S), or as 6.605.1 QKE/AS (i.e. having the same chain sequences as the 6.605.1 mAb, except for the indicated amino acid substitutions in the Heavy Chain Hc and Light Chain Lc);
mAb 5.948.1 (produced by hybridoma);
recombinant 5.948.1;
5.948.1 Hc-H100Y, also sometimes referred to as 5.948.1 H100Y (i.e. having the same chain sequences as the 5.948.1 mAb, except for an indicated amino acid substitutions in the Hc);

These antibodies are described in greater detail in the examples below.

In a further embodiment, the anti-IgE antibody or portion thereof is selected from the group consisting of:

an antibody comprising a H-chain sequence encoded by a nucleic acid sequence of SEQ ID NO: 1; and a L-chain sequence encoded by a nucleic acid sequence of SEQ ID NO: 11;
an antibody comprising a H-chain sequence encoded by a nucleic acid sequence of SEQ ID NO: 21; and a L-chain sequence encoded by a nucleic acid sequence of SEQ ID NO: 31;
an antibody comprising a H-chain sequence encoded by a nucleic acid sequence of SEQ ID NO: 41; and a L-chain sequence encoded by a nucleic acid sequence of SEQ ID NO: 51;
an antibody comprising a H-chain sequence encoded by a nucleic acid sequence of SEQ ID NO: 61; and a L-chain sequence encoded by a nucleic acid sequence of SEQ ID NO: 71;
an antibody comprising a H-chain sequence encoded by a nucleic acid sequence of SEQ ID NO: 81; and a L-chain sequence encoded by a nucleic acid sequence of SEQ ID NO: 91; and
an antibody comprising a H-chain sequence encoded by a nucleic acid sequence of SEQ ID NO: 121; and a L-chain sequence encoded by a nucleic acid sequence of SEQ ID NO: 131.

In one aspect, the present invention provides an antibody directed against human IgE, wherein said antibody comprises a H-chain having the sequence of SEQ ID NO: 2; and a L-chain having the sequence of SEQ ID NO: 12.

In another aspect, the present invention provides an antibody directed against human IgE, wherein said antibody comprises a H-chain having the sequence of SEQ ID NO: 22; and a L-chain having the sequence of SEQ ID NO: 32.

In another aspect, the present invention provides an antibody directed against human IgE, wherein said antibody comprises a H-chain having the sequence of SEQ ID NO: 42; and a L-chain having the sequence of SEQ ID NO: 52.

In another aspect, the present invention provides an antibody directed against human IgE, wherein said antibody comprises a H-chain having the sequence of SEQ ID NO: 62; and a L-chain having the sequence of SEQ ID NO: 72.

In another aspect, the present invention provides an antibody directed against human IgE, wherein said antibody comprises a H-chain having the sequence of SEQ ID NO: 82; and a L-chain having the sequence of SEQ ID NO: 92.

In another aspect, the present invention provides an antibody directed against human IgE, wherein said antibody comprises a H-chain having the sequence of SEQ ID NO: 122; and a L-chain having the sequence of SEQ ID NO: 132.

In one aspect, the present invention provides an antibody directed against human IgE, wherein said antibody comprises a H-chain encoded by the insert of ATCC deposit PTA-7977; and a L-chain encoded by the insert of ATCC deposit PTA-7982; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7981; and a L-chain encoded by the insert of ATCC deposit PTA-7980; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7985; and a L-chain encoded by the insert of ATCC deposit PTA-7984; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7983; and a L-chain encoded by the insert of ATCC deposit PTA-7978; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides an antibody directed against human IgE, wherein said antibody comprises a H-chain encoded by the insert of ATCC deposit PTA-7979; and a L-chain encoded by the insert of ATCC deposit PTA-7986; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides a variant of an antibody or portion thereof as described above, wherein said variant differs from the antibody or portion thereof by 1, 2, 3, 4, 5, 6, 7, 8, 9 or 10 amino acid substitutions.

A further aspect of the present invention is an antibody or antigen-binding portion thereof with at least one of the functional properties described previously, and comprises a $V_H$ domain that is at least 90% identical in amino acid sequence to any one of SEQ ID NOs: 4, 24, 44, 64, 84 or 124. In one embodiment, said $V_H$ domain is at least 91%, at least 93%, at least 95%, at least 97%, at least 99%, or 100% identical in amino acid sequence to any one of SEQ ID NOs: 4, 24, 44, 64, 84 or 124.

A further aspect of the present invention is an antibody or antigen-binding portion thereof with at least one of the functional properties described previously, and comprises a $V_L$ domain that is at least 90% identical in amino acid sequence to any one of SEQ ID NOs: 14, 34, 54, 74, 94 or 134. In one embodiment, said $V_H$ domain is at least 91%, at least 93%, at least 95%, at least 97%, at least 99%, or 100% identical in amino acid sequence to any one of SEQ ID NOs: 14, 34, 54, 74, 94 or 134.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997); herein incorporated by reference.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)).

According to the invention, one type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical.

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues.

Another type of amino acid substitution that may be made in one of the variants according to the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g. Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., *Science* 256:1443-45 (1992). A "moderately conservative" replacement is any change having a nonnegative value in the PAM250 log-likelihood matrix.

In certain embodiments, amino acid substitutions to an antibody or antigen-binding portion of the invention are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to human IgE. Analogs can include various substitutions to the normally-occurring peptide sequence. For example, single or multiple amino acid substitutions, preferably conservative amino acid substitutions, may be made in the normally-occurring sequence, for example in the portion of the polypeptide outside the domain(s) forming intermolecular contacts. Amino acid substitutions can also be made in the domain(s) that form intermolecular contacts that can improve the activity of the polypeptide. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991).

In another aspect of the invention, the antibody may be deimmunized to reduce its immunogenicity using the techniques described in, e.g., PCT Publication WO98/52976 and WO00/34317.

In another embodiment, a fusion antibody or immunoadhesin may be made that comprises all or a portion of an anti-IgE antibody of the invention linked to another polypeptide. In a preferred embodiment, only the variable domains of the anti-IgE antibody are linked to the polypeptide. In another preferred embodiment, the $V_H$ domain of an anti-IgE antibody is linked to a first polypeptide, while the $V_L$ domain of an anti-IgE antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$- and $V_L$-encoding DNA fragments are operatively linked to another fragment encoding a flexible linker, e.g., encoding the amino acid sequence (Gly$_4$-Ser)$_3$ (SEQ ID NO: 174), such that the $V_H$ and $V_L$ sequences can be expressed as a contiguous single-chain protein, with the $V_L$ and $V_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to human IgE and to another molecule.

In other embodiments, other modified antibodies may be prepared using anti-IgE antibody encoding nucleic acid molecules. For instance, "Kappa bodies" (Ill et al., *Protein Eng.* 10: 949-57 (1997)), "Minibodies" (Martin et al., *EMBO J.* 13: 5303-9 (1994)), "Diabodies" (Holliger et al., *Proc. Natl. Acad. Sci. USA* 90: 6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

In certain embodiments, the antibodies of the invention may be present in a neutral form (including zwitter ionic forms) or as a positively or negatively-charged species. In some embodiments, the antibodies may be complexed with a counterion to form a pharmaceutically acceptable salt.

The terms "pharmaceutically acceptable salt" refer to a complex comprising one or more antibodies and one or more counterions, where the counterions are derived from pharmaceutically acceptable inorganic and organic acids and bases.

Pharmaceutically acceptable inorganic bases include metallic ions. More preferred metallic ions include, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic salts, manganous, potassium, rubidium, sodium, and zinc, and in their usual valences.

Pharmaceutically acceptable acid addition salts of the antibodies of the present invention can be prepared from the following acids, including, without limitation formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl)glycine, N-(2-hydroxyethyl)piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino)ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

An anti-IgE antibody or antigen-binding portion of the invention can be derivatized or linked to another molecule (e.g., another peptide or protein). In general, the antibodies or portion thereof are derivatized such that the IgE binding, in particular the binding to free IgE is not affected adversely by the derivatization or labeling. Accordingly, the antibodies and antibody portions of the invention are intended to include both intact and modified forms of the human anti-IgE antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Il.

An anti-IgE antibody can also be derivatized with a chemical group such as polyethylene glycol (PEG), a methyl or ethyl group, or a carbohydrate group. These groups are useful to improve the biological characteristics of the antibody, e.g., to increase serum half-life.

An antibody according to the present invention may also be labeled. As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

Nucleic Acids, Vectors and Cells

The present invention also encompasses nucleic acid molecules and sequences encoding anti-IgE antibodies or an antigen-binding fragment thereof. In some embodiments, different nucleic acid molecules encode a heavy chain and a light chain of an anti-IgE immunoglobulin. In other embodiments, the same nucleic acid molecule encodes a heavy chain and a light chain of an anti-IgE immunoglobulin.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric, possibly isolated, form of nucleotides of at least 10 bases in length, either ribonucleotides or deoxynucleotides or a modified form of either type of nucleotide. The term includes single and double stranded forms.

In one aspect, the present invention provides a nucleic acid sequence encoding one of the chains of an antibody or portion thereof as described above.

In one aspect, the present invention provides a nucleic acid sequence selected from the group consisting of SEQ ID NO: 1, 3, 11, 13, 21, 23, 31, 33, 41, 43, 51, 53, 61, 63, 71, 73, 81, 83, 91, 93, 101, 103, 105, 107, 109, 111, 121, 123, 131 and 133.

Nucleic acid molecules of the invention include nucleic acids that hybridize under highly stringent conditions, such as those described above, or that are at least 70%, 75%, 80%, 85%, 90%, 95%, 97%, 98% or 99% identical to one or more of the above-recited nucleic acid sequences or to a nucleic acid encoding the amino acid sequence any of the provided $V_H$ or $V_L$ sequences.

In one embodiment, said nucleic acid sequence encodes one of the chains of an antibody directed against human IgE, wherein said antibody is selected from the group consisting of:

an antibody comprising a H-variable domain having the sequence of SEQ ID NO: 4; and a L-variable domain having the sequence of SEQ ID NO: 14;

an antibody comprising a H-variable domain having the sequence of SEQ ID NO: 24; and a L-variable domain having the sequence of SEQ ID NO: 34;

an antibody comprising a H-variable domain having the sequence of SEQ ID NO: 44; and a L-variable domain having the sequence of SEQ ID NO: 54;

an antibody comprising a H-variable domain having the sequence of SEQ ID NO: 64; and a L-variable domain having the sequence of SEQ ID NO: 74;

an antibody comprising a H-variable domain having the sequence of SEQ ID NO: 84; and a L-variable domain having the sequence of SEQ ID NO: 94; and an antibody comprising a H-variable domain having the sequence of SEQ ID NO: 124; and a L-variable domain having the sequence of SEQ ID NO:134.

In one aspect, the present invention provides a nucleic acid sequence which has the sequence of the insert of ATCC deposit PTA-7977; and a L-chain encoded by the insert of ATCC deposit PTA-7982; wherein said deposits were made with the American Type Culture Collection (ATCC), P.O. Box 1549, Manassas, Va. 20108, USA on Nov. 7, 2006, in accordance with the Budapest Treaty.

In another aspect, the present invention a nucleic acid sequence which is the insert of ATCC deposit PTA-7981; and a L-chain encoded by the insert of ATCC deposit PTA-7980; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides a nucleic acid sequence which is the insert of ATCC deposit PTA-7985; and a L-chain encoded by the insert of ATCC deposit PTA-7984; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides a nucleic acid sequence which has the sequence of the insert of ATCC deposit PTA-7983; and a L-chain encoded by the insert of ATCC deposit PTA-7978; wherein said deposits were made with the American Type Culture Collection (ATCC), P.O. Box 1549, Manassas, Va. 20108, USA on Nov. 7, 2006, in accordance with the Budapest Treaty.

In another aspect, the present invention provides a nucleic acid sequence which has the sequence of the insert of ATCC deposit PTA-7979; and a L-chain encoded by the insert of ATCC deposit PTA-7986; wherein said deposits were made with the American Type Culture Collection (ATCC), P.O. Box 1549, Manassas, Va. 20108, USA on Nov. 7, 2006, in accordance with the Budapest Treaty.

In a further aspect, the present invention provides a vector comprising a nucleic acid sequence encoding one of the chains of an antibody or portion thereof as described above.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132:185-219 (2000); Pearson, Methods Enzymol. 266:227-258 (1996); Pearson, J. Mol. Biol. 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In a further aspect, the present invention provides a vector suitable for expressing one of the chains of an antibody or portion thereof as described above.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The invention provides vectors comprising nucleic acid molecules that encode the heavy chain of an anti-IgE antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

A nucleic acid molecule encoding the heavy or light chain of an anti-IgE antibody or portions thereof can be isolated from any source that produces such antibody. In various embodiments, the nucleic acid molecules are isolated from a B cell that expresses an anti-IgE antibody isolated from an animal immunized with a human IgE antigen, or from an immortalized cell produced from such a B cell. Methods of isolating nucleic acids encoding an antibody are well-known in the art. See, e.g., Sambrook J. & Russell D. *Molecular Cloning: A Laboratory Manual,* 3rd ed., Cold Spring Harbor Laboratory Press, Cold Spring Harbor, N.Y. (2000). mRNA may be isolated and used to produce cDNA for use in the polymerase chain reaction (PCR) or cDNA cloning of antibody genes. In a preferred embodiment, the nucleic acid molecule is isolated from a hybridoma that has as one of its fusion partners a cell from a non-human transgenic animal, said cell producing a human immunoglobulin. In an even more preferred embodiment, the cell producing human immunoglobulin is isolated from a XenoMouse® animal (see below).

In some embodiments, a nucleic acid encoding a heavy chain of an anti-IgE antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-IgE antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and/or light ($V_L$) chains may be "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See e.g. Kabat et al., *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-IgE antibody isolated.

The nucleic acid molecules may be used to recombinantly express large quantities of anti-IgE antibodies. The nucleic acid molecules also may be used to produce chimeric antibodies, bispecific antibodies, single chain antibodies, immunoadhesins, diabodies, mutated antibodies and antibody derivatives, as described further below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-IgE antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of antibodies or fragments thereof of the invention as described herein.

In another embodiment, the nucleic acid molecules and vectors may be used to make mutated anti-IgE antibodies. The antibodies may be mutated in the variable domains of the heavy and/or light chains, e.g., to alter a binding property of the antibody. For example, a mutation may be made in one or more of the CDR regions to increase or decrease the $K_D$ of the anti-IgE antibody, to increase or decrease $k_{off}$, or to alter the binding specificity of the antibody. Techniques in site-directed mutagenesis are well-known in the art. See e.g. Sambrook et al. and Ausubel et al., supra. In another embodiment, one or more mutations are made at an amino acid residue that is known to be changed compared to the germline in a monoclonal antibody of the invention. The mutations may be made in a CDR region or framework region of a variable domain, or in a constant domain. In a preferred embodiment, the mutations are made in a variable domain. In some embodiments, one or more mutations are made at an amino acid residue that is known to be changed compared to the germline in a CDR region or framework region of a variable domain of an antibody or fragment thereof of the invention.

In another embodiment, the framework region is mutated so that the resulting framework region(s) have the amino acid sequence of the corresponding germline gene. A mutation may be made in a framework region or constant domain to increase the half-life of the anti-IgE antibody. See e.g. PCT Publication WO 00/09560. A mutation in a framework region or constant domain also can be made to alter the immunogenicity of the antibody, to provide a site for covalent or non-covalent binding to another molecule. According to the invention, a single antibody may have mutations in any one or more of the CDRs or framework regions of the variable domain or in the constant domain.

In some embodiments, the anti-IgE antibodies of the invention or antigen-binding portions are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants is known in the art. See e.g. U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Methods of Producing Antibodies and Antibody Producing Cell Lines

In some embodiments, human antibodies are produced by immunizing a non-human, transgenic animal comprising within its genome some or all of human immunoglobulin heavy chain and light chain loci with a human IgE antigen. In a preferred embodiment, the non-human animal is a XenoMouse® animal. (Abgenix, Inc./Amgen, Inc.—Fremont, Calif.).

XenoMouse® mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-IgE antibodies from non-human, non-mouse animals by immunizing non-human transgenic animals that comprise human immunoglobulin loci with an IgE antigen. One can produce such animals using the methods described in the above-cited documents. The methods disclosed in these documents can be modified as described in U.S. Pat. No. 5,994,619. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. U.S. Pat. No. 5,994,619 also describes methods of producing transgenic animals that are capable of transmitting the heterologous DNA to their progeny. In preferred embodiments of the current invention, the non-human animals are mammals, particularly rats, sheep, pigs, goats, cattle, horses or chickens.

XenoMouse® mice produce an adult-like human repertoire of fully human antibodies and generate antigen-specific human antibodies. In some embodiments, the XenoMouse® mice contain approximately 80% of the human antibody V gene repertoire through introduction of megabase sized, germline configuration fragments of the human heavy chain loci and kappa light chain loci in yeast artificial chromosome (YAC). In other embodiments, XenoMouse® mice further contain approximately all of the human lambda light chain locus. See Mendez et al., *Nature Genetics* 15:146-156 (1997), Green and Jakobovits, *J. Exp. Med.* 188:483-495 (1998), and WO 98/24893.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See e.g. Harlow and Lane, supra, and U.S. Pat. No. 5,994,619. In a preferred embodiment, the human IgE antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks. Example 2 exemplifies a method for producing anti-IgE monoclonal antibodies in XenoMouse® mice.

After immunization of an animal with an IgE antigen, antibodies and/or antibody-producing cells can be obtained from the animal. In some embodiments, anti-IgE antibody-containing serum is obtained from the animal by bleeding or sacrificing the animal. The serum may be used as it is obtained from the animal, an immunoglobulin fraction may be obtained from the serum, or the anti-IgE antibodies may be purified from the serum.

In some embodiments, antibody-producing cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using IgE, or a portion thereof. In a preferred embodiment, the initial screening is performed using an enzyme-linked immunoassay (ELISA) or a radioimmunoassay. An example of ELISA screening is provided in WO 00/37504.

Anti-IgE antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the immunized animal is a non-human animal that expresses human immunoglobulin genes and the splenic B cells are fused to a myeloma cell line from the same species as the non-human animal. In a more preferred embodiment, the immunized animal is a XenoMouse® mouse and the myeloma cell line is a non-secretory mouse myeloma. In an even more preferred embodiment, the myeloma cell line is P3-X63-Ag8.653 (American Type Culture Collection). See e.g. Examples below. Thus, in one embodiment, the invention provides methods for producing a cell line that produces a human monoclonal antibody or a fragment thereof directed against IgE comprising (a) immunizing a non-human transgenic animal described herein with IgE, a portion of IgE or a cell or tissue expressing IgE; (b) allowing the transgenic animal to mount an immune response to IgE; (c) isolating antibody-producing cells from the transgenic animal; (d) immortalizing the antibody-producing cells; (e) creating individual monoclonal populations of the immortalized antibody-producing cells; and (f) screening the immortalized antibody-producing cells to identify an antibody directed against IgE.

In another aspect, the invention provides a cell line that produces a human anti-IgE antibody. In some embodiments the cell line is a hybridoma cell line. In some embodiments, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In another embodiment, a transgenic animal is immunized with an IgE antigen, primary cells, e.g., spleen or peripheral blood B cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable domain sequences, e.g., degenerate primers that recognize most or all of the FR1 regions of human heavy and light chain variable domain genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and κ or λ constant domains. See Babcook, J. S. et al., *Proc. Natl. Acad. Sci. USA* 93:7843-48, 1996. Anti-IgE antibodies may then be identified and isolated as described herein.

Phage Display Libraries

The invention provides a method for producing an anti-IgE antibody or antigen-binding portion thereof comprising the steps of synthesizing a library of human antibodies on phage, screening the library with IgE or an antibody-binding portion thereof, isolating phage that bind IgE, and obtaining the antibody from the phage. By way of example, one method for preparing the library of antibodies for use in phage display techniques comprises the steps of immunizing a non-human animal comprising human immunoglobulin loci with IgE or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-IgE antibodies of the invention may be obtained in this way.

Recombinant human anti-IgE antibodies of the invention can be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991), all incorporated herein by reference.

In one embodiment, to isolate and produce human anti-IgE antibodies with the desired characteristics, a human anti-IgE antibody as described herein is first used to select human heavy and light chain sequences having similar binding activity toward IgE, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty et al., *Nature* 348:552-554 (1990); and Griffiths et al., *EMBO J.* 12:725-734 (1993), all incorporated herein by reference. The scFv antibody libraries preferably are screened using human IgE as the antigen.

Once initial human $V_L$ and $V_H$ domains are selected, "mix and match" experiments are performed, in which different pairs of the initially selected $V_L$ and $V_H$ segments are screened for IgE binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to IgE.

Following screening and isolation of an anti-IgE antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Non-Hybridoma Host Cells and Methods of Recombinantly Producing Protein

In one aspect, the present invention provides recombinant host cells allowing the recombinant expression of the antibodies of the invention or portions thereof. Antibodies produced by such recombinant expression in such recombinant host cells are referred to herein as "recombinant antibodies". The present invention also provides progeny cells of such host cells, and antibodies produced by same.

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Such cell may comprise a vector according to the invention as described above.

In another aspect, the present invention provides a method for making an antibody or portion thereof as described above. According to one embodiment, said method comprises culturing a cell transfected or transformed with a vector as described above, and retrieving said antibody or portion thereof.

Nucleic acid molecules encoding anti-IgE antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana*, *Arabidopsis*, duckweed, corn, wheat, potato, etc. Bacterial host cells include *E. coli* and *Streptomyces* species. Yeast host cells include *Schizosaccharomyces pombe*, *Saccharomyces cerevisiae* and *Pichia pastoris*.

Further, expression of antibodies of the invention or portions thereof from production cell lines can be enhanced using a number of known techniques. For example, the glutamine synthetase gene expression system (the GS system) is a common approach for enhancing expression under certain conditions. The GS system is discussed in whole or part in connection with EP patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein are part of the instant invention, regardless of the glycosylation state of the antibodies, and more generally, regardless of the presence or absence of post-translational modification(s).

Transgenic Animals and Plants

Anti-IgE antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-IgE antibodies can be produced in, and recovered from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized with human IgE or an immunogenic portion thereof, as described above. Methods for making antibodies in plants are described, e.g., in U.S. Pat. Nos. 6,046,037 and 5,959,177.

In some embodiments, non-human transgenic animals or plants are produced by introducing one or more nucleic acid molecules encoding an anti-IgE antibody of the invention into the animal or plant by standard transgenic techniques. See Hogan and U.S. Pat. No. 6,417,429, supra. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., *Manipulating the Mouse Embryo: A Laboratory Manual* 2$^{nd}$ ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999). In some embodiments, the transgenic non-human animals have a targeted disruption and replacement by a targeting construct that encodes a heavy chain and/or a light chain of interest. In a preferred embodiment, the transgenic animals comprise and express nucleic acid molecules encoding heavy and light chains that specifically bind to human IgE. The anti-IgE antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Pharmaceutical Compositions, Method for Treating Asthma and Other IgE-Mediated Disorders In one aspect, the antibody or portion thereof according to the invention is for use as a medicament.

In another aspect, the antibody or portion thereof according to the invention is for use in the treatment of asthma, in particular allergic asthma. As described above, asthma and allergic asthma are well defined in the art. They are chronic inflammatory disorders of the airways, typically involving symptoms such as wheezing, breathlessness, chest tightness, and coughing.

In another aspect, the antibody or portion thereof according to the invention is for use in the treatment of other IgE-mediated disorders, including allergic rhinitis and food allergies, including peanut allergy.

Allergic rhinitis generally involves a collection of symptoms, including inflammatory symptoms, predominantly in the nose, sinuses and eyes, which occur after exposure to airborne particles. Symptoms include sneezing; nasal obstruction; runny nose (and occasionally nosebleeds); coughing; headache; itching nose, mouth, eyes, throat, skin, or any area exposed to the allergen; impaired smell (and thus sensitivity to flavours); stuffy nose (nasal congestion); conjunctivitis; watering eyes; sore throat; and wheezing.

Allergic rhinitis may be perennial and/or seasonal. Perennial allergic rhinitis is allergic rhinitis that lasts throughout the year. It is typically caused by continuous exposure to allergens such as animal dander, indoor mould spores, or house dust mites. Seasonal allergic rhinitis is allergic rhinitis that occurs only during certain times of the year. It is commonly caused by allergies to tree, grass, and weed pollen that are produced seasonally.

A food allergy is an exaggerated immune response triggered by eggs, peanuts, milk, or some other specific food. Any food can cause an allergic reaction, but a few foods are the main culprits. In children, the most common food allergies are to eggs, peanuts, milk, soy, tree nuts, wheat, shellfish (shrimp, crab, lobster, snails, clams). In older children and adults, the most common food allergies are: peanuts, tree nuts, shellfish, fish. The symptoms may be confined mainly to the stomach and intestines, or may involve many parts of the body after the food is digested or absorbed. Symptoms may include: scratchy throat, anaphylaxis (a severe, whole-body allergic reaction that can result in death); abdominal pain; diarrhoea; nausea; vomiting; stomach cramps; itching of the mouth, throat, eyes, skin, or any area; hives; angioedema (swelling, especially of the eyelids, face, lips, and tongue); light-headedness or fainting; nasal congestion; runny nose; shortness of breath; wheezing; difficulty swallowing; oral allergy syndrome. The oral allergy syndrome generally comprises itching lips, tongue, and throat, and sometimes swollen lips.

In another aspect, the antibody or portion thereof according to the invention is for use in the treatment of other IgE-mediated disorders, such as conjunctivitis, atopic dermatitis, anaphylaxis, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, ulcerative colitis, indeterminate colitis and infectious colitis), urticaria, psoriasis.

In one aspect, the present invention provides a pharmaceutical composition comprising an antibody or portion thereof as described above.

The antibodies of the invention or portions thereof may be administered alone or in combination with one or more other antibodies of the invention or in combination with one or more other drugs (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with", referring to the antibodies of the invention and one or more other therapeutic agents, is intended to mean, and does refer to and include the following:

simultaneous administration of such combination of antibody (antibodies) of the invention and therapeutic agent(s) to a patient in need of treatment, when such components are formulated together into a single dosage form which releases said components at substantially the same time to said patient, substantially simultaneous administration of such combination of antibody (antibodies) of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination of antibody (antibodies) of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of antibody (antibodies) of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

In one aspect, the antibodies of the invention may be co-administered or formulated with another medication/drug for the treatment of asthma. For example, the antibodies of the invention may be co-administered or co-formulated with one or more selected from the group consisting of steroids, including corticosteroids (inhaled, oral); bronchodilators (such as long-acting beta-2 agonists; short-acting beta-2 agonists); other anti-IgE agents, such as an IgE vaccine; leukotriene antagonists/inhibitors; methylxanthines; antibodies directed against interleukins involved in airway inflammation, e.g. monoclonal antibodies directed against IL-4 or IL-13 or TNF; cromolyns, such as cromolyn sodium; nedocromil sodium; anticholerginics and PDE inhibitors.

In another aspect, the antibodies of the invention may be administered or formulated in combination with at least one of an antihistamine agent, a non-steroidal anti-inflammatory drug, a decongestant, a cough suppressant and an analgesic.

Generally, the antibodies of the invention or portions thereof are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present invention and methods for their preparation will be readily apparent to those skilled in the art. Such compositions and methods for their preparation may be found, for example, in *Remington's Pharmaceutical Sciences*, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-IgE antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 1 mg/mL to about 200 mg/mL of an antibody of the invention, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antibody of the invention per actuation and the actuation volume may for example vary from 1 µL to 100 µL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

In one aspect, said pharmaceutical composition is for use in the treatment of asthma, including allergic asthma.

In another aspect, said pharmaceutical composition is for use in the treatment of other IgE-mediated disorders, including allergic rhinitis, food allergies (such as peanut allergy), conjunctivitis, atopic dermatitis, anaphylaxis, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, ulcerative colitis, indeterminate colitis and infectious colitis), urticaria, psoriasis.

In another aspect, the present invention provides a method for treating asthma, in particular allergic asthma, in a subject in need thereof, comprising administering to said subject a therapeutically effective amount of an antibody or portion thereof as described above.

In another aspect, the present invention provides a method for treating IgE-mediated disorders in a subject in need thereof, comprising administering to said subject a therapeutically effective amount of an antibody or portion thereof as described above.

Said IgE-mediated disorder may be selected from the group consisting of allergic rhinitis, food allergies (such as peanut allergy), conjunctivitis, atopic dermatitis, anaphylaxis, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, ulcerative colitis, indeterminate colitis and infectious colitis), urticaria, psoriasis.

In yet another aspect, the present invention provides a method for treating a parasite infection in a subject in need thereof, wherein said parasite infection is associated with elevated IgE levels. In one aspect, said method comprises administering an amount of an antibody of the invention to said subject, wherein said amount is sufficient to reduce the subject's IgE levels in such a way that they are undetectable during the course of treatment.

In yet another aspect, the present invention provides the use of an antibody or portion thereof as described above in the manufacture of a medicament for treating an IgE-mediated disorder selected from the group consisting of asthma, allergic asthma, allergic rhinitis and food allergies.

In yet another aspect, the present invention provides the use of an antibody or portion thereof as described above in the manufacture of a medicament for treating an IgE-mediated disorder selected from the group consisting of conjunctivitis, atopic dermatitis, anaphylaxis, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, ulcerative colitis, indeterminate colitis and infectious colitis), urticaria, psoriasis.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

In one aspect, the subject is a mammal, preferably a human subject. Said subject may be either male or female, of any age.

"Therapeutically effective amount" refers to that amount of the therapeutic agent being administered which will relieve to some extent one or more of the symptoms of the disorder being treated. In reference to the treatment of asthma, a therapeutically effective amount refers to that amount which alleviates at least one of the following symptoms: shortness of breath, chest tightness, wheezing, coughing.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of the antibodies or antibody portion of the invention is typically in the range 0.5-1200 mg per patient, depending, of course, on the mode of administration. For example, an intravenous monthly dose may require about 1-1000 mg/patient. The total monthly dose may be administered in single or divided doses and may, at the physician's discretion, fall outside of the typical range given herein.

An exemplary, non-limiting range for a therapeutically or prophylactically effective amount of an antibody or antibody portion of the invention is 1-1000 mg/patient/month. In one embodiment, the antibody or portion thereof of the invention may be administered at about 1-200 or 1-150 mg/patient/month.

In order that this invention may be better understood, the following examples are set forth. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Immunogens

The below sequence is the epsilon heavy chain C2-C4 domain from human IgE used as the immunogen for Fusion 6, (giving rise to clones whose number starts with a 6, including 6.605.1):

```
PTVKILQSSCDGGGHFPPTIQLLCLVSGYTPGTINITWLEDGQVMDVDLSTASTTQEGELASTQSELTLSQ

KHWLSDRTYTCQVTYQGHTFEDSTKKCADSNPRGVSAYLSRPSPFDLFIRKSPTITCLVVDLAPSKGTVN

LTWSRASGKPVNHSTRKEEKQRNGTLTVTSTLPVGTRDWIEGETYQCRVTHPHLPRALMRSTTKTSGPR

AAPEVYAFATPEWPGSRDKRTLACLIQNFMPEDISVQWLHNEVQLPDARHSTTQPRKTKGSGFFVFSRL

EVTRAEWEQKDEFICRAVHEAASPSQTVQRAVSVNPGK
```

The C3-C4 sequence below is the predicted sequence of the epsilon heavy chain C3-C4 domain from human IgE used as the immunogen for Fusion 5 (giving rise to clones whose number starts with a 5, including 5.396.1 and 5.948.1):

```
CADSNPRGVSAYLSRPSPFDLFIRKSPTITCLVVDLAPSKGTVNLTWSRASGKPVNHSTRKEEKQRNGTL

TVTSTLPVGTRDWIEGETYQCRVTHPHLPRALMRSTTKTSGPRAAPEVYAFATPEWPGSRDKRTLACLI

QNFMPEDISVQWLHNEVQLPDARHSTTQPRKTKGSGFFVFSRLEVTRAEWEQKDEFICRAVHEAASPS

QTVQRAVSVNPGK
```

Example 2

Immunization and Hybridoma Generation

Eight to ten week old XenoMouse® mice were immunized in their hind footpads with 10 µg/mouse of antigen. This dose was repeated six to eight times over a three to five week period. Three or four days before fusion, the mice were given a final injection of the immunogen in PBS. The spleen and lymph node lymphocytes from immunized mice were fused with the non-secretory myeloma P3-X63-Ag8.653 cell line (ATCC Cat. No. CRL 1580) via electro cell fusion, and these fused cells were subjected to HA-DMEM selection as previously described (DMEM, 15% FBS, 1% 200 mM L-glutamine, 1% 100× Non-essential amino acid 1% 100× Pen/Strep, 10 U/ml IL-6, 1 vial/liter OPI media supplement, plus 0.5×HA (Azaserine-Hypoxanthine, Sigma, Cat. # A9666)). A panel of hybridomas was recovered that all secrete IgE-specific human IgG2 antibodies.

ELISA assay was used to detect antibody binding. Immunogen was coated to the 96-well Immulon microtiter plate (NUNC-Immuno™ plate MaxiSorp™ surface, Nalge Nunc International, Cat. No. 439-454) at 4 µg/mL in 50 mM sodium bicarbonate buffer for overnight at 4° C. Plates were washed, and then blocked with PBS with the addition of 0.1% Tween-20 and 0.5% bovine serum albumin. Antibodies were added to the blocked ELISA plates, incubated for 1 hour, and washed with PBS with Tween-20. The binding was detected by anti-human IgG-horseradish peroxidase (Pierce, Catalog No. 31420) followed by the addition of ABTS (Pierce, Catalog No. 37615). Colorimetric measurements were performed at 405 nm in a micro-plate reader (SpectraMax Plus 384, Molecular Devices).

Hybridomas selected for further study were single-cell cloned by limiting dilution.

Example 3

Sequence of Anti-IgE Antibodies of the Invention

Full-length Anti-IgE antibodies were cloned and sequence verified from hybridomas as follows:

Poly(A)+ mRNA was isolated using an RNeasy Mini Kit (Qiagen, Cat# 74104) and cDNA synthesized from the mRNA with the SuperScript III First-Strand Synthesis System for RT-PCR (Invitrogen, Cat# 18080051) using oligo (dT) priming. The oligo (dT) primed cDNA for clone 5.396.1, 6.605.1 and 5.948.1 were amplified using gene specific primers listed in Table 1, 2 and 3, respectively. Amplification was achieved using Taq DNA Polymerase (Roche Cat#1146173) and a PTC-200 DNA Engine (MJ Research) with cycling as follows: For heavy chain 2'@94° C.; 5× (30"@94° C., 30"@50° C., 2'30"@68° C.); 25× (30"@94° C., 30"@68° C., 2'30"@68° C.); 5'@68° C., for light chain 2'@94° C.; 5× (30"@94° C., 30"@50° C., 1'30"@68° C.); 25× (30"@94° C., 30"@68° C., 1'30"@68° C.); 5'@68° C. PCR amplicons were cloned into the pCR2.1 TOPO (Invitrogen, Cat# 450641) and transformed into DH5α chemically competent cells (Invitrogen Cat# 18258012) using the standard protocol. Clones were sequence verified using Grills 16th BDTv3.1/dGTP chemistry (Applied Biosystems Inc) and a 3730xl DNA Analyzer (Applied Biosystems Inc). All sequences were analyzed by alignments to the 'V BASE sequence directory' (Tomlinson, et al, *J. Mol. Biol.*, 227, 776-798 (1992); *Hum. Mol. Genet.*, 3, 853-860 (1994); *EMBO J.*, 14, 4628-4638 (1995). The germline gene segment usages of the molecules are listed in Table 4.

TABLE 1

Primers (5' to 3') for 5.396.1

| | |
|---|---|
| 4-34 | CCTTTCTCTCCACAGGCGCGCACTCCCAGGTGCAGCTACAGCAGTGG |
| G_3UTR_R | TACGTGCCAAGCATCCTCGC |
| K_O12 | CTTTCTCTCCACAGGCGTGCACTCCGACATCCAGATGACCCAGTCTCC |
| K_3UTR_R | AGGCTGGAACTGAGGAGCAGGTG |

TABLE 2

Primers (5' to 3') for 6.605.1

| | |
|---|---|
| oQVHLVQS_Vh5'-620 | CCTTTCTCTCCACAGGCGCGCACTCCCAGGTTCACCTGGTGCAGTCT |
| G_3UTR_R | TACGTGCCAAGCATCCTCGC |
| o106-2A10-VL5'-384 | CTTTCTCTCCACAGGCGTGCACTCCGACATCCAGATGACCCAGTCT |
| K_3UTR_R | AGGCTGGAACTGAGGAGCAGGTG |

TABLE 3

Primers (5' to 3') for 5.948.1

| | |
|---|---|
| oS255E7a5b1Vh5'-288 | CCTTTCTCTCCACAGGCGCGCACTCCCAGGTGCAGCTGGTGCAGTCT |
| G_3UTR_R | TACGTGCCAAGCATCCTCGC |
| K_A19 | CTTTCTCTCCACAGGCGTGCACTCCGATATTGTGATGACTCAGTCTCCAC |
| K_3UTR_R | AGGCTGGAACTGAGGAGCAGGTG |

Full-length sequences of Anti-IgE antibodies produced by hybridomas are as follows (variable domain in uppercase, CDR regions underlined):

TABLE 4

Sequences of anti-IgE antibodies of the invention produced by hybridomas

| | | | mAbs from hybridomas Sequence identifiers SEQ ID NOs | | |
|---|---|---|---|---|---|
| | | | 5.396.1 | 6.605.1 | 5.948.1 |
| Heavy chain | Full length | DNA | 101 | 105 | 109 |
| | | protein | 102 | 106 | 110 |
| Light chain | Full length | DNA | 103 | 107 | 111 |
| | | protein | 104 | 108 | 112 |

Table 5 below presents the germline gene segment usage and isotypes of anti-IgE antibodies according to the invention isolated from hybridomas:

TABLE 5

Germline gene segment usage and isotypes of anti-IgE antibodies isolated from hybridomas

| | Heavy chain | | | Light chain | | |
|---|---|---|---|---|---|---|
| Clone | $V_H$ | D | $J_H$ | $V_K$ | $J_K$ | Isotype |
| 5.396.1 | 4-34 | 1-1 | JH6b | L1 | JK3 | IgG2 |
| 6.605.1 | 1-18 | 3-22 | JH4b | O12 | JK1 | IgG2 |
| 5.948.1 | 1-08 | 3-22 | JH6b | A3 | JK4 | IgG2 |

The below sequence analysis shows the alignment of germline and expressed sequences (identical residues are shown by dashes, deletions/insertions are shown by hash marks, mutations are listed, and CDRs are underlined).

The antibodies of the invention are advantageously fully human. This should increase safety for use in human, compared to (humanized) murine antibodies.

```
5.396.1
VH
Germline QVQLQQWGAGLLKPSETLSLTCAVYGGSFSGYYWSWIRQPPGKGLEWIGEINHSGSTNYNPSLKS
5.396.1  ------------------------------------------------H-------------

Germline RVTISVDTSKNQFSLKLSSVTAADTAVYYCARDNWMD##YYYYGMDVWGQGTTVTVSS
5.396.1  -------------------------------------SF-------------------

VK
Germline DIQMTQSPSSLSASVGDRVTITCRASQGISNYLAWFQQKPGKAPKSLIYAASSLQS
5.396.1  -----------------------------H-------------------------

Germline GVPSRFSGSGSGTDFTLTISSLQPEDFATYYCQQYNSYPFTFGPGTKVDIK
5.396.1  ----K---------------------------RH----------------

6.605.1
VH
Germline QVQLVQSGAEVKKPGASVKVSCKASGYTFTSYGISWVRQAPGQGLEWMGWISAYNGNTNYAQKLQG
6.605.1  --H---------H----------------------------------------------------

Germline RVTMTTDTSTSTAYMELRSLRSDDTAVYYCARYYYDSSGYYYYFDYWGQGTLVTVSS
6.605.1  -I-------------D----------------####DGD--DP--------------

VK
Germline DIQMTQSPSSLSASVGDRVTITCRASQSISSYLNWYQQKPGKAPKLLIYAASSLQS
6.605.1  -----------------------T-----NW----------------G--T-K-

Germilne GVPSRFSGSGSGTDFTLTISSLQPEDFATYYCQQSYSTPWTFGQGTKVEIK
6.605.1  ---------E-----------------------P----------------

5.948.1
VH
Germline QVQLVQSGAEVKKPGASVKVSCKASGYTFTSYDINWVRQATGQGLEWMGWMNPNSGNTGYAQKFQG
5.948.1  -----------------------------------------------------D-----------

Germline RVTMTRNTSISTAYMELSSLRSEDTAVYYCAR##YDS###YYYYGMDVWGQGTTVTVSS
5.948.1  -------------------------------GH---DGY-SFS---------------

VK
Germline DIVMTQSPLSLPVTPGEPASISCRSSQSLLHSNGYNYLDWYLQKPGQSPQLLIYLGSNRAS
5.948.1  -----------------------------R------------------------------

Germline GVPDRFSGSGSGTDFTLKISRVEAEDVGVYYCMQALQTP##TFGGGTKVEIK
5.948.1  -------------------------------------PA------------
```

Example 4

Cloning of Variable Domains from Anti-IgE Antibodies of the Invention

Anti-IgE antibodies variable domains were cloned into expression vectors as follows:

Poly(A)+ mRNA was isolated using an RNeasy Mini Kit (Qiagen, Cat# 74104) and cDNA synthesized from the mRNA with the SuperScript III First-Strand Synthesis System for RT-PCR (Invitrogen, Cat# 18080051) using oligo (dT) priming. The variable domains were amplified from oligo (dT) primed cDNA using primers listed in Tables 6, 7 and 8. Amplification was achieved using Taq DNA Polymerase (Roche, Cat#1-146-173) and a PTC-200 DNA Engine (MJ Research) with cycling as follows: 2'@94° C.; 5× (30"@94° C., 30"@50° C., 30"@68° C.); 25× (30"@94° C., 30"@68° C., 30"@68° C.); 5'@68° C. The variable domains were then cloned into mammalian expression vectors containing a CMV promoter, constant domains of the appropriate isotype and transcription terminator/polyA signal. These clones were sequence verified using Grills 16th BDTv3.1/dGTP chemistry (Applied Biosystems Inc) and a 3730xl DNA Analyzer (Applied Biosystems Inc).

TABLE 6

| Variable domain primers (5' to 3') for 5.396.1 | |
|---|---|
| 4-34 | CCTTTCTCTCCACAGGCGCGCACTCCCAGGTGCAGCTACAGCAGTGG |
| o009C6Vh3'-298 | ACTCACCTGAGGAGACGGTGACCGTGGTCCC |
| o106-2A10-VL5'-384 | CTTTCTCTCCACAGGCGTGCACTCCGACATCCAGATGACCCAGTCT |
| o1.257.1VL3'-525 | CCTATTCCTTAATTAAGTTATTCTACTCACGTTTGATATCCACTTTGGTCCCAGGGCC |

TABLE 7

Variable domain primers (5' to 3') for 6.605.1

| | |
|---|---|
| oQVHLVQS_Vh5'-620 | CCTTTCTCTCCACAGGCGCGCACTCCCAGGTTCACCTGGTGCAGTCT |
| o106-5A6Vh3'-410 | ACTCACCTGAGGAGACGGTGACCAGGGTTCC |
| o106-2A10-VL5'-384 | CTTTCTCTCCACAGGCGTGCACTCCGACATCCAGATGACCCAGTCT |
| omyo-VL3'-513 | CCTATTCCTTAATTAAGTTATTCTACTCACGTTTGATTTCCACCTTGGTCCCTTGGCC |

TABLE 8

Variable domain primers (5' to 3') for 5.948.1

| | |
|---|---|
| oS255E7Vh5'-288 | CCTTTCTCTCCACAGGCGCGCACTCCCAGGTGCAGCTGGTGCAGTCT |
| GJH6 | ACTCACCTGAGGAGACGGTGACCGTGGT |
| K_A19 | CTTTCTCTCCACAGGCGTGCACTCCGATATTGTGATGACTCAGTCTCCAC |
| JK4_R | TATATTCCTTAATTAAGTTATTCTACTCACGTTTGATCTCCACCTTGGTCCCT |

The resulting clones were again sequence-verified. The full-length sequences for the corresponding recombinant anti-IgE antibodies of the invention (leader sequences omitted) are as presented in Table 9:

TABLE 9

Sequences of recombinant anti-IgE antibodies of the invention

| | | | Recombinant Abs Sequence identifiers SEQ ID NOs | | |
|---|---|---|---|---|---|
| | | | 5.396.1 | 6.605.1 | 5.948.1 |
| Heavy chain | Full length | DNA | 1 | 41 | 81 |
| | | protein | 2 | 42 | 82 |
| | Variable domain | DNA | 3 | 43 | 83 |
| | | protein | 4 | 44 | 84 |
| | CDR1 | DNA | 5 | 45 | 85 |
| | | protein | 6 | 46 | 86 |
| | CDR2 | DNA | 7 | 47 | 87 |
| | | protein | 8 | 48 | 88 |
| | CDR3 | DNA | 9 | 49 | 89 |
| | | protein | 10 | 50 | 90 |
| Light chain | Full length | DNA | 11 | 51 | 91 |
| | | protein | 12 | 52 | 92 |
| | Variable domain | DNA | 13 | 53 | 93 |
| | | protein | 14 | 54 | 94 |
| | CDR1 | DNA | 15 | 55 | 95 |
| | | protein | 16 | 56 | 96 |
| | CDR2 | DNA | 17 | 57 | 97 |
| | | protein | 18 | 58 | 98 |
| | CDR3 | DNA | 19 | 59 | 99 |
| | | protein | 20 | 60 | 100 |

Sequencing revealed differences between the sequences of the hybridoma-derived antibodies and that of the recombinant Abs for 6.605.1. Said differences are however allelic differences in the constant domain and all changes are silent 3rd nucleotide changes.

Example 5

Mutagenesis

Further Anti-IgE Antibodies According to the Invention

Mutagenesis of 5.396.1 and 6.605.1 anti-IgE antibodies was conducted as follows:

Mutagenesis by PCR, in the $V_H$ (S103N) of clone 5.396.1 was conducted with the primers listed in Table 10 and Table 6. Amplification was achieved using Taq DNA Polymerase (Roche, Cat#1-146-173) and a PTC-200 DNA Engine (MJ Research) with cycling as follows: 2'@94° C.; 5× (30"@94° C., 30"@50° C., 30"@68° C.); 25× (30"@94° C., 30"@68° C., 30"@68° C.); 5'@68° C.

Mutagenesis by PCR, in the $V_K$ (K61R) of clone 5.396.1 was conducted using a two step process with the primers listed in Table 10 and Table 6. Step one involved making mutated overlapping variable domain fragments by amplification using the primer set o106-2A10-VL5'-384%5936L (KtoR)3'-647 and an amplification using the primer set o5936L(KtoR)5'-646%1.257.1VL3'-525 and using Taq DNA Polymerase (Roche) and a PTC-200 DNA Engine (MJ Research) with cycling as follows: 2'@94° C.; 5× (30"@94° C., 30"@50° C., 30"@68° C.); 25× (30"@94° C., 30"@68° C., 30"@68° C.); 5'@68° C. Step two involved amplification of the full mutated variable domain by combining the amplified fragments from step one and using the primer set o106-2A10-VL5'-384%1.257.1VL3'-525 and Taq DNA Polymerase (Roche) and a PTC-200 DNA Engine (MJ Research) with cycling as follows: 2'@94° C.; 5× (30"@94° C., 30"@50° C., 30"@68° C.); 25× (30"@94° C., 30"@68° C., 30"@68° C.); 5'@68° C.

Mutagenesis by PCR, in the $V_H$ (H3Q,M13K,D82E) of clone 6.605.1 was conducted using a two step process with the primers listed in Table 10 and Table 7. Step one involved making mutated overlapping variable domain fragments by amplification using the primer set olgE6605Vh_M13K-621/olgE6605H(D82E)3'-625 and an amplification using the primer set olgE6605H(D82E)5'-624%106-5A6Vh3'-410 and using the amplification conditions from above. Step two involved amplification of the full mutated variable domain by combining the amplified fragments from step one and using the primer set oB8-D8-D1hGH-Vh5'-289%106-5A6Vh3'-410 and using the amplification conditions from above.

Mutagenesis by PCR, in the $V_K$ (T25A, T53S) of clone 6.605.1 was conducted using a four step process with the primers listed in Table 10 and Table 7. Step 1 involved making mutated overlapping variable domain fragments by amplification using the primer set o106-2A10-VL5'-384/olgE6605Vk-T25A3'-627 and an amplification using the primer set olgE6605Vk-T25A5'-626/omyo-VL3'-513 and using the amplification conditions from above. Step 2 involved amplification of the full mutated variable domain by combining the amplified fragments from step one and using the primer set o106-2A10-VL5'-384/omyo-VL3'-513 and using the amplification conditions from above. Step 3 involved using the $V_K$ (T25A) variable domain from step 2 and making mutated overlapping variable domain fragments by amplification using the primer set o106-2A10-VL5'-384/olgE6605L(T53K)3'-637 and an amplification using the primer set olgE6605L(T53K)5'-636/omyo-VL3'-513 and using the amplification conditions from above. Step 4 involved amplification of the full mutated variable domain by combining the amplified fragments from step three and using the primer set o106-2A10-VL5'-384/omyo-VL3'-513 and using the amplification conditions from above. All the mutated variants were sequence verified and cloned into mammalian expression vectors explained above.

TABLE 10

Mutagenic primers (5' to 3') for 5.396.1 and 6.605.1

| | |
|---|---|
| o5936HS103N-675 | ACTCACCTGAGGAGACGGTGACCGTGGTCCCTTGGCCCCAGACGTCCATACCGTAGTAGTAGTAGAAGTTGTCGTTCCAGTTGTCTCTCGCACAGTA |
| o5936L(KtoR)5'-646 | TTGCAAAGTGGGGTCCCATCAAGGTTCAGCGGCAGTGGATCTGGG |
| o5936L(KtoR)3'-647 | CCCAGATCCACTGCCGCTGAACCTTGATGGGACCCCACTTTGCAA |
| olgE6605Vh_M13K-621 | CCTTTCTCTCCACAGGCGCGCACTCCCAGGTTCACCTGGTGCAGTCTGGAGCTGAGGTGAAGAAGCCTGGGGCCTCAGTGAAGGTC |
| olgE6605Vh_M13K-621 | CCTTTCTCTCCACAGGCGCGCACTCCCAGGTTCACCTGGTGCAGTCTGGAGCTGAGGTGAAGAAGCCTGGGGCCTCAGTGAAGGTC |
| olgE6605H(D82E)5'-624 | GACACATCCACGAGCACAGCCTACATGGAACTGAGGAGCCTGAGATCTGACGAC |
| olgE6605H(D82E)3'-625 | GTCGTCAGATCTCAGGCTCCTCAGTTCCATGTAGGCTGTGCTCGTGGATGTGTC |
| oB8-D8-D1hGH-Vh5'-289 | CCTTTCTCTCCACAGGCGCGCACTCCCAGGTCCAGCTGGTGCAGTCT |
| olgE6605Vk-T25A5'-626 | GGAGACAGAGTCACCATCACTTGCCGGGCAAGTCAGAGTATTAGCAACTGGTTA |
| olgE6605Vk-T25A3'-627 | TAACCAGTTGCTAATACTCTGACTTGCCCGGCAAGTGATGGTGACTCTGTCTCC |
| olgE6605L(T53K)5'-636 | AAACTCCTGATCTATGGTGCCTCCAGTTTGAAAAGTGGGGTCCCATCAAGG |
| olgE6605L(T53K)3'-637 | CCTTGATGGGACCCCACTTTTCAAACTGGAGGCACCATAGATCAGGAGTTT |

Mutagenesis of 5.948.1 anti-IgE antibody may be conducted by any well-known techniques in site-directed mutagenesis.

Sequences of the resulting anti-IgE antibodies of the invention (leader sequences omitted) are as outlined below in Table 11:

TABLE 11

Sequence of anti-IgE antibodies of the invention

Recombinant Abs Sequence identifiers SEQ ID NOs

| | | | 5.396.1 (Hc-S103N; Lc-K61R) | 6.605.1 (Hc-H3Q, M13K, D82E; Lc-T25A, T53S) | 5.948.1 (H100Y) |
|---|---|---|---|---|---|
| Heavy chain | Full length | DNA | 21 | 61 | 121 |
| | | protein | 22 | 62 | 122 |
| | Variable domain | DNA | 23 | 63 | 123 |
| | | protein | 24 | 64 | 124 |
| | CDR1 | DNA | 25 | 65 | 125 |
| | | protein | 26 | 66 | 126 |
| | CDR2 | DNA | 27 | 67 | 127 |
| | | protein | 28 | 68 | 128 |
| | CDR3 | DNA | 29 | 69 | 129 |
| | | protein | 30 | 70 | 130 |
| Light chain | Full length | DNA | 31 | 71 | 131 |
| | | protein | 32 | 72 | 132 |
| | Variable domain | DNA | 33 | 73 | 133 |
| | | protein | 34 | 74 | 134 |
| | CDR1 | DNA | 35 | 75 | 135 |
| | | protein | 36 | 76 | 136 |
| | CDR2 | DNA | 37 | 77 | 137 |
| | | protein | 38 | 78 | 138 |
| | CDR3 | DNA | 39 | 79 | 139 |
| | | protein | 40 | 80 | 140 |

Example 6

Nucleic Acid Deposits with the ATCC

The following deposits were made with the American Type Culture Collection (ATCC), P.O. Box 1549, Manassas, Va. 20108, USA (samples received on Nov. 7, 2006), in accordance with the Budapest Treaty, as presented in Table 12.

TABLE 12

Biological deposits for anti-IgE antibodies of the invention

| Vial number | Insert in vector pCR2.1 TOPO | ATCC Patent Deposit Designation | SEQ ID NO: |
|---|---|---|---|
| UC25516 | 5.396.1 Heavy chain full-length cDNA from Hybridoma | PTA-7977 | 101 |
| UC25517 | 5.396.1 Light chain full-length cDNA from Hybridoma | PTA-7982 | 103 |
| UC25518 | 5.396.1 H(S103N)-hG2 Heavy chain full-length cDNA | PTA-7981 | 21 |
| UC25519 | 5.396.1 L(K61R)-hKappa Light chain full-length cDNA | PTA-7980 | 31 |
| UC25520 | 5.948.1 Heavy chain full-length cDNA from Hybridoma | PTA-7979 | 109 |
| UC25521 | 5.948.1 Light chain full-length cDNA from Hybridoma | PTA-7986 | 111 |
| UC25522 | 6.605.1 Heavy chain full-length cDNA from Hybridoma | PTA-7985 | 105 |
| UC25523 | 6.605.1 Light chain full-length cDNA from Hybridoma | PTA-7984 | 107 |
| UC25524 | 6.605.1 H(H3Q, M13K, D82E)-hG2 Heavy chain full-length cDNA | PTA-7983 | 61 |
| UC25525 | 6.605.1 L(T25A, T53S)-hKappa Light chain full-length cDNA | PTA-7978 | 71 |

Example 7

Recombinant Expression and Purification of Anti-IgE Antibodies of the Invention The CMV promoter containing expression vectors were transfected in 293 Freestyle (Invitrogen) cells according to the vendor's protocol. Supernatants from these cells were collected by centrifugation and purified by standard Protein-A affinity chromatography to isolate recombinant immunoglobulins. These proteins were then characterized by SDS-PAGE, SEC (size exclusion chromatography), Mass spectrometer, and spectrophotometrically.

Example 8

IgE Binding Assay

Assay Principle

Binding of test anti-IgE antibodies to IgE was tested in an IgE cell binding assay using an RBL-2H3 cell line transfected with the human FcεR1. This rat basophilic cell line is a stable clone which has been transfected with the human FcεR1 α, β and γ receptor sub-units cDNAs (licensed from Drs Kinet and Jouvin, Beth Israel Deaconess Medical Center (Wiegand T W, et al., *J Immunol.* 1996 Jul. 1; 157(1):221-30; Dibbern D A Jr, et al., *J Immunol Methods.* 2003 Mar. 1; 274(1-2):37-45)). Cells were cultured for 24 hours then incubated with test anti-IgE antibodies and human IgE for a further 24 hours. Following washing to remove anti-IgE:IgE complexes, remaining IgE bound to FcεR1 was detected with a biotinylated polyclonal anti-IgE antibody with streptavidin-HRP and OPD. A reduction in IgE binding was observed with anti-IgE antibodies in a concentration-related manner.

Protocol

RBL-2H3 (FcεR1) cells were cultured in MEM-Earles (Invitrogen Cat. No. 2109002) supplemented with 2 mM L-Glutamine (Sigma, Cat. No. G7513), 1 mg/mL Geneticin Liquid (Invitrogen Cat. No. 10131027) and 15% FBS (PAA Laboratories GmbH, Cat. No. A15-043). RBL-2H3 (FcεR1) cells were seeded into sterile 96-well plates (Costar, Fisher Scientific, Cat. No. TKY-521-0905) at $1\times10^5$ cells/well and cultured overnight at 37° C., 5% $CO_2$ in a humidified atmosphere. The next day cells were washed 3× with 150 µL/well wash buffer (10% BSA, Sigma Cat. No A7030, in PBS, Sigma, Cat. No D8537). IgE and all antibodies for the following steps were made up in culture media with the omission of Geneticin. 25 µL 1 µg/mL IgE (Human myeloma, azide free, Serotec, Cat. No. PHP008x2) was added to all wells (except background control where 25 µl media was added). Antibodies were diluted as required (0.008-3 µg/mL concentration range depending on potency of antibody) and 25 µL added to appropriate wells (except background control and positive control wells where 25 µl media was added). Cells were incubated with IgE and anti-IgE antibodies overnight at 37° C., 5% $CO_2$ in a humidified atmosphere. Plates were then washed 3× with 150 μL/well wash buffer to remove unbound IgE and IgE-anti-IgE complexes. Bound IgE was detected using a polyclonal biotinylated anti-IgE antibody (Vector Laboratories, Cat. No. BA3040) diluted to 10 μg/mL, 50 μL was added to all wells and incubated for 2 hours at 37° C., 5% $CO_2$ in a humidified atmosphere. Cells were washed 3× with 150 μL/well wash buffer and then incubated with 50 μL/well streptavidin-HRP (Amersham Bioscience, Cat. No. RPN 1231) diluted 1:250, for 45 minutes. Cells were washed 3× with 150 μl/well wash buffer. 50 μL OPD (Dako, Cat. No. S2045) was added to all wells and the colour allowed to develop for 10 minutes before stopping the reaction with 50 μL 0.6M $H_2SO_4$ and the absorbance measured at 490 nm.

Results

To determine the potency of antibodies, background absorbance was subtracted from all values and then a mean value for the positive control (IgE only) calculated and antibody data expressed as a percent inhibition of IgE binding from positive control value. Incubation of anti-IgE antibodies resulted in a concentration-related reduction in IgE binding. The antibodies of the invention all showed a concentration-related reduction in IgE binding to the RBL-2H3 (FcεR1) cells and $IC_{50}$ values less than 0.5 μg/mL, and were assessed further in functional assays.

In this assay $IC_{50}$ was defined as the concentration of antibody required to reduce IgE binding by 50%, using value for positive control wells as 100%.

Example 9

Inhibition of Degranulation Assay

Assay Principle

The potential of test anti-IgE antibodies to inhibit IgE-mediated degranulation was determined using RBL-2H3 (FcεR1) cells. Cells were cultured with test anti-IgE antibodies and human IgE for 48 hours. Cells were washed to remove anti-IgE:IgE complexes, leaving IgE bound to FcεR1, then stimulated with a polyclonal anti-IgE antibody which crosslinks bound IgE, resulting in IgE-mediated degranulation. Histamine release was used as the endpoint in this assay as a marker of degranulation and a concentration related reduction in histamine release was observed with increasing concentration of test anti-IgE antibody.

Protocol

RBL-2H3 (FcεR1) cells were cultured in MEM-Earles (Invitrogen Cat. No. 2109002) supplemented with 2 mM L-Glutamine (Sigma, Cat. No. G7513), 1 mg/mL Geneticin Liquid (Invitrogen Cat. No. 10131027) and 15% FBS (PAA Laboratories GmbH, Cat. No. A15-043). RBL-2H3 (FcεR1) cells were seeded into sterile 96-well plates (Costar, Fisher Scientific, Cat. No. TKY-521-090S) at $1 \times 10^5$ cells/well and incubated with 0.0625 μg/mL IgE (Human myeloma, azide free, Serotec, Cat. No. PHP008×2) and test anti-IgE antibodies (0.0001-30 μg/mL concentration range depending on potency of antibody) for 48 hours at 37° C., 5% $CO_2$ in a humidified atmosphere. Cells, antibodies and IgE were all prepared in MEM-Earles (Invitrogen Cat. No. 2109002), 2 mM L-Glutamine (Sigma, Cat. No. G7513) and 15% FBS (PAA Laboratories GmbH, Cat. No. A15-043). After 48 hours cells were washed with 1×RPMI (Sigma, Cat. No. R1145) supplemented with 10% heat inactivated (56° C. water batch for 30 minutes) FBS (PAA Laboratories GmbH, Cat. No. A15-043), 0.2% sodium bicarbonate (Sigma, Cat. No. S8761) to remove unbound anti-IgE and IgE:anti-IgE complexes prior to stimulation. Cells were stimulated with 5 μg/mL polyclonal anti-IgE antibody (Sigma, Cat. No. 10632) which crosslinks receptor bound IgE for 1 hour. Total histamine was determined from 2% Triton-X100 (Sigma, Cat. No. T9284) lysed wells and spontaneous release from cells stimulated with stimulation media alone. Anti-IgE and Triton-X-100 were diluted in stimulation media. Stimulation media comprised 1×RPMI (Sigma, Cat. No. R1145) supplemented with 10% heat inactivated (56° C. water batch for 30 minutes) FBS (PAA Laboratories GmbH, Cat. No. A15-043), 2% sodium bicarbonate (Sigma, Cat. No. S8761) and 45% Deuterium oxide (Fisher Scientific, Cat. No. 16631-1000). Cells were stimulated for 1 hour at 37° C., 5% $CO_2$ in a humidified atmosphere. Plates were then centrifuged (200×g, 5 minutes) and the supernatant collected for measurement of histamine release. Histamine release was measured by ELISA (IBL, Cat. No. CVRE59221), according to the manufacturers instructions, as a marker of degranulation.

Results

Histamine release was expressed as a percentage of the total release and then to calculate specific release, spontaneous release was subtracted from % values as follows:

% total histamine release=(Histamine ng/mL in test or spontaneous control wells/mean Histamine ng/mL in total wells)×100

Specific release=(% of total histamine release in test well)−(Mean % of total histamine release from spontaneous wells).

The effect of antibody was expressed as percent inhibition of histamine released from control wells incubated in the absence of anti-IgE antibody (IgE and cells only)

% inhibition=((mean control wells stimulated with polyclonal anti-IgE−test-antibody wells stimulated with polyclonal anti-IgE)/mean control wells stimulated with polyclonal anti-IgE)×100.

$IC_{50}$ values are the concentration of antibody required to inhibit control histamine release by 50% and are detailed in Table 13. The anti-IgE antibodies of the invention are advantageous, in that they are significantly more potent than E25 at inhibiting IgE-mediated histamine release as a marker of degranulation.

TABLE 13

$IC_{50}$ values of anti-IgE antibodies of the invention, in inhibition of IgE-mediated degranulation Data are geometric mean $IC_{50}$ with 95% confidence intervals.

| Anti-IgE antibody | $IC_{50}$ - μg/mL (95% confidence intervals) | 'n' |
|---|---|---|
| E25 | 1.47 (1.24-1.74) | 83 |
| 5.396.1 (recombinant) | 0.0709 (0.0572-0.0879) | 43 |
| 5.396.1 (Hc-S103N Lc-K61R) | 0.0262 (0.0201-0.0341) | 24 |
| 6.605.1 (recombinant) | 0.124 (0.0980-0.157) | 52 |
| 6.605.1 (Hc-H3Q, M13K, D82E Lc-T25A, T53S) | 0.0736 (0.0491-0.110) | 4 |
| 5.948.1 - Batch 1 (762.8 μg/mL) (recombinant) | 0.360 (0.339-0.382) | 3 |
| 5.948.1 - Batch 2 (5.2 mg/mL) (recombinant) | 0.123 (0.077-0.195) | 24 |
| 5.948.1 (Hc-H100Y) | 0.0121 (0.00878-0.0167) | 24 |

Example 10

RBL-2H3 (FcεR1) Agonist Assay

Assay Principle

The potential for test anti-IgE antibodies to crosslink receptor-bound IgE and stimulate IgE-dependent degranulation was determined using RBL-2H3 (FcεR1) cells. Cells were cultured with human IgE for 48 hours then washed to remove unbound IgE. Test anti-IgE antibodies were then added to cells to determine whether they are able to bind and cross-link receptor bound IgE to cause degranulation. Histamine release was measured as a marker of degranulation. Positive and negative control anti-IgE antibodies were used in all assays to enable comparison with test anti-IgE antibodies.

Protocol

Cells were cultured as described for the inhibition of degranulation assay. For the agonist assay cells were seeded into sterile 96-well plates (Costar, Fisher Scientific, Cat. No. TKY-521-0905) at $1 \times 10^5$ cells/well with 0.25 µg/mL IgE (Human myeloma, azide free, Serotec, Cat. No. PHP008X2 and incubated for 48 hours at 37° C., 5% $CO_2$ in a humidified atmosphere. Cells and IgE were prepared in MEM-Earles (Invitrogen Cat. No. 2109002), 2 mM L-Glutamine (Sigma, Cat. No. G7513) and 15% FBS (PAA Laboratories GmbH, Cat. No. A15-043).

After 48 hours cells were washed with 1×RPMI (Sigma, Cat. No. R1145) supplemented with 10% heat inactivated (56° C. water bath for 30 minutes) FBS (PAA Laboratories GmbH, Cat. No. A15-043) and 0.2% sodium bicarbonate (Sigma, Cat. No. S8761) to remove unbound IgE prior to stimulation with anti-IgE antibodies. A polyclonal anti-IgE antibody (Sigma, Cat. No. 10632) known to crosslink receptor bound IgE, was used as a positive control. Test and control antibodies were tested at 0.04-10 µg/mL. Total histamine was determined from 2% Triton-X100 (Sigma, Cat. No. T9284) lysed wells and spontaneous release from cells stimulated with media alone. Antibodies and Triton-X-100 were diluted in stimulation media. Stimulation media comprised 1×RPMI (Sigma, Cat. No. R1145) supplemented with 10% heat inactivated (56° C. water bath for 30 minutes) FBS (PAA Laboratories GmbH, Cat. No. A15-043), 2% sodium bicarbonate (Sigma, Cat. No. S8761) and 45% Deuterium oxide (Fisher Scientific, Cat. No. 16631-1000). Cells were stimulated for 1 hour at 37° C., 5% $CO_2$ in a humidified atmosphere. Plates were then centrifuged (200×g, 5 minutes) and the supernatant collected for measurement of histamine release. Histamine release was measured by ELISA (IBL, Cat. No. CVRE59221), according to the manufacturer's instructions, as a marker of degranulation. Histamine release was calculated as a percentage of the total release and effect of antibodies expressed as percentage of total release.

Results

A polyclonal anti-IgE was used as a positive control in all experiments and this stimulated histamine release (~30% of total histamine). Advantageously, none of the anti-IgE monoclonal antibodies of the invention stimulated IgE-mediated histamine release above spontaneous release when tested at concentrations of 0.04-10 µg/mL (see FIGS. 1 and 2). This observation suggests that in vivo the anti-IgE antibodies of the invention will not crosslink FcεR1-receptor bound IgE and thus will not stimulate degranulation.

Example 11

Human Blood Basophil Agonist Assay

Assay Principle

Lack of agonist activity was confirmed in human blood basophils isolated from fresh whole blood using the same principles as for the RBL-2H3 (FcεR1) agonist assay.

Protocol

Human mononuclear cells were isolated from whole blood using Histopaque tubes (Sigma, Cat. No. A0561). Fresh human venous blood from healthy volunteers was collected into 50 mL tubes containing 1 mL 10 mg/mL heparin (Sigma, Cat. No. H3393). Blood was then diluted 1:1 in 5% FCS/PBS (FCS from PAA Laboratories GmbH, Cat. No. A15-043 and PBS from Sigma, Cat. No. D8537) and poured into Histopaque tubes (Sigma, Cat. No. A0561) which were centrifuged at 500×g for 35 minutes. Buffy coats were collected, washed and resuspended in RPMI media (Invitrogen, Cat. No. 32404-014) containing 10% FBS (PAA Laboratories GmbH, Cat. No. A15-043). Cells were diluted to $1.2 \times 10^7$ white blood cells/mL before adding to 96-well sterile cell culture plates (Costar, Fisher Scientific, Cat. No. TKY-521-090S) at $6 \times 10^5$ cells/well with the addition of human IgE (Human myeloma, azide free, Serotec, Cat. No. PHP008×2) at 0.5 µg/mL final concentration in RPMI media with 10% FBS, as previously described. Cells were incubated overnight at 37° C., 5% $CO_2$ in a humidified atmosphere. Media was removed prior to stimulation with anti-IgE antibodies (0.15-20 µg/mL). A polyclonal anti-IgE antibody (Sigma, Cat. No. 10632) known to crosslink receptor bound IgE was used as a positive control. Total histamine was determined from 0.3% Triton-X100 (Sigma, Cat. No. T9284) lysed wells and spontaneous release determined from cells stimulated with media alone. Antibodies and Triton-X-100 were diluted in cell media and spontaneous wells were incubated with cell media alone. Cell media comprised RPMI media (Invitrogen, Cat. No. 32404-014) with 10% FBS (PAA Laboratories GmbH, Cat. No. A15-043). Cells were stimulated for 30 minutes at 37° C., 5% $CO_2$ in a humidified atmosphere. Plates were then centrifuged (200×g, 5 minutes) and the supernatant collected for measurement of histamine release. Histamine release was measured by ELISA as a marker of degranulation (IBL, Cat. No. CVRE59221, according to the manufacturer's instructions). Histamine release was calculated as a percentage of the total release and effect of antibodies expressed as percentage of total release.

Results

A polyclonal anti-IgE was used as a positive control in all experiments and this caused a large release of histamine (~50% of the total histamine). Advantageously, none of the anti-IgE monoclonal antibodies of the invention stimulated IgE-mediated histamine release above spontaneous release from these cells when tested at concentrations of 0.15-20 µg/mL (see FIGS. 3 and 4). The observation that the anti-IgE antibodies of the invention do not have agonist activity with isolated human blood basophils confirms that seen in the RBL-2H3 (FcεR1) cell agonist assay (see above).

Example 12

Free IgE Depletion from Human Serum In Vitro

Assay Principle

The ability of test anti-IgE antibodies to bind IgE in serum and reduce the level of free IgE was measured in vitro. Test anti-IgE antibodies (herein after, test-antibodies) were individually incubated in serum overnight to enable binding of test-antibody to IgE in serum. Remaining free IgE (i.e. not bound to the test-antibody) was measured by ELISA, wherein the same test-antibody itself was used as the capture reagent on the plate. Control assays have shown that free IgE binds to the capture reagent, whereas (test-antibody)-IgE complexes do not. Serum-(test-antibody) incubates were then incubated with the capture reagent for 2 hours to enable binding of 'remaining' free IgE to the capture reagent. Plates were washed to remove (test-antibody)-IgE complexes, leaving 'remaining' free IgE bound to the capture reagent. This 'remaining' free IgE (bound on to ELISA plate) was subsequently detected with a biotinylated polyclonal anti-IgE antibody. A concentration-related reduction in free IgE measurement was observed with increasing concentrations of test-antibody.

The assay may thus be outlined as follows:
Incubate test-antibody with serum ~16 h;
To detect free IgE, add (test-antibody)/serum to a capture ELISA plate and incubate for 2 h (Capture ELISA plate is coated with same test-antibody);
Wash to remove (test-antibody)-IgE complexes, leaving 'remaining' free IgE bound to capture reagent on plate;
Measure bound 'remaining' free IgE' captured on to the plate using biotinylated polyclonal anti-IgE, streptavidin-HRP and OPD detection system.

Protocol

5 µL test anti-IgE antibodies diluted in 50 mM TBS pH 8.0 (Sigma, Cat. No. T6664) or TBS control without antibody were spiked into 45 µl neat serum collected from healthy volunteers and incubated in sterile 96-well plates (Costar, Fisher Scientific, Cat. No. TKY-521-0905) overnight at 37° C. 5% $CO_2$ in a humidified atmosphere to allow binding of the test-antibody to IgE in serum. ELISA plates were prepared by coating Nunc Maxisorp 96-well plates (Fisher Scientific, Cat. No. DIS-971-010P) overnight at 4° C. with 50 µl 2.5 µg/mL capture anti-IgE antibody (diluted in TBS, Sigma, Cat. No. T6664). The next day ELISA plates were washed 1× with 300 µL/well wash buffer (0.05% Tween-20, Sigma, Cat. No. P7949/TBS) then blocked with 150 µL/well 1% BSA (Sigma, Cat. No. A7030) in TBS for 1 hour at room temperature. Plates were then washed 1× with 300 µL/well wash buffer before adding 50 µl of IgE standard, anti-IgE/serum samples or diluent blank all diluted in 1% BSA/0.05% Tween-20/TBS diluent buffer. Human serum IgE standard from NIBSC (National Institute for Biological Standards and Control, Cat. No. 75/502) was used as the standard in this assay and a standard curve of 3-200 ng/mL was used on each plate. Serum was required to be diluted at least 1 in 10 to eliminate serum interference. For new donors serum was diluted 1:10, 1:50 and 1:200 to determine the most suitable dilution to eliminate serum interference whilst predicting the value in the linear part of the standard curve. As a general rule serum with <200 ng/mL IgE was diluted 1:10, serum with >200 ng/mL IgE was diluted 1:50 or 1:200. Standards and samples were incubated for 2 hours at room temperature, then washed 4× with 300 µL wash buffer. Captured free IgE was detected with 50 µL/well biotinylated polyclonal anti-IgE (Vector Laboratories, Cat. No. BA3040) diluted to 0.5 µg/mL in 1% BSA/0.05% Tween-20/TBS diluent buffer. Wells were incubated for 1 hour at room temperature then washed (4×300 µL wash buffer). 50 µL Streptavidin-HRP (Amersham Bioscience, Cat. No. RPN 1231) diluted 1:1000 in diluent buffer was added to all wells and incubated for 45 minutes at room temperature. Wells were washed (4×300 µL wash buffer). 50 µL OPD (Dako, Cat. No. S2045) was added to all wells and the colour allowed to develop for 10 minutes before stopping the reaction with 50 µl 0.6M $H_2SO_4$ and the absorbance measured at 490 nm. The concentration of IgE detected was calculated by plotting the NIBSC standard curve and extrapolating IgE concentrations from the standard curve. These values were then multiplied by the dilution factor to give the IgE concentration in ng/mL. Free IgE (ng/mL) was plotted against antibody concentration.

Results

The potencies of antibodies were expressed as the concentration required to reduce the free IgE concentration in serum to about 25 ng/mL ($IC_{25\ ng/mL}$). Advantageously, anti-IgE antibodies of the invention were able to reduce the free IgE to less than 25 ng/mL (see Tables 14-15).

TABLE 14

Concentration of test-anti-IgE antibodies (µg/mL) required to reduce the free IgE levels in a human serum sample to a value of about 25 ng/mL
DIN: Donor Identification Number

| Serum sample | Capture/Test-antibody | | | | | | | Mean initial free IgE levels (ng/mL) |
|---|---|---|---|---|---|---|---|---|
| | E25 | 5.396.1 (recombinant) | 5.396.1 S103N K61R | 6.605.1 (recombinant) | 6.605.1 H3Q M13K D82E T25A T53S | 5.948.1 (recombinant) | 5.948.1 H100Y | |
| | Concentration of test-antibody required to reduce the free IgE concentration to a value of about 25 ng/mL (µg/mL) | | | | | | | |
| DIN 0461 | 65 | nd | 0.15 | nd | nd | 1.47 | 0.34 | 80 |
| DIN 0155 | 103 | nd | 0.14 | nd | nd | 1.81 | 0.34 | 93 |
| DIN 0649 | 139 | nd | 0.46 | nd | nd | 1.95 | 0.39 | 93 |
| DIN 0623 experiment 2 | 90 | nd | 0.20 | nd | nd | 4.13 | 0.76 | 133 |
| DIN 0623 experiment 1 | 39 | 0.27 | 0.37 | 0.38 | 0.19 | 0.50 | nd | 145 |

TABLE 14-continued

Concentration of test-anti-IgE antibodies (μg/mL) required to
reduce the free IgE levels in a human serum sample to a value of about 25 ng/mL
DIN: Donor Identification Number

| | Capture/Test-antibody | | | | | | |
|---|---|---|---|---|---|---|---|
| Serum sample | E25 | 5.396.1 (recombinant) | 5.396.1 S103N K61R | 6.605.1 (recombinant) | 6.605.1 H3Q M13K D82E T25A T53S | 5.948.1 (recombinant) | 5.948.1 H100Y | Mean initial free IgE levels (ng/mL) |
| | Concentration of test-antibody required to reduce the free IgE concentration to a value of about 25 ng/mL (μg/mL) | | | | | | | |
| DIN 0591 | 139 | nd | 0.24 | nd | nd | 2.35 | 0.55 | 152 |
| DIN 0347 | 211 | nd | 0.48 | nd | nd | 4.92 | 1.33 | 221 |
| DIN 0321 experiment 1 | 105 | 0.67 | 0.85 | 1.99 | 0.51 | 1.34 | nd | 262 |
| DIN 0321 experiment 2 | 202 | nd | 0.45 | nd | nd | 7.90 | 2.55 | 265 |
| DIN 0632 experiment 2 | 275 | nd | nd | nd | nd | 6.31 | 2.29 | 289 |
| DIN 0011 experiment 2 | 325 | nd | 0.77 | nd | nd | 6.34 | 2.96 | 326 |
| DIN 0284 | 145 | 0.87 | 0.98 | 2.40 | 0.99 | 2.45 | nd | 339 |
| DIN 0632 experiment 1 | 385 | 1.43 | 1.11 | nd | 2.80 | 8.91 | nd | 532 |
| DIN 0451 experiment 2 | 587 | nd | 2.21 | nd | nd | 39.67 | 10.46 | 534 |
| DIN 0011 experiment 1 | 202 | 0.98 | 1.12 | 5.00 | 2.29 | 3.30 | nd | 555 |
| DIN 0451 experiment 1 | 410 | 1.81 | 1.59 | 10.84 | 3.71 | 11.61 | nd | 557 |
| DIN 0707 | 653 | 2.87 | 2.75 | nd | nd | nd | nd | 1051 |
| DIN 0749 | 843 | 3.12 | 2.83 | nd | nd | nd | nd | 1140 |
| DIN 0356 | 2334 | 3.60 | 4.31 | 11.63 | nd | nd | nd | 1350 |
| DIN 0251 | 2914 | 3.87 | 4.68 | 27.94 | nd | nd | nd | 1632 |
| DIN 0382 | 10629 | 5.74 | 7.09 | nd | nd | 25.00 | nd | 2827 |
| DIN 0748 | 30737 | 10.92 | 10.69 | nd | nd | 25.13 | nd | 4609 |
| Geometric mean with 95% confidence interval | 381 (184-791) | 2.0 (1.0-3.8) | 1.0 (0.6-1.8) | 4.4 (1.2-16.4) | 1.1 (0.3-3.8) | 4.7 (2.6-8.3) | 1.2 (0.5-2.6) | | nd: not determined

TABLE 15

Reduction in free IgE by test anti-IgE antibodies in human serum samples.
Data are geometric mean $IC_{25\ ng/ml}$ confidence intervals from 6-22 dondors.

| Antibody | $IC_{25\ ng/mL}$ (μg/mL) | Initial IgE concentration (ng/mL) | 'n' |
|---|---|---|---|
| E25 | 381 (184-791) | 639 (278-1001) | 22 |
| 5.396.1 (recombinant) | 2.0 (1.0-3.8) | 1207 (335-2079) | 12 |
| 5.396.1 (Hc-S103N Lc-K61R) | 1.0 (0.6-1.8) | 791 (296-1287) | 21 |
| 6.605.1 (recombinant) | 4.4 (1.2-16.4) | 757 (206-1308) | 7 |
| 6.605.1 (Hc-H3Q, M13K, D82E Lc-T25A, T53S) | 1.1 (0.3-3.8) | 464 (255-673) | 6 |
| 5.948.1 - Batch 1 (762.8 μg/mL) (recombinant) | 4.7 (2.6-8.3) | 713 (60-1365) | 18 |
| 5.948.1 (Hc-H100Y) | 1.2 (0.5-2.6) | 223 (130-316) | 10 |

Anti-IgE antibodies of the invention (5.396.1, 5.396.1 Hc-S103N Lc-K61R, 6.605.1, 6.605.1 Hc-H3Q,M13K, D82E Lc-T25A, T53S and 5.948.1) have been shown to reduce the free IgE levels to below 25 ng/mL. E25 is also able to reduce free IgE to below 25 ng/mL; however significantly more antibody is required (i.e. a higher Clinically, this could be advantageous with being able to lower the dose of monoclonal antibody to generate the same effect on lowering free IgE levels in the circulation. Additionally an increased patient population could be treated i.e. those with higher initial free IgE concentration and/or higher body weight.

Example 13

Selectivity Over Other Immunoglobulins

Assay Principle

The cross reactivity of the anti-IgE antibodies of the invention with other human immunoglobulins (IgA, IgE, IgG1 and IgG3) was determined in an ELISA assay. Immunoglobulins were coated onto plates and test-anti-IgE antibody incubated before detection of binding with a biotinylated anti-IgG2 antibody.

Protocol

IgA (Sigma, Cat. No. 12636), IgE (Serotec, Cat. No. PHP008×2), IgG1 (Biodesign, Cat. No. A50183H), and IgG3 (Biodesign, Cat. No. A50186H) were coated directly onto a Nunc Maxisorp™ 96-well plates (Fisher Scientific, Cat. No.

DIS-971-010P) at 4 µg/mL in PBS (0.01M phosphate buffer, 0.0027M potassium chloride, 0.137M sodium chloride, pH 7.4, Sigma, Cat. No. P4417) overnight at 4° C. Wells were washed 3× with 150 µL wash buffer (0.05% Tween-20 (Sigma, Cat. No. P7949)/PBS) then blocked with 150 µL/well blocking buffer (2.5% BSA (Sigma, Cat. No. A7030)/PBS) for 2 hours at room temperature. Wells were washed 3× with 150 µL wash buffer/well. Control mouse anti-IgA (Serotec, Cat. No. MCA476G), mouse anti-IgE (Biodesign, Cat. No. Z86410M), mouse anti-IgG1 (Serotec, Cat. No. MCA514G) and mouse anti-IgG3 (Biodesign, Cat. No. Z20152M) were added to control wells at 250 ng/mL, 800 ng/mL or 50 µL/well. All test antibodies were human IgG2 isotype and were added to wells at 250 ng/mL, 50 µL/well. Antibodies were diluted in diluent buffer (PBS/1% BSA/0.05% Tween-20) and this was added to blank control wells (duplicate wells for each secondary antibody used). Antibodies were incubated for 2 hours at room temperature. Wells were washed 3× with 150 µL wash buffer/well. Binding of control antibodies to immunoglobulin was detected with anti-mouse IgG-HRP conjugate (Sigma, Cat. No. A4416) diluted 1:8000 in diluent buffer. 50 µL/well was added to control antibody and blank wells. Wells were incubated for 1 hour at room temperature, then washed 3× with 150 µL wash buffer/well. 50 µl OPD (Dako, Cat. No. S2045) was added to all wells and the colour allowed to develop for 10 minutes before stopping the reaction with 0.6M $H_2SO_4$ and the absorbance measured at 490 nm. Binding of test IgG2 anti-IgE antibodies was detected using a biotinylated anti-human IgG2 (Zymed, Cat. No. 05-3540). This antibody was diluted 1:500 in diluent buffer before adding 50 µL/well to test antibody and blank wells. Wells were incubated for 1 hour at room temperature then washed 3× with 150 µL wash buffer/well. Streptavidin-HRP (Amersham Bioscience, Cat. No. RPN 1231) diluted 1:2000 in diluent buffer was added to all wells and incubated for 45 minutes at room temperature. Wells were washed (3×150 µL wash buffer). 50 µL OPD (Dako, Cat. No. S2045) was added to all wells and the colour allowed to develop for 10 minutes before stopping the reaction with 50 µL 0.6M $H_2SO_4$ and the absorbance measured at 490 nm.

Results

No binding to IgA, IgG1 or IgG3 was detected for any of the anti-IgE antibodies of the invention when tested at 250 ng/mL or 800 ng/mL whereas a large signal was seen for binding to IgE (Table 16). These observations show that the anti-IgE antibodies of the invention are highly selective for IgE over IgA, IgG1 and IgG3.

TABLE 16

Binding of anti-IgE antibodies to IgA, IgG1, IgG3 and IgE. Values are $A_{290\,nm}$.

| Antibody | Immunoglobulin | | | |
|---|---|---|---|---|
| | IgA | IgG1 | IgG3 | IgE |
| 5.396.1 (recombinant) | 0.04 | 0.07 | 0.05 | 2.83 |
| 5.396.1 S103N/K61R | 0.04 | 0.08 | 0.05 | 2.80 |
| 6.605.1 (recombinant) | 0.04 | 0.07 | 0.05 | 3.01 |
| 6.605.1 H3Q M13K D82E/T25A T53S | 0.04 | 0.07 | 0.04 | 2.92 |
| 5.948.1 (recombinant) | 0.04 | 0.07 | 0.04 | 2.57 |
| 5.948.1 (Hc-H100Y) | 0.05 | 0.06 | 0.06 | 1.05 |

Example 14

Determination of Affinity Constants ($K_D$) by BIAcore™

Assay Principle

The kinetic constants $k_{on}$ and $k_{off}$ were determined with serial dilutions of full length human IgE (Serotec, Cat. No. PHP008X2 or Europa Bioproducts, Cat. No CP1035K) binding to the covalently immobilized anti-IgE antibody using the BIAcore™ 3000 instrument (BIAcore™, Uppsala, Sweden).

Protocol

For covalent anti-IgE antibody immobilization standard EDC-NHS amine coupling chemistry was used. An immobilization binding response of 50-600 RU was obtained using CM5 sensor chips (BIAcore™) and 10 mM sodium acetate, pH 5.0 as immobilization buffer. The reference flow cell was activated (with EDC-NHS) and blocked (with ethanolamine) but no protein was immobilized. Kinetic measurements were carried out in HBS-EP buffer (10 mM HEPES, 150 mM NaCl, 3 mM EDTA, 0.005% v/v Surfactant P20 pH 7.4, supplied by BIAcore™) at a flow rate of 50 or 100 µL/min using an IgE concentration range from 0.09-600 nM. Injection time for each concentration was 3.25 minutes, followed by 20 minutes dissociation phase. A regeneration step was included after the dissociation phase; the conditions used for the various antibodies are given in Table 17 below.

TABLE 17

Regeneration conditions used for each anti-IgE antibody

| Anti-IgE Antibody | Regeneration solution | Injection time (s) | Flow rate (µL/min) |
|---|---|---|---|
| 5.396.1 (recombinant) | 10 mM Glycine pH 1.7 | 6 | 100 |
| 5.396.1 (Hc-S103N Lc-K61R) | 10 mM Glycine pH 1.7 | 9 | 100 |
| 6.605.1 (recombinant) | 10 mM Glycine pH 1.5 | 6 | 50 |
| 6.605.1 (Hc-H3Q, M13K, D82E Lc-T25A, T53S) | 10 mM Glycine pH 1.5 | 6 | 50 |
| 5.948.1 (recombinant) | 10 mM Glycine pH 1.5 | 12 | 50 |
| 5.948.1 (Hc-H100Y) | 10 mM Glycine pH 1.5 | 12 | 50 |

Results

All sensorgrams were fitted locally using BIA evaluation software 4.1 (BIAcore™) and Scrubber software version 2.0 (BioLogic Software). Anti-IgE antibodies of the invention show similar nanomolar affinity to IgE (see Table 18).

TABLE 18

Affinity values for the anti-IgE antibodies

| Anti-IgE Antibody | $K_D$ (affinity) | On rate $(k_a)$, $M^{-1} s^{-1}$ | Off rate $(k_d)$, $s^{-1}$ |
|---|---|---|---|
| 5.396.1 (recombinant) | 2.50 nM | $3.23 \times 10^4$ | $8.09 \times 10^{-5}$ |
| 5.396.1 (Hc-S103N Lc-K61R) | 3.95 nM | $2.36 \times 10^4$ | $9.29 \times 10^{-5}$ |
| 6.605.1 (recombinant) | 2.74 nM | $6.34 \times 10^4$ | $1.74 \times 10^{-4}$ |
| 6.605.1 (Hc-H3Q, M13K, D82E Lc-T25A, T53S) | 2.94 nM | $3.02 \times 10^4$ | $8.88 \times 10^{-5}$ |
| 5.948.1 (recombinant) | 1.32 nM | $2.36 \times 10^4$ | $3.11 \times 10^{-5}$ |
| 5.948.1 (Hc-H100Y) | 158.9 pM | $1.51 \times 10^5$ | $2.42 \times 10^{-5}$ |

Example 15

Identification of Epitope Selectivity

Assay Principle

BIAcore™ binning was used to map the relative epitopes recognized by the anti-IgE antibodies.

Protocol

Test anti-IgE antibodies (E25; recombinant 5.396.1; 5.396.1 Hc-S103N Lc-K61R; recombinant 6.605.1; 6.605.1 Hc-H3Q,M13K,D82E Lc-T25A, T53S; recombinant 5.948.1 and 5.948.1 Hc-H100Y) were immobilised onto separate flow cells of CM5 biosensor chips using the BIAcore™ 3000 instrument (BIAcore™, Uppsala, Sweden) and standard EDC-NHS amine coupling chemistry. The immobilisation buffer was 10 mM sodium acetate pH5.0. A protein density of approximately 1500 RU was achieved in all cases.

Epitope binning experiments were carried out using HBS-EP running buffer (0.01M HEPES pH7.4, 0.15M NaCl, 3 mM EDTA, 0.005% Polysorbate 20). Human IgE (5 µg/mL, Serotec, Cat. No. PHP008X2) was injected across the first flow cell, in a volume of 100 µL at a rate of 50 µl/min. After the injection was complete, the first antibody probe was added to the same flow cell. All probe antibodies were diluted to a concentration of approximately 10 µg/mL in HBS-EP, and injected in a volume of 100 µL at a flow rate of 50 µl/min. When no binding of the test antibody was observed, the next test clone was injected immediately afterwards. When binding did occur, the sensor surface was regenerated by injection of Glycine pH1.5 for 6 seconds. After regeneration, IgE was bound again and further test antibodies were injected. These procedures were carried out until the entire panel of clones had been injected over the surface of the immobilised antibody plus bound IgE. A new flow cell with a different immobilised antibody plus bound IgE was then used for probing with the test clones.

Results

Combinations of antibody pairs were tested in this way and a response matrix was created based on whether binding was observed (see Table 19 and FIG. 5). Epitope binning data suggests that some of the anti-IgE antibodies share overlapping epitopes while others have distinct epitopes.

TABLE 19

Epitope binning response matrix (x = no binding, ✓ = binding)

| Immobilised Antibody | 2° Ab E25 | 2° Ab 5.396.1 | 2° Ab 5.396.1 S103N/K61R | 2° Ab 6.605.1 | 2° Ab 6.605.1 QKE T25A T53S | 2° Ab 5.948.1 | 2° Ab 5.948.1 H100Y |
|---|---|---|---|---|---|---|---|
| E25 | x | x | x | ✓ | ✓ | x | x |
| 5.396.1 (recombinant) | x | x | x | x | x | x | NT |
| 5.396.1 (Hc-S103N Lc-K61R) | x | x | x | x | x | x | x |
| 6.605.1 (recombinant) | ✓ | x | x | x | x | ✓ | NT |
| 6.605.1 (Hc-H3Q, M13K, D82E Lc-T25A, T53S) | ✓ | ✓ | ✓ | x | x | ✓ | NT |
| 5.948.1 (recombinant) | x | x | x | ✓ | ✓ | x | x |
| 5.948.1 (Hc-H100Y) | x | NT | x | NT | NT | x | x |

Example 16

Identification of Species Cross-Reactivity

Assay Principle

ELISA and BIAcore™ experiments were used to measure the cross-reactivity of the anti-IgE monoclonal antibodies with IgE from dog, rat, mouse and cynomolgus monkey.

Protocol

Selectivity screening against dog, rat and mouse IgE was determined using BIAcore™. Purified dog (Bethyl, Cat. No. P115), rat (Serotec, Cat. No. PRP07A) and mouse IgE (Serotec, Cat. No. PMP68) were injected over covalently immobilized anti-IgE (E25; 5.396.1; 5.396.1 Hc-S103N Lc-K61R; 6.605.1; 6.605.1 Hc-H3Q,M13K,D82E Lc-T25A, T53S; and 5.948.1) in order to determine if IgE from these species cross-reacted. The anti-IgE antibodies of the invention were covalently immobilized onto a CM5 sensor chip using the BIAcore™ 3000 instrument (BIAcore™, Uppsala, Sweden) and standard EDC-NHS coupling chemistry. 10 mM sodium acetate pH5.0 was used as immobilization buffer and an immobilization binding response of 125 RU was achieved. The reference flow cell was activated (with EDC-NHS) and blocked (with Ethanolamine) but no protein was immobilized. Binding measurements were carried out in HBS-EP buffer (10 mM HEPES, 150 mM NaCl, 3 mM EDTA, 0.005% v/v Surfactant P20 pH 7.4, supplied by BIAcore™) at a flow rate of 100 µL/min using an IgE concentration of 30 µg/mL. Injection time for each IgE was 3.25 minutes. Human IgE (30 µg/mL, Serotec, Cat. No. PHP008×2) was also used as a positive control. The response level before and after injection of each IgE was obtained.

To measure cross-reactivity against cynomolgus monkey IgE, serum was used as the source of IgE and cross-reactivity tested using an ELISA methodology. Test anti-IgE (E25; 5.396.1; 5.396.1 Hc-S103N Lc-K61R; 6.605.1; 6.605.1 Hc-H3Q,M13K,D82E Lc-T25A, T53S; and 5.948.1) was coated onto Nunc Maxisorp™ 96-well plates (Fisher Scientific, Cat. No. DIS-971-010P) overnight in 50 mM TBS pH 8.0 (Sigma, Cat. No. T6664) at 2.5 µg/mL at 4° C. Wells were washed once with 150 µL/well wash buffer (0.05% Tween-20, Sigma, Cat. No. P7949/TBS) then blocked with 150 µL/well 1% BSA (Sigma, Cat. No. A7030) in TBS for 2 hours at room temperature. Wells were washed twice with 150 µL wash buffer. 50 µL human (in-house donors) or cynomolgus serum (Harlan Sera-Lab Ltd, Loughborough) was added from neat to at least 1:16 dilution in 1% BSA/0.05% Tween-20/TBS diluent buffer. Human serum IgE standard from NIBSC (National Institute for Biological Standards and Control, Cat. No. 75/502) was used as the standard in this assay and a standard curve of 3-200 ng/mL was used on each plate. Wells were incubated for 2 hours at 25° C. before washing (3×150 µL wash buffer). Bound IgE was detected using biotinylated polyclonal anti-IgE (Kirkegaard & Perry Laboratories, Cat. No. 16-10-04) diluted 1:1000 in diluent buffer. Wells were incubated for 1 hour at 25° C. then washed (3×150 µL wash buffer). Streptavidin-HRP (Amersham Bioscience, Cat. No. RPN 1231) diluted 1:1000 in diluent buffer was added to all wells and incubated for 45 minutes at room temperature. Wells were washed (3×150 µL wash buffer). 50 µL OPD (Dako, Cat. No. S2045) was added to all wells and the color allowed to develop for 10 minutes before stopping the reaction with 50 µl 0.6M $H_2SO_4$ and the absorbance measured at 490 nm. The concentration of IgE detected was calculated by plotting the NIBSC standard curve and extrapolating IgE concentrations from the standard curve. These values were then multiplied by the dilution factor to give IgE concentration in ng/mL. The ability of a capture antibody to bind cynomolgus IgE can be estimated by the concentration of IgE detected in the serum and directly compared with anti-IgE antibodies known to bind cynomolgus IgE.

Results

The binding experiments conducted by BIAcore™ demonstrated that none of the anti-IgE antibodies of the invention interacted with dog, rat or mouse IgE up to an IgE concentration of 30 µg/mL. An ELISA assay with cynomolgus monkey serum suggested that anti-IgE antibodies cross-reacted with cynomolgus IgE to varying extents. These data are presented in Table 20.

TABLE 20

IgE concentration (ng/mL) detected in 8 cynomolgus serum samples when anti-IgE monoclonal antibodies are used as the capture antibody. A human serum sample is used as control.

| | | Serum sample | | | | | | | | |
|---|---|---|---|---|---|---|---|---|---|---|
| | Capture antibody | Human serum | Cyno 1 | Cyno 2 | Cyno 3 | Cyno 4 | Cyno 5 | Cyno 6 | Cyno 7 | Cyno 8 |
| Test 1 | E25 | 250 | 172 | 52 | 166 | 13 | 232 | 30 | 0 | nd |
| | 5.396.1 (recombinant) | 385 | 30 | 0 | 27 | 0 | 37 | 3 | 0 | nd |
| | 5.396.1 (Hc-S103N Lc-K61R) | 399 | 41 | 0 | 39 | 0 | 57 | 0 | 0 | nd |
| | 6.605.1 (recombinant) | 397 | 120 | 91 | 107 | 0 | 140 | 0 | 0 | nd |
| | 6.605.1 (Hc-H3Q, M13K, D82E Lc-T25A, T53S) | 437 | 133 | 103 | 122 | 0 | 173 | 19 | 0 | nd |
| | 5.948.1 (Batch 2) (recombinant) | 468 | 481 | 464 | 457 | 39 | 837 | 53 | 8 | nd |
| Test 2 | E25 | 319 | 146 | 104 | 135 | 14 | 252 | 28 | 0 | 25 |
| | 5.396.1 (Hc-S103N Lc-K61R) | 357 | 57 | 39 | 53 | 0 | 102 | 0 | 0 | 0 |
| | 5.948.1 (Batch 2) (recombinant) | 431 | 289 | 328 | 309 | 38 | 630 | 62 | 0 | 56 |
| | 5.948.1 (Hc-H100Y) | 408 | 170 | 199 | 178 | 25 | 420 | 39 | 0 | 36 |

Example 17

List of Sequences for Antibodies of the Invention

TABLE 21

SEQ ID NOs for recombinant antibodies of the invention

Recombinant Abs Sequence identifiers SEQ ID NOs

| | | | 5.396.1 | 5.396.1 (Hc-S103N; Lc-K61R) | 6.605.1 | 6.605.1 (Hc-H3Q, M13K, D82E; Lc-T25A, T53S) | 5.948.1 | 5.948.1 (H100Y) |
|---|---|---|---|---|---|---|---|---|
| Heavy chain | Full length | DNA | 1 | 21 | 41 | 61 | 81 | 121 |
| | | protein | 2 | 22 | 42 | 62 | 82 | 122 |
| | Variable domain | DNA | 3 | 23 | 43 | 63 | 83 | 123 |
| | | protein | 4 | 24 | 44 | 64 | 84 | 124 |
| | CDR1 | DNA | 5 | 25 | 45 | 65 | 85 | 125 |
| | | protein | 6 | 26 | 46 | 66 | 86 | 126 |
| | CDR2 | DNA | 7 | 27 | 47 | 67 | 87 | 127 |
| | | protein | 8 | 28 | 48 | 68 | 88 | 128 |
| | CDR3 | DNA | 9 | 29 | 49 | 69 | 89 | 129 |
| | | protein | 10 | 30 | 50 | 70 | 90 | 130 |
| Light chain | Full length | DNA | 11 | 31 | 51 | 71 | 91 | 131 |
| | | protein | 12 | 32 | 52 | 72 | 92 | 132 |
| | Variable domain | DNA | 13 | 33 | 53 | 73 | 93 | 133 |
| | | protein | 14 | 34 | 54 | 74 | 94 | 134 |
| | CDR1 | DNA | 15 | 35 | 55 | 75 | 95 | 135 |
| | | protein | 16 | 36 | 56 | 76 | 96 | 136 |
| | CDR2 | DNA | 17 | 37 | 57 | 77 | 97 | 137 |
| | | protein | 18 | 38 | 58 | 78 | 98 | 138 |
| | CDR3 | DNA | 19 | 39 | 59 | 79 | 99 | 139 |
| | | protein | 20 | 40 | 60 | 80 | 100 | 140 |

TABLE 22

SEQ ID NOs for monoclonal antibodies of the invention mAbs from hybridomas Sequence identifiers SEQ ID NOs

| | | | 5.396.1 | 6.605.1 | 5.948.1 |
|---|---|---|---|---|---|
| Heavy chain | Full length | DNA | 101 | 105 | 109 |
| | | protein | 102 | 106 | 110 |
| Light chain | Full length | DNA | 103 | 107 | 111 |
| | | protein | 104 | 108 | 112 |

In the below sequences: Variable domains in UPPERCASE; CDRs underlined; Protein sequences derived by translation. In all sequences, the leader sequence was omitted.

```
                    5.396.1 produced by hybridoma
Nucleotide sequence of 5.396.1 heavy chain from hybridoma = SEQ ID NO: 101

CAGGTGCAGCTACAGCAGTGGGGCGCAGGACTGTTGAAGCCTTCGGAGACCCTGTCCCTCACCTG
CGCTGTCTATGGTGGGTCCTTCAGTGGTTACTACTGGAGCTGGATCCGCCAGCCCCCAGGGAAGGG
GCTGGAGTGGATTGGGGAAATCCATCATAGTGGAAGCACCAACTACAACCCGTCCCTCAAGAGTCG
AGTCACCATATCAGTAGACACGTCCAAGAACCAGTTCTCCCTGAAGCTGAGCTCTGTGACCGCCGC
GGACACGGCTGTGTATTACTGTGCGAGAGACAACTGGAACGACTCTTTCTACTACTACTACGGTATG
GACGTCTGGGGCCAAGGGACCACGGTCACCGTCTCCTCAgcctccaccaagggcccatcggtcttccccctggcgccc
tgctccaggagcacctccgagagcacagcggccctgggctgcctggtcaaggactacttccccgaaccggtgacggtgtcgtggaactcaggcg
ctctgaccagcggcgtgcacaccttcccagctgtcctacagtcctcaggactctactccctcagcagcgtggtgaccgtgccctccagcaacttcggc
acccagacctacacctgcaacgtagatcacaagcccagcaacaccaaggtggacaagacagttgagcgcaaatgttgtgtcgagtgcccaccgt
```

-continued

```
gcccagcaccacctgtggcaggaccgtcagtcttcctcttcccccaaaacccaaggacaccctcatgatctcccggacccctgaggtcacgtgcg
tggtggtggacgtgagccacgaagaccccgaggtccagttcaactggtacgtggacggcgtggaggtgcataatgccaagacaaagccacggg
aggagcagttcaacagcacgttccgtgtggtcagcgtcctcaccgttgtgcaccaggactggctgaacggcaaggagtacaagtgcaaggtctcc
aacaaaggcctcccagccccatcgagaaaaccatctccaaaaccaaagggcagccccgagaaccacaggtgtacaccctgcccccatcccg
ggaggagatgaccaagaaccaggtcagcctgacctgcctggtcaaaggcttctaccccagcgacatcgccgtggagtgggagagcaatgggca
gccggagaacaactacaagaccacacctcccatgctggactccgacggctccttcttcctctacagcaagctcaccgtggacaagagcaggtggc
agcaggggaacgtcttctcatgctccgtgatgcatgaggctctgcacaaccactacacgcagaagagcctctccctgtctccgggtaaa
```

Derived protein sequence of 5.396.1 heavy chain from hybridoma = SEQ ID NO: 102

```
QVQLQQWGAGLLKPSETLSLTCAVYGGSFSGYYWSWIRQPPGKGLEWIGEIHHSGSTNYNPSLKSRVTI
SVDTSKNQFSLKLSSVTAADTAVYYCARDNWNDSFYYYGMDVWGQGTTVTVSSastkgpsvfplapcsrstse
staalgclvkdyfpepvtvswnsgaltsgvhtfpavlqssglyslssvvtvpssnfgtqtytcnvdhkpsntkvdktverkccvecppcpappvagps
vflfppkpkdtlmisrtpevtcvvvdvshedpevqfnwyvdgvevhnaktkpreeqfnstfrvvsvltvvhqdwlngkeykckvsnkglpapiektis
ktkgqprepqvytlppsreemtknqvsltclvkgfypsdiavewesngqpennykttppmldsdgsfflyskltvdksrwqqgnvfscsvmhealh
nhytqkslslspgk
```

Nucleotide sequence of 5.396.1 light chain from hybridoma = SEQ ID NO: 103

```
GACATCCAGATGACCCAGTCTCCATCATCACTGTCTGCATCTGTAGGAGACAGAGTCACCATCACAT
GTCGGGCGAGTCAGGGCATTAGCAATCATTTAGCCTGGTTTCAGCAGAAACCAGGGAAAGCCCCTA
AGTCCCTGATCTATGCTGCATCCAGTTTGCAAAGTGGGGTCCCATCAAAGTTCAGCGGCAGTGGATC
TGGGACAGATTTCACTCTCACCATCAGCAGCCTGCAGCCTGAAGATTTTGCAACTTATTACTGCCAAC
AGTATAATAGGCACCCATTCACTTTCGGCCCTGGGACCAAAGTGGATATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt
```

Derived protein sequence of 5.396.1 light chain from hybridoma = SEQ ID NO: 104

```
DIQMTQSPSSLSASVGDRVTITCRASQGISNHLAWFQQKPGKAPKSLIYAASSLQSGVPSKFSGSGSGTD
FTLTISSLQPEDFATYYCQQYNRHPFTFGPGTKVDIKrtvaapsvfifppsdeqlksgtasvvcllnnfypreakvqwkvdnalq
sgnsqesvteqdskdstyslsstltlskadyekhkvyacevthqglsspvtksfnrgec
```

6.605.1 produced by hybridoma

Nucleotide sequence of 6.605.1 heavy chain from hybridoma = SEQ ID NO: 105

```
CAGGTTCACCTGGTGCAGTCTGGAGCTGAGGTGAAGATGCCTGGGGCCTCAGTGAAGGTCTCCTGC
AAGGCTTCTGGTTACACCTTTACCAGCTATGGTATCAGCTGGGTGCGACAGGCCCCTGGACAAGGG
CTTGAGTGGATGGGATGGATCAGCGCTTACAATGGTAACACAAACTATGCACAGAAGCTCCAGGGC
AGAATCACCATGACCACAGACACATCCACGAGCACAGCCTACATGGACCTGAGGAGCCTGAGATCT
GACGACACGGCCGTGTATTACTGTGCGAGAGATGGGGATTACTATGATCCTTTTGACTACTGGGGCC
AGGGAACCCTGGTCACCGTCTCCTCAgcctccaccaagggcccatcggtcttccccctggcgccctgctccaggagcacctccg
agagcacagcggccctgggctgcctggtcaaggactacttccccgaaccggtgacggtgtcgtggaactcaggcgctctgaccagcggcgtgca
caccttcccagctgtcctacagtcctcaggactctactccctcagcagcgtggtgaccgtgccctccagcaacttcggcacccagacctacacctgc
aacgtagatcacaagcccagcaacaccaaggtggacaagacagttgagcgcaaatgttgtgtcgagtgcccaccgtgcccagcaccacctgtg
gcaggaccgtcagtcttcctcttcccccaaaacccaaggacaccctcatgatctcccggacccctgaggtcacgtgcgtggtggtggacgtgagc
cacgaagaccccgaggtccagttcaactggtacgtggacggcgtggaggtgcataatgccaagacaaaaccgcgggaggagcagttcaacag
cacgttccgtgtggtcagcgtcctcaccgttgtgcaccaggactggctgaacggcaaggagtacaagtgcaaggtctccaacaaaggcctcccag
cccccatcgagaaaaccatctccaaaaccaaagggcagccccgagaaccacaggtgtacaccctgcccccatcccgggaggagatgaccaa
gaaccaggtcagcctgacctgcctggtcaaaggcttctaccccagcgacatcgccgtggagtgggagagcaatgggcagccggagaacaacta
caagaccacacctcccatgctggactccgacggctccttcttcctctacagcaagctcaccgtggacaagagcaggtggcagcaggggaacgtct
tctcatgctccgtgatgcatgaggctctgcacaaccactacacgcagaagagcctctccctgtctccgggtaaa
```

Derived protein sequence of 6.605.1 heavy chain from hybridoma = SEQ ID NO: 106

```
QVHLVQSGAEVKMPGASVKVSCKASGYTFTSYGISWVRQAPGQGLEWMGWISAYNGNTNYAQKLQGR
ITMTTDTSTSTAYMDLRSLRSDDTAVYYCARDGDYYDPFDYWGQGTLVTVSSastkgpsvfplapcsrstsestaal
gclvkdyfpepvtvswnsgaltsgvhtfpavlqssglyslssvvtvpssnfgtqtytcnvdhkpsntkvdktverkccvecppcpappvagpsvflfp
pkpkdtlmisrtpevtcvvvdvshedpevqfnwyvdgvevhnaktkpreeqfnstfrvvsvltvvhqdwlngkeykckvsnkglpapiektisktkg
qprepqvytlppsreemtknqvsltclvkgfypsdiavewesngqpennykttppmldsdgsfflyskltvdksrwqqgnvfscsvmhealhnhyt
qkslslspgk
```

Nucleotide sequence of 6.605.1 light chain from hybridoma = SEQ ID NO: 107

```
GACATCCAGATGACCCAGTCTCCATCCTCCCTGTCTGCATCTGTAGGAGACAGAGTCACCATCACTT
GCCGGACAAGTCAGAGTATTAGCAACTGGTTAAATTGGTATCAGCAGAAACCAGGGAAAGCCCCTAA
ACTCCTGATCTATGGTGCCTCCACTTTGAAAAGTGGGGTCCCATCAAGGTTCAGTGGCAGTGAATCT
GGGACAGATTTCACTCTCACCATCAGCAGTCTGCAACCTGAAGATTTTGCAACTTACTACTGTCAACA
GAGTTACAGTACCCCTCCGACGTTCGGCCAAGGGACCAAGGTGGAAATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt
```

Derived protein sequence of 6.605.1 light chain from hybridoma = SEQ ID NO: 108

DIQMTQSPSSLSASVGDRVTITC<u>RTSQSISNWLN</u>WYQQKPGKAPKLLIY<u>GASTLKS</u>GVPSRFSGSESGTD
FTLTISSLQPEDFATYYC<u>QQSYSTPPT</u>FGQGTKVEIKrtvaapsvfifppsdeqlksgtasvvcllnnfypreakvqwkvdnalq
sgnsqesvteqdskdstyslsstltlskadyekhkvyacevthqglsspvtksfnrgec

5.948.1 produced by hybridoma

Nucleotide sequence of 5.948.1 heavy chain from hybridoma = SEQ ID NO: 109

CAGGTGCAGCTGGTGCAGTCTGGGGCTGAGGTGAAGAAGCCTGGGGCCTCAGTGAAGGTCTCCTG
CAAGGCTTCTGGATACACCTTCACC<u>AGTTATGATATCAACT</u>GGGTGCGACAGGCCACTGGACAAGG
GCTTGAGTGGATGGGA<u>TGGATGGACCCTAACAGTGGTAACACAGGCTATGCACAGAAGTTCCAGGG
C</u>AGAGTCACCATGACCAGGAACACCTCCATAAGCACAGCCTACATGGAGCTGAGCAGCCTGAGATC
TGAGGACACGGCCGTGTATTACTGTGCGAGA<u>GCCCACTATGATAGTGATGGTTATTACTTCTCC
GGTATGGACGTCT</u>GGGGCCAAGGGACCACGGTCACCGTCTCCTCAgcctccaccaagggcccatcggtcttcccc
ctggcgccctgctccaggagcacctccgagagcacagcggccctgggctgcctggtcaaggactacttccccgaaccggtgacggtgtcgtgga
actcaggcgctctgaccagcggcgtgcacaccttcccagctgtcctacagtcctcaggactctactccctcagcagcgtggtgaccgtgccctccag
caacttcggcacccagacctacacctgcaacgtagatcacaagcccagcaacaccaaggtggacaagacagttgagcgcaaatgttgtgtcga
gtgcccaccgtgcccagcaccacctgtggcaggaccgtcagtcttcctcttccccccaaaacccaaggacaccctcatgatctcccggacccctga
ggtcacgtgcgtggtggtggacgtgagccacgaagaccccgaggtccagttcaactggtacgtggacggcgtggaggtgcataatgccaagaca
aagccacgggaggagcagttcaacagcacgttccgtgtggtcagcgtcctcaccgttgtgcaccaggactggctgaacggcaaggagtacaagt
gcaaggtctccaacaaaggcctcccagcccccatcgagaaaaccatctccaaaaccaaagggcagccccgagaaccacaggtgtacaccctg
cccccatcccgggaggagatgaccaagaaccaggtcagcctgacctgcctggtcaaaggcttctaccccagcgacatcgccgtggagtgggagag
caatgggcagccggagaacaactacaagaccacacctcccatgctggactccgacggctccttcttcctctacagcaagctcaccgtggacaa
gagcaggtggcagcaggggaacgtcttctcatgctccgtgatgcatgaggctctgcacaaccactacacgcagaagagcctctccctgtctccggg
taaa Derived protein sequence of 5.948.1 heavy chain from hybridoma = SEQ ID NO: 110

QVQLVQSGAEVKKPGASVKVSCKASGYTFT<u>SYDINW</u>VRQATGQGLEWMG<u>WMDPNSGNTGYAQKFQG</u>
RVTMTRNTSISTAYMELSSLRSEDTAVYYCAR<u>GHYDSDGYYSFSGMDV</u>WGQGTTVTVSSastkgpsvfplap
csrstsestaalgclvkdyfpepvtvswnsgaltsgvhtfpavlqssglyslssvvtvpssnfgtqtytcnvdhkpsntkvdktverkccvecppcpap
pvagpsvflfppkpkdtlmisrtpevtcvvvdvshedpevqfnwyvdgvevhnaktkpreeqfnstfrvvsvltvvhqdwlngkeykckvsnkglp
apiektisktkgqprepqvytlppsreemtknqvsltclvkgfypsdiavewesngqpennyktttppmldsdgsfflyskltvdksrwqqgnvfscsv
mhealhnhytqkslslspgk Nucleotide sequence of 5.948.1 light chain from hybridoma = SEQ ID NO: 111

GATATTGTGATGACTCAGTCTCCACTCTCCCTGCCCGTCACCCCTGGAGAGCCGGCCTCCATCTCCT
GT<u>AGGTCTAGTCAGAGCCTCCTGCATAGGAATGGATACAACTACTTGGAT</u>TGGTACCTGCAGAAGCC
AGGGCAGTCTCCACAGCTCCTGATCTATT<u>TGGGTTCTAATCGGGCCTCC</u>GGGGTCCCTGACAGGTT
CAGTGGCAGTGGATCAGGCACAGATTTTACACTGAAAATCAGCGAGTCGAGGATGTTGG
GGTTTATTACTGC<u>ATGCAAGCTCTACAAACTCCTCCGGCCA</u>CTTTCGGCGGAGGGACCAAGGTGGA
GATCAAAcgaactgtggctgcaccatctgtcttcatcttcccgccatctgatgagcagttgaaatctggaactgcctctgttgtgtgcctgctgaataa
cttctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatcagg
gcctgagctcgcccgtcacaaagagcttcaacaggggagagtgt Derived protein sequence of 5.948.1 light chain from hybridoma = SEQ ID NO: 112

DIVMTQSPLSLPVTPGEPASISC<u>RSSQSLLHRNGYNYLD</u>WYLQKPGQSPQLLIY<u>LGSNRAS</u>GVPDRFSGS
GSGTDFTLKISRVEAEDVGVYYC<u>MQALQTPPAT</u>FGGGTKVEIKrtvaapsvfifppsdeqlksgtasvvcllnnfypreakv
qwkvdnalqsgnsqesvteqdskdstyslsstltlskadyekhkvyacevthqglsspvtksfnrgec

Recombinant 5.396.1

Nucleotide sequence of recombinant 5.396.1 heavy chain = SEQ ID NO: 1

CAGGTGCAGCTACAGCAGTGGGGCGCAGGACTGTTGAAGCCTTCGGAGACCCTGTCCCTCACCTG
CGCTGTCTATGGTGGGTCCTTCAGT<u>GGTTACTACTGGAGCT</u>GGATCCGCCAGCCCCCAGGGAAGGG
GCTGGAGTGGATTGGG<u>GAAATCCATCATAGTGGAAGCACCAACTACAACCCGTCCCTCAAGAGTCG
</u>AGTCACCATATCAGTAGACACGTCCAAGAACCAGTTCTCCCTGAAGCTGAGCTCTGTGACCGCCGC
GGACACGGCTGTGTATTACTGTGCGAGA<u>7ryeryetyrtyrtyGACAACTGGAACGACTCTTTCTACTACTACTACGGTATG
GACGTCT</u>GGGGCCAAGGGACCACGGTCACCGTCTCCTCAgcctccaccaagggcccatcggtcttccccctggcgccc
tgctccaggagcacctccgagagcacagcggccctgggctgcctggtcaaggactacttccccgaaccggtgacggtgtcgtggaactcaggcg
ctctgaccagcggcgtgcacaccttcccggctgtcctacagtcctcaggactctactccctcagcagcgtagtgaccgtgccctccagcaacttcggc
acccagacctacacctgcaacgtagatcacaagcccagcaacaccaaggtggacaagacagttgagcgcaaatgttgtgtcgagtgcccaccgt
gcccagcaccacctgtggcaggaccgtcagtcttcctcttccccccaaaacccaaggacaccctcatgatctcccggacccctgaggtcacgtgcg
tggtggtggacgtgagccacgaagaccccgaggtccagttcaactggtacgtggacggcgtggaggtgcataatgccaagacaaagccacgg
gaggagcagttcaacagcacgttccgtgtggtcagcgtcctcaccgtcgtgcaccaggactggctgaacggcaaggagtacaagtgcaaggtctcc
aacaaaggcctcccagcccccatcgagaaaaccatctccaaaaccaaagggcagccccgagaaccacaggtgtacaccctgcccccatcccg
ggaggagatgaccaagaaccaggtcagcctgacctgcctggtcaaaggcttctaccccagcgacatcgccgtggagtgggagagcaatgggca
gccggagaacaactacaagaccacacctcccatgctggactccgacggctccttcttcctctacagcaagctcaccgtggacaagagcaggtggc
agcaggggaacgtcttctcatgctccgtgatgcatgaggctctgcacaaccactacacacagaagagcctctccctgtctccgggtaaa Derived protein sequence of recombinant 5.396.1 heavy chain = SEQ ID NO: 2

QVQLQQWGAGLLKPSETLSLTCAVYGGSF<u>SGYYWS</u>WIRQPPGKGLEWIG<u>EIHHSGSTNYNPSLKSR</u>VTI
SVDTSKNQFSLKLSSVTAADTAVYYCAR<u>DNWNDSFYYYYGMDV</u>WGQTTVTVSSastkgpsvfplapcsrstse
staalgclvkdyfpepvtvswnsgaltsgvhtfpavlqssglyslssvvtvpssnfgtqtytcnvdhkpsntkvdktverkccvecppcpappvagps
vflfppkpkdtlmisrtpevtcvvvdvshedpevqfnwyvdgvevhnaktkpreeqfnstfrvvsvltvvhqdwlngkeykckvsnkglpapiektis
ktkgqprepqvytlppsreemtknqvsltclvkgfypsdiavewesngqpennykttppmldsdgsfflyskltvdksrwqqgnvfscsvmhealh
nhytqkslslspgk Nucleotide sequence of recombinant 5.396.1 light chain = SEQ ID NO: 11

GACATCCAGATGACCCAGTCTCCATCATCACTGTCTGCATCTGTAGGAGACAGAGTCACCATCACAT
GT<u>CGGGCGAGTCAGGGCATTAGCAATCATTTAGCC</u>TGGTTTCAGCAGAAACCAGGGAAAGCCCCTA
AGTCCCTGATCTAT<u>GCTGCATCCAGTTTGCAAAGT</u>GGGGTCCCATCAAGTTCAGCGGCAGTGGATC
TGGGACAGATTTCACTCTCACCATCAGCAGCCTGCAGCCTGAAGATTTTGCAACTTATTACTGC<u>CAAC
AGTATAATAGGCACCCATTCACT</u>TTCGGCCCTGGGACCAAAGTGGATATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt Derived protein sequence of recombinant 5.396.1 light chain = SEQ ID NO: 12

DIQMTQSPSSLSASVGDRVTITC<u>RASQGISNHLA</u>WFQQKPGKAPKSLIY<u>AASSLQS</u>GVPSKFSGSGSGTD
FTLTISSLQPEDFATYYC<u>QQYNRHPFT</u>FGPGTKVDIKrtvaapsvfifppsdeqlksgtasvvcllnnfypreakvqwkvdnalq
sgnsqesvteqdskdstyslsstltlskadyekhkvyacevthqglsspvtksfnrgec

Recombinant 5.396.1 (Hc-S103N Lc-K61R)

Nucleotide sequence of recombinant 5.396.1 (S103N) heavy chain=SEQ ID NO: 21

CAGGTGCAGCTACAGCAGTGGGGCGCAGGACTGTTGAAGCCTTCGGAGACCCTGTCCCTCACCTG
CGCTGTCTATGGTGGGTCCTTCAGT<u>GGTTACTACTGGAGC</u>TGGATCCGCCAGCCCCCAGGGAAGGG
GCTGGAGTGGATTGGG<u>GAAATCCATCATAGTGGAAGCACCAACTACAACCCGTCCCTCAAGAGTCG</u>
AGTCACCATATCAGTAGACACGTCCAAGAACCAGTTCTCCCTGAAGCTGAGCTCTGTGACCGCCGC
GGACACGGCCGTGTATTACTGTGCGAGA<u>44444444GACAACTGGAACGACAACTTCTACTACTACTACGGTATG
GACGTC</u>TGGGGCCAAGGGACCACGGTCACCGTCTCCTCAgcctccaccaagggcccatcggtcttccccctggcgccc
tgctccaggagcacctccgagagcacagcggccctgggctgcctggtcaaggactacttccccgaaccggtgacggtgtcgtggaactcaggcg
ctctgaccagcggcgtgcacaccttcccggctgtcctacagtcctcaggactctactccctcagcagcgtagtgaccgtgccctccagcagcttcggc
acccagacctacacctgcaacgtagatcacaagcccagcaacaccaaggtggacaagacagttgagcgcaaatgttgtgtcgagtgcccaccgt
gcccagcaccacctgtggcaggaccgtcagtcttcctcttccccccaaaacccaaggacaccctcatgatctcccggacccctgaggtcacgtgcg
tggtggtggacgtgagccacgaagaccccgaggtccagttcaactggtacgtggacggcgtggaggtgcataatgccaagacaaagccacggg
aggagcagttcaacagcacgttccgtgtggtcagcgtcctcaccgtcgtgcaccaggactggctgaacggcaaggagtacaagtgcaaggtctcc
aacaaaggcctcccagcccccatcgagaaaaccatctccaaaaccaaagggcagccccgagaaccacaggtgtacaccctgcccccatcccg
ggaggagatgaccaagaaccaggtcagcctgacctgcctggtcaaaggcttctaccccagcgacatcgccgtggagtgggagagcaatgggca
gccggagaacaactacaagaccacacctcccatgctggactccgacggctccttcttcctctacagcaagctcaccgtggacaagagcaggtggc
agcaggggaacgtcttctcatgctccgtgatgcatgaggctctgcacaaccactacacacagaagagcctctccctgtctccgggtaaa Derived protein sequence of recombinant 5.396.1 (S103N) heavy chain = SEQ ID NO: 22

QVQLQQWGAGLLKPSETLSLTCAVYGGSF<u>SGYYWS</u>WIRQPPGKGLEWIG<u>EIHHSGSTNYNPSLKSR</u>VTI
SVDTSKNQFSLKLSSVTAADTAVYYCAR<u>DNWNDNFYYYYGMDV</u>WGQTTVTVSSastkgpsvfplapcsrstse
staalgclvkdyfpepvtvswnsgaltsgvhtfpavlqssglyslssvvtvpssnfgtqtytcnvdhkpsntkvdktverkccvecppcpappvagps
vflfppkpkdtlmisrtpevtcvvvdvshedpevqfnwyvdgvevhnaktkpreeqfnstfrvvsvltvvhqdwlngkeykckvsnkglpapiektis
ktkgqprepqvytlppsreemtknqvsltclvkgfypsdiavewesngqpennykttppmldsdgsfflyskltvdksrwqqgnvfscsvmhealh
nhytqkslslspgk Nucleotide sequence of recombinant 5.396.1 (K61R) light chain = SEQ ID NO: 31

GACATCCAGATGACCCAGTCTCCATCATCACTGTCTGCATCTGTAGGAGACAGAGTCACCATCACAT
GT<u>CGGGCGAGTCAGGGCATTAGCAATCATTTAGCC</u>TGGTTTCAGCAGAAACCAGGGAAAGCCCCTA
AGTCCCTGATCTAT<u>GCTGCATCCAGTTTGCAAAGT</u>GGGGTCCCATCAAGTTCAGCGGCAGTGGATC
TGGGACAGATTTCACTCTCACCATCAGCAGCCTGCAGCCTGAAGATTTTGCAACTTATTACTGC<u>CAAC
AGTATAATAGGCACCCATTCACT</u>TTCGGCCCTGGGACCAAAGTGGATATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt Derived protein sequence of recombinant 5.396.1 (K61R) light chain = SEQ ID NO: 32

DIQMTQSPSSLSASVGDRVTITC<u>RASQGISNHLA</u>WFQQKPGKAPKSLIY<u>AASSLQS</u>GVPSRFSGSGSGTD
FTLTISSLQPEDFATYYC<u>QQYNRHPFT</u>FGPGTKVDIKrtvaapsvfifppsdeqlksgtasvvcllnnfypreakvqwkvdnalq
sgnsqesvteqdskdstyslsstltlskadyekhkvyacevthqglsspvtksfnrgec -continued Recombinant 6.605.1

Nucleotide sequence of recombinant 6.605.1 heavy chain = SEQ ID NO: 41

CAGGTTCACCTGGTGCAGTCTGGAGCTGAGGTGAAGATGCCTGGGGCCTCAGTGAAGGTCTCCTGC
AAGGCTTCTGGTTACACCTTTACC<u>AGCTATGGTATCAGC</u>TGGGTGCGACAGGCCCCTGGACAAGGG
CTTGAGTGGATGGGA<u>TGGATCAGCGCTTACAATGGTAACACAAACTATGCACAGAAGCTCCAGGGC</u>
AGAATCACCATGACCACAGACACATCCACGAGCACAGCCTACATGGACCTGAGGAGCCTGAGATCT
GACGACACGGCCGTGTATTACTGTGCGAGA<u>GATGGGGATTACTATGATCCTTTTGACTAC</u>TGGGGCC
AGGGAACCCTGGTCACCGTCTCCTCAgcctccaccaagggcccatcggtcttcccctggcgccctgctccaggagcacctccg
agagcacagcggccctgggctgcctggtcaaggactacttccccgaaccggtgacggtgtcgtggaactcaggcgctctgaccagcggcgtgca
caccttcccggctgtcctacagtcctcaggactctactccctcagcagcgtagtgaccgtgccctccagcaacttcggcacccagacctacacctgc
aacgtagatcacaagcccagcaacaccaaggtggacaagacagttgagcgcaaatgttgtgtcgagtgcccaccgtgcccagcaccacctgtg
gcaggaccgtcagtcttcctcttccccccaaaacccaaggacaccctcatgatctcccggacccctgaggtcacgtgcgtggtggtggacgtgagc
cacgaagaccccgaggtccagttcaactggtacgtggacggcgtggaggtgcataatgccaagacaaagccacgggaggagcagttcaacag
cacgttccgtgtggtcagcgtcctcaccgtcgtgcaccaggactggctgaacggcaaggagtacaagtgcaaggtctccaacaaaggcctcccag
ccccatcgagaaaaccatctccaaaaccaaagggcagccccgagaaccacaggtgtacaccctgccccatcccgggaggagatgaccaa
gaaccaggtcagcctgacctgcctggtcaaaggcttctaccccagcgacatcgccgtggagtgggagagcaatgggcagccggagaacaacta
caagaccacacctcccatgctggactccgacggctccttcttcctctacagcaagctcaccgtggacaagagcaggtggcagcaggggaacgtct
tctcatgctccgtgatgcatgaggctctgcacaaccactacacacagaagagcctctccctgtctccgggtaaa Derived protein sequence of recombinant 6.605.1 heavy chain = SEQ ID NO: 42

QVHLVQSGAEVKMPGASVKVSCKASGYTFT<u>SYGIS</u>WVRQAPGQGLEWMG<u>WISAYNGNTNYAQKLQGR</u>
ITMTTDTSTSTAYMDLRSLRSDDTAVYYCAR<u>DGDYYDPFDY</u>WGQGTLVTVSSastkgpsvfplapcsrstsestaal
gclvkdyfpepvtvswnsgaltsgvhtfpavlqssglyslssvvtvpssnfgtqtytcnvdhkpsntkvdktverkccvecppcpappvagpsvflfp
pkpkdtlmisrtpevtcvvvdvshedpevqfnwyvdgvevhnakktkpreeqfnstfrvvsvltvvhqdwlngkeykckvsnkglpapiektisktkg
qprepqvytlppsreemtknqvsltclvkgfypsdiavewesngqpennykttppmldsdgsfflyskltvdksrwqqgnvfscsvmhealhnhyt
qkslslspgk Nucleotide sequence of recombinant 6.605.1 light chain = SEQ ID NO: 51

GACATCCAGATGACCCAGTCTCCATCCTCCCTGTCTGCATCTGTAGGAGACAGAGTCACCATCACTT
GC<u>CGGACAAGTCAGAGTATTAGCAACTGGTTAAAT</u>TGGTATCAGCAGAAACCAGGGAAAGCCCCTAA
ACTCCTGATCTATGGTGCCTCCACTTTGAAAAGTGGGGTCCCATCAAGGTTCAGTGGCAGTGAATCT
GGGACAGATTTCACTCTCACCATCAGCAGTCTGCAACCTGAAGATTTTGCAACTTACTACTGT<u>CAACA
GAGTTACAGTACCCCTCCGAC</u>GTTCGGCCAAGGGACCAAGGTGGAAATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt Derived protein sequence of recombinant 6.605.1 light chain = SEQ ID NO: 52

DIQMTQSPSSLSASVGDRVTITC<u>RTSQSISNWLN</u>WYQQKPGKAPKLLIY<u>GASTLKS</u>GVPSRFSGSESGTD
FTLTISSLQPEDFATYYC<u>QQSYSTPPT</u>FGQGTKVEIKrtvaapsvfifppsdeqlksgtasvvcllnnfypreakvqwkvdnalq
sgnsqesvteqdskdstyslsstltlskadyekhkvyacevthqglsspvtksfnrgec Recombinant 6.605.1 (Hc- H3Q, M13K, D82E Lc- T25A,T53S)

Nucleotide sequence of recombinant 6.605.1 (H3Q, M13K, D82E) heavy chain = SEQ ID NO: 61

CAGGTCCAGCTGGTGCAGTCTGGAGCTGAGGTGAAGAAGCCTGGGGCCTCAGTGAAGGTCTCCTG
CAAGGCTTCTGGTTACACCTTTACC<u>AGCTATGGTATCAGC</u>TGGGTGCGACAGGCCCCTGGACAAGG
GCTTGAGTGGATGGGA<u>TGGATCAGCGCTTACAATGGTAACACAAACTATGCACAGAAGCTCCAGGG
C</u>AGAATCACCATGACCACAGACACATCCACGAGCACAGCCTACATGGAACTGAGGAGCCTGAGATC
TGACGACACGGCCGTGTATTACTGTGCGAGA<u>GATGGGGATTACTATGATCCTTTTGACTAC</u>TGGGGC
CAGGGAACCCTGGTCACCGTCTCCTCAgcctccaccaagggcccatcggtcttcccctggcgccctgctccaggagcacctcc
gagagcacagcggccctgggctgcctggtcaaggactactccccgaaccggtgacggtgtcgtggaactcaggcgctctgaccagcggcgtgc
acaccttcccggctgtcctacagtcctcaggactctactccctcagcagcgtagtgaccgtgccctccagcaacttcggcacccagacctacacctg
caacgtagatcacaagcccagcaacaccaaggtggacaagacagttgagcgcaaatgttgtgtcgagtgcccaccgtgcccagcaccacctgtg
gcaggaccgtcagtcttcctcttccccccaaaacccaaggacaccctcatgatctcccggacccctgaggtcacgtgcgtggtggtggacgtgagc
cacgaagaccccgaggtccagttcaactggtacgtggacggcgtggaggtgcataatgccaagacaaagccacgggaggagcagttcaacag
cacgttccgtgtggtcagcgtcctcaccgtcgtgcaccaggactggctgaacggcaaggagtacaagtgcaaggtctccaacaaaggcctcccag
ccccatcgagaaaaccatctccaaaaccaaagggcagccccgagaaccacaggtgtacaccctgccccatcccgggaggagatgaccaa
gaaccaggtcagcctgacctgcctggtcaaaggcttctaccccagcgacatcgccgtggagtgggagagcaatgggcagccggagaacaacta
caagaccacacctcccatgctggactccgacggctccttcttcctctacagcaagctcaccgtggacaagagcaggtggcagcaggggaacgtct
tctcatgctccgtgatgcatgaggctctgcacaaccactacacacagaagagcctctccctgtctccgggtaaa Derived protein sequence of recombinant 6.605.1 (H3Q, M13K, D82E) heavy chain = SEQ ID NO: 62

QVQLVQSGAEVKKPGASVKVSCKASGYTFT<u>SYGIS</u>WVRQAPGQGLEWMG<u>WISAYNGNTNYAQKLQGR</u>
ITMTTDTSTSTAYMELRSLRSDDTAVYYCAR<u>DGDYYDPFDY</u>WGQGTLVTVSSastkgpsvfplapcsrstsestaal
gclvkdyfpepvtvswnsgaltsgvhtfpavlqssglyslssvvtvpssnfgtqtytcnvdhkpsntkvdktverkccvecppcpappvagpsvflfp
pkpkdtlmisrtpevtcvvvdvshedpevqfnwyvdgvevhnakktkpreeqfnstfrvvsvltvvhqdwlngkeykckvsnkglpapiektisktkg
qprepqvytlppsreemtknqvsltclvkgfypsdiavewesngqpennykttppmldsdgsfflyskltvdksrwqqgnvfscsvmhealhnhyt
qkslslspgk Nucleotide sequence of recombinant 6.605.1 (T25A, T53S) light chain = SEQ ID NO: 71

GACATCCAGATGACCCAGTCTCCATCCTCCCTGTCTGCATCTGTAGGAGACAGAGTCACCATCACTT
GC<u>CGGGCAAGTCAGAGTATTAGCAACTGGTTAAAT</u>TGGTATCAGCAGAAACCAGGGAAAGCCCCTAA
ACTCCTGATCTATG<u>GTGCCTCCAGTTTGAAAAGT</u>GGGGTCCCATCAAGGTTCAGTGGCAGTGAATCT
GGGACAGATTTCACTCTCACCATCAGCAGTCTGCAACCTGAAGATTTTGCAACTTACTACTGT<u>CAACA
GAGTTACAGTACCCCTCCGAC</u>GTTCGGCCAAGGGACCAAGGTGGAAATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt Derived protein sequence of recombinant 6.605.1 (T25A, T53S) light chain = SEQ ID NO: 72

DIQMTQSPSSLSASVGDRVTITCR<u>ASQSISNWLN</u>WYQQKPGKAPKLLIY<u>GASSLKS</u>GVPSRFSGSESGT
DFTLTISSLQPEDFATYYC<u>QQSYSTPPT</u>FGQGTKVEIKrtvaapsvfifppsdeqlksgtasvvcllnnfypreakvqwkvdnal
qsgnsqesvteqdskdstyslsstltlskadyekhkvyacevthqglsspvtksfnrgec Recombinant 5.948.1

Nucleotide sequence of recombinant 5.948.1 heavy chain = SEQ ID NO: 81

CAGGTGCAGCTGGTGCAGTCTGGGGCTGAGGTGAAGAAGCCTGGGGCCTCAGTGAAGGTCTCCTG
CAAGGCTTCTGGATACACCTTCACC<u>AGTTATGATATCAACTGGGTGCGACAGGCCACTGGACAAGG
GCTTGAGTGGATGGGA</u><u>TGGATGGACCCTAACAGTGGTAACACAGGCTATGCACAGAAGTTCCAGGG
C</u>AGAGTCACCATGACCAGGAACACCTCCATAAGCACAGCCTACATGGAGCTGAGCAGCCTGAGATC
TGAGGACACGGCCGTGTATTACTGTGCGAGA<u>77777777GGCCACTATGATAGTGATGGTTATTACTCCTTCTCC
GGTATGGACGTC</u>TGGGGCCAAGGGACCACGGTCACCGTCTCCTCAgcctccaccaagggcccatcggtcttcccc
ctggcgccctgctccaggagcacctccgagagcacagcggccctgggctgcctggtcaaggactacttccccgaaccggtgacggtgtcgtgga
actcaggcgctctgaccagcggcgtgcacaccttcccggctgtcctacagtcctcaggactctactccctcagcagcgtagtgaccgtgccctccag
caacttcggcacccagacctacacctgcaacgtagatcacaagcccagcaacaccaaggtggacaagacagttgagcgcaaatgttgtgtcga
gtgcccaccgtgcccagcaccacctgtggcaggacccgtcagtcttcctcttcccccccaaaacccaaggacaccctcatgatctcccggacccctga
ggtcacgtgcgtggtggtggacgtgagccacgaagaccccgaggtccagttcaactggtacgtggacggcgtggaggtgcataatgccaagaca
aagccacgggaggagcagttcaacagcacgttccgtgtggtcagcgtcctcaccgtcgtgcaccaggactggctgaacggcaaggagtacaagt
gcaaggtctccaacaaaggcctcccagcccccatcgagaaaaccatctccaaaaccaaagggcagccccgagaaccacaggtgtacaccctg
ccccatcccgggaggagatgaccaagaaccaggtcagcctgacctgcctggtcaaaggcttctaccccagcgacatcgccgtggagtgggag
agcaatgggcagccggagaacaactacaagaccacacctcccatgctggactccgacggctccttcttcctctacagcaagctcaccgtggacaa
gagcaggtggcagcaggggaacgtcttctcatgctccgtgatgcatgaggctctgcacaaccactacacagaagagcctctccctgtctccggg
taaa Derived protein sequence of recombinant 5.948.1 heavy chain = SEQ ID NO: 82

QVQLVQSGAEVKKPGASVKVSCKASGYTFT<u>SYDIN</u>WVRQATGQGLEWMG<u>WMDPNSGNTGYAQKFQG</u>
RVTMTRNTSISTAYMELSSLRSEDTAVYYCAR<u>GHYDSDGYYSFSGMDVW</u>GQGTTVTVSSastkgpsvfplap
csrstsestaalgclvkdyfpepvtvswnsgaltsgvhtfpavlqssglyslssvvtvpssnfgtqtytcnvdhkpsntkvdktverkccvecppcpap
pvagpsvflfppkpkdtlmisrtpevtcvvvdvshedpevqfnwridgvevhnaktkpreeqfnstfrvvsvltvvhqdwlngkeykckvsnkglp
apiektisktkgqprepqvytlppsreemtknqvsltclvkgfypsdiavewesngqpennykttppmldsdgsfflyskltvdksrwqqgnvfscsv
mhealhnhytqkslslspgk Nucleotide sequence of recombinant 5.948.1 light chain = SEQ ID NO: 91

GATATTGTGATGACTCAGTCTCCACTCTCCCTGCCCGTCACCCCTGGAGAGCCGGCCTCCATCTCCT
GT<u>AGGTCTAGTCAGAGCCTCCTGCATAGGAATGGATACAACTACTTGGAT</u>TGGTACCTGCAGAAGCC
AGGGCAGTCTCCACAGCTCCTGATCTAT<u>TTGGGTTCTAATCGGGCCTCC</u>GGGGTCCCTGACAGGTT
CAGTGGCAGTGGATCAGGCACAGATTTTACACTGAAAATCAGCAGAGTGGAGGCTGAGGATGTTGG
GGTTTATTACTGC<u>ATGCAAGCTCTACAAACTCCTCCGGCCACT</u>TTCGGCGGAGGGACCAAGGTGGA
GATCAAAcgaactgtggctgcaccatctgtcttcatcttcccgccatctgatgagcagttgaaatctggaactgcctctgttgtgtgcctgctgaataa
cttctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatcagg
gcctgagctcgcccgtcacaaagagcttcaacaggggagagtgt Derived protein sequence of recombinant 5.948.1 light chain = SEQ ID NO: 92

DIVMTQSPLSLPVTPGEPASISCR<u>SSQSLLHRNGYNYLD</u>WYLQKPGQSPQLLIY<u>LGSNRAS</u>GVPDRFSGS
GSGTDFTLKISRVEAEDVGVYYC<u>MQALQTPPAT</u>FGGGTKVEIKrtvaapsvfifppsdeqlksgtasvvcllnnfypreakv
qwkvdnalqsgnsqesvteqdskdstyslsstltlskadyekhkvyacevthqglsspvtksfnrgec Recombinant 5.948.1 (H100Y)

Nucleotide sequence of recombinant 5.948.1 heavy chain = SEQ ID NO: 121

CAGGTGCAGCTGGTGCAGTCTGGGGCTGAGGTGAAGAAGCCTGGGGCCTCAGTGAAGGTCTCCTG
CAAGGCTTCTGGATACACCTTCACC<u>AGTTATGATATCAACTGGGTGCGACAGGCCACTGGACAAGG
GCTTGAGTGGATGGGA</u><u>TGGATGGACCCTAACAGTGGTAACACAGGCTATGCACAGAAGTTCCAGGG
C</u>AGAGTCACCATGACCAGGAACACCTCCATAAGCACAGCCTACATGGAGCTGAGCAGCCTGAGATC
TGAGGACACGGCCGTGTATTACTGTGCGAGA<u>6666666GGCTACTATGATAGTGATGGTTATTACTCCTTCTCC
GGTATGGACGTC</u>TGGGGCCAAGGGACCACGGTCACCGTCTCCTCAgcctccaccaagggcccatcggtcttcccc
ctggcgccctgctccaggagcacctccgagagcacagcggccctgggctgcctggtcaaggactacttccccgaaccggtgacggtgtcgtgga

```
actcaggcgctctgaccagcggcgtg
cacaccttcccggctgtcctacagtcctcaggactctactccctcagcagcgtagtgaccgtgccctccagcaacttcggcacccagacctacacct
gcaacgtagatcacaagcccagcaacaccaaggtggacaagacagttgagcgcaaatgttgtgtcgagtgcccaccgtgcccagcaccacctgt
ggcaggaccgtcagtcttcctcttcccccaaaacccaaggacaccctcatgatcctccc
ggaccccctgaggtcacgtgcgtggtggtggacgtgagccacgaagaccccgaggtccagttcaactggtacgtggacggcgtggaggtgcataa
tgccaagacaaagccacgggaggagcagttcaacagcacgttccgtgtggtcagcgtcctcaccgtcgtgcaccaggactggctgaacggcaa
ggagtacaagtgcaaggtctccaacaaaggcctcccagccccatcgagaaaaccatctccaaaaccaaagggcagccccgagaaccacag
gtgtacaccctgcccccatcccgggaggagatgaccaagaaccaggtcagcctgacctgcctggtcaaaggcttctaccccagcgacatcgccgt
ggagtgggagagcaatgggcagccggagaacaactacaagaccacacctcccatgctggactccgacggctccttcttcctctacagcaagctc
accgtggacaagagcaggtggcagcaggggaacgtcttctcatgctccgtgatgcatgaggctctgcacaaccactacacagaagagcctct
ccctgtctccgggtaaa
```

Derived protein sequence of recombinant 5.948.1 heavy chain = SEQ ID NO: 122

```
QVQLVQSGAEVKKPGASVKVSCKASGYTFTSYDINWVRQATGQGLEWMGWMDPNSGNTGYAQKFQG
RVTMTRNTSISTAYMELSSLRSEDTAVYYCARGYYDSDGYYSFSGMDVWGQGTTVTVSSastkgpsvfplap
csrstsestaalgclvkdyfpepvtvswnsngaltsgvhtfpavlqssglyslssvvtvpssnfgtqtytcnvdhkpsntkvdktverkccvecppcpap
pvagpsvflfppkpkdtlmisrtpevtcvvvdvshedpevqfnwyvdgvevhnaktkpreeqfnstfrvvsvltvvhqdwlngkeykckvsnkglp
apiektisktkgqprepqvytlppsreemtknqvsltclvkgfypsdiavewesngqpennykttppmldsdgsfflyskltvdksrwqqgnvfscsv
mhealhnhytqkslslspgk
```

Nucleotide sequence of recombinant 5.948.1 light chain = SEQ ID NO: 131

```
GATATTGTGATGACTCAGTCTCCACTCTCCCTGCCCGTCACCCCTGGAGAGCCGGCCTCCATCTCCT
GTAGGTCTAGTCAGAGCCTCCTGCATAGGAATGGATACAACTACTTGGATTGGTACCTGCAGAAGCC
AGGGCAGTCTCCACAGCTCCTGATCTATTTGGGTTCTAATCGGGCCTCCGGGGTCCCTGACAGGTT
CAGTGGCAGTGGATCAGGCACAGATTTTACACTGAAAATCAGCAGAGTGGAGGCTGAGGATGTTGG
GGTTTATTACTGCATGCAAGCTCTACAAACTCCTCCGGCCACTTTCGGCGGAGGGACCAAGGTGGA
GATCAAAcgaactgtggctgcaccatctgtcttcatcttcccgccatctgatgagcagttgaaatctggaactgcctctgttgtgtgcctgctgaataa
cttctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatcagg
gcctgagctcgcccgtcacaaagagcttcaacaggggagagtgt
```

Derived protein sequence of recombinant 5.948.1 light chain = SEQ ID NO: 132

```
DIVMTQSPLSLPVTPGEPASISCRSSQSLLHRNGYNYLDWYLQKPGQSPQLLIYLGSNRASGVPDRFSGS
GSGTDFTLKISRVEAEDVGVYYCMQALQTPPATFGGGTKVEIKrtvaapsvfifppsdeqlksgtasvvcllnnfypreakv
qwkvdnalqsgnsqesvteqdskdstyslsstltlskadyekhkvyacevthqglsspvtksfnrgec
```

Full list of sequences

SEQ ID NO 1: Recombinant 5.396.1 - Full-length Heavy-Chain Nucleotide sequence

```
CAGGTGCAGCTACAGCAGTGGGGCGCAGGACTGTTGAAGCCTTCGGAGACCCTGTCCCTCACCTG
CGCTGTCTATGGTGGGTCCTTCAGTGGTTACTACTGGAGCTGGATCCGCCAGCCCCCAGGGAAGGG
GCTGGAGTGGATTGGGGAAATCCATCATAGTGGAAGCACCAACTACAACCCGTCCCTCAAGAGTCG
AGTCACCATATCAGTAGACACGTCCAAGAACCAGTTCTCCCTGAAGCTGAGCTCTGTGACCGCCGC
GGACACGGCTGTGTATTACTGTGCGAGA77777777GACAACTGGAACGACTCTTTCTACTACTACTACGGTATG
GACGTCTGGGGCCAAGGGACCACGGTCACCGTCTCCTCAgcctccaccaagggcccatcggtcttccccctggcgccc
tgctccaggagcacctccgagagcacagcggccctgggctgcctggtcaaggactacttccccgaaccggtgacggtgtcgtggaactcaggcg
ctctgaccagcggcgtgcacaccttcccggctgtcctacagtcctcaggactctactccctcagcagcgtagtgaccgtgccctccagcaacttcggc
acccagacctacacctgcaacgtagatcacaagcccagcaacaccaaggtggacaagacagttgagcgcaaatgttgtgtcgagtgcccaccgt
gcccagcaccacctgtggcaggaccgtcagtcttcctcttccccccaaaacccaaggacaccctcatgatccccggaccccctgaggtcacgtgcg
tggtggtggacgtgagccacgaagaccccgaggtccagttcaactggtacgtggacggcgtggaggtgcataatgccaagacaaagccacggg
aggagcagttcaacagcacgttccgtgtggtcagcgtcctcaccgtcgtgcaccaggactggctgaacggcaaggagtacaagtgcaaggtctcc
aacaaaggcctcccagcccccatcgagaaaaccatctccaaaaccaaagggcagccccgagaaccacacctcccatgctggactccgacgg
ctccttcttcctctacagcaagctcaccgtggacaagagcaggtggc
agcagggaacgtcttctcatgctccgtgatgcatgaggctctgcacaaccactacacagaagagcctctccctgtctcgggtaaa
```

SEQ ID NO 2: Recombinant 5.396.1 - Full-length Heavy-Chain Predicted amino-acid sequence

```
QVQLQQWGAGLLKPSETLSLTCAVYGGSFSGYYWSWIRQPPGKGLEWIGEIHHSGSTNYNPSLKSRVTI
SVDTSKNQFSLKLSSVTAADTAVYYCARDNWNDSFYYYGMDVWGQGTTVTVSSastkgpsvfplapcsrstse
staalgclvkdyfpepvtvswnsngaltsgvhtfpavlqssglyslssvvtvpssnfgtqtytcnvdhkpsntkvdktverkccvecppcpappvagps
vflfppkpkdtlmisrtpevtcvvvdvshedpevqfnwyvdgvevhnaktkpreeqfnstfrvvsvltvvhqdwlngkeykckvsnkglpapiektis
ktkgqprepqvytlppsreemtknqvsltclvkgfypsdiavewesngqpennykttppmldsdgsfflyskltvdksrwqqgnvfscsvmhealh
nhytqkslslspgk
```

SEQ ID NO 3: Recombinant 5.396.1 - Heavy-Chain Variable-Domain Nucleotide sequence

```
CAGGTGCAGCTACAGCAGTGGGGCGCAGGACTGTTGAAGCCTTCGGAGACCCTGTCCCTCACCTG
CGCTGTCTATGGTGGGTCCTTCAGTGGTTACTACTGGAGCTGGATCCGCCAGCCCCCAGGGAAGGG
GCTGGAGTGGATTGGGGAAATCCATCATAGTGGAAGCACCAACTACAACCCGTCCCTCAAGAGTCG
AGTCACCATATCAGTAGACACGTCCAAGAACCAGTTCTCCCTGAAGCTGAGCTCTGTGACCGCCGC
GGACACGGCTGTGTATTACTGTGCGAGA777777GACAACTGGAACGACTCTTTCTACTACTACTACGGTATG
GACGTCTGGGGCCAAGGGACCACGGTCACCGTCTCCTCA
```

SEQ ID NO 4: Recombinant 5.396.1 - Predicted Heavy-Chain Variable-Domain amino-acid sequence QVQLQQWGAGLLKPSETLSLTCAVYGGSFSGYYWSWIRQPPGKGLEWIGEIHHSGSTNYNPSLKSRVTI
SVDTSKNQFSLKLSSVTAADTAVYYCARDNWNDSFYYYGMDVWGQGTTVTVSS SEQ ID NO 5: Recombinant 5.396.1 - Heavy-Chain CDR1 Nucleotide sequence

GGTTACTACTGGAGC

SEQ ID NO 6: Recombinant 5.396.1 - Predicted Heavy-Chain CDR1 amino-acid sequence

GYYWS

SEQ ID NO 7: Recombinant 5.396.1 - Heavy-Chain CDR2 Nucleotide sequence

GAAATCCATCATAGTGGAAGCACCAACTACAACCCGTCCCTCAAGAGT

SEQ ID NO 8: Recombinant 5.396.1 - Predicted Heavy-Chain CDR2 amino-acid sequence

EIHHSGSTNYNPSLKS

SEQ ID NO 9: Recombinant 5.396.1 - Heavy-Chain CDR3 Nucleotide sequence

GACAACTGGAACGACTCTTTCTACTACTACTACGGTATGGACGTC

SEQ ID NO 10: Recombinant 5.396.1 - Predicted Heavy-Chain CDR3 amino-acid sequence

DNWNDSFYYYYGMDV

SEQ ID NO 11: Recombinant 5.396.1 - Full-length Light-Chain Nucleotide sequence

GACATCCAGATGACCCAGTCTCCATCATCACTGTCTGCATCTGTAGGAGACAGAGTCACCATCACAT
GTCGGGCGAGTCAGGGCATTAGCAATCATTTAGCCTGGTTTCAGCAGAAACCAGGGAAAGCCCCTA
AGTCCCTGATCTATGCTGCATCCAGTTTGCAAAGTGGGGTCCCATCAAAGTTCAGCGGCAGTGGATC
TGGGACAGATTTCACTCTCACCATCAGCAGCCTGCAGCCTGAAGATTTTGCAACTTATTACTGCCAAC
AGTATAATAGGCACCCATTCACTTTCGGCCCTGGGACCAAAGTGGATATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt SEQ ID NO 12: Recombinant 5.396.1 - Predicted Full-length Light-Chain amino-acid sequence DIQMTQSPSSLSASVGDRVTITCRASQGISNHLAWFQQKPGKAPKSLIYAASSLQSGVPSKFSGSGSGTD
FTLTISSLQPEDFATYYCQQYNRHPFTFGPGTKVDIKrtvaapsvfifppsdeqlksgtasvvcllnnfypreakvqwkvdnalq
sgnsqesvteqdskdstyslssttltlskadyekhkvyacevthqglsspvtksfnrgec SEQ ID NO 13: Recombinant 5.396.1 - Light-Chain Variable-Domain Nucleotide sequence GACATCCAGATGACCCAGTCTCCATCATCACTGTCTGCATCTGTAGGAGACAGAGTCACCATCACAT
GTCGGGCGAGTCAGGGCATTAGCAATCATTTAGCCTGGTTTCAGCAGAAACCAGGGAAAGCCCCTA
AGTCCCTGATCTATGCTGCATCCAGTTTGCAAAGTGGGGTCCCATCAAAGTTCAGCGGCAGTGGATC
TGGGACAGATTTCACTCTCACCATCAGCAGCCTGCAGCCTGAAGATTTTGCAACTTATTACTGCCAAC
AGTATAATAGGCACCCATTCACTTTCGGCCCTGGGACCAAAGTGGATATCAAA SEQ ID NO 14: Recombinant 5.396.1 - Predicted Light-Chain Variable-Domain amino-acid sequence DIQMTQSPSSLSASVGDRVTITCRASQGISNHLAWFQQKPGKAPKSLIYAASSLQSGVPSKFSGSGSGTD
FTLTISSLQPEDFATYYCQQYNRHPFTFGPGTKVDIK SEQ ID NO 15: Recombinant 5.396.1 - Light-Chain CDR1 Nucleotide sequence

CGGGCGAGTCAGGGCATTAGCAATCATTTAGCC

SEQ ID NO 16: Recombinant 5.396.1 - Predicted Light-Chain CDR1 amino-acid sequence

RASQGISNHLA

SEQ ID NO 17: Recombinant 5.396.1 - Light-Chain CDR2 Nucleotide sequence

GCTGCATCCAGTTTGCAAAGT

SEQ ID NO 18: Recombinant 5.396.1 - Predicted Light-Chain CDR2 amino-acid sequence

AASSLQS

SEQ ID NO 19: Recombinant 5.396.1 - Light-Chain CDR3 Nucleotide sequence

CAACAGTATAATAGGCACCCATTCACT

SEQ ID NO 20: Recombinant 5.396.1 - Predicted Light-Chain CDR3 amino-acid sequence

QQYNRHPFT

SEQ ID NO 21: Recombinant 5.396.1 (Hc-S103N Lc-K61R) - Full-length Heavy-Chain Nucleotide sequence CAGGTGCAGCTACAGCAGTGGGGCGCAGGACTGTTGAAGCCTTCGGAGACCCTGTCCCTCACCTG
CGCTGTCTATGGTGGGTCCTTCAGTGGTTACTACTGGAGCTGGATCCGCCAGCCCCCAGGGAAGGG
GCTGGAGTGGATTGGGGAAATCCATCATAGTGGAAGCACCAACTACAACCCGTCCCTCAAGAGTCG
AGTCACCATATCAGTAGACACGTCCAAGAACCAGTTCTCCCTGAAGCTGAGCTCTGTGACCGCCGC
GGACACGGCTGTGTATTACTGTGCGAGA7777777GACAACTGGAACGACAACTTCTACTACTACGGTATG
GACGTCTGGGGCCAAGGGACCACGGTCACCGTCTCCTCAgcctccaccaagggcccatcggtcttcccccctggcgccc
tgctccaggagcacctccgagagcacagcggccctgggctgcctggtcaaggactacttccccgaaccggtgacggtgtcgtggaactcaggcg
ctctgaccagcggcgtgcacaccttcccggctgtcctacagtcctcaggactctactccctcagcagcgtagtgaccgtgccctccagcaacttcggc
acccagacctacacctgcaacgtagatcacaagcccagcaacaccaaggtggacaagacagttgagcgcaaatgttgtgtcgagtgcccaccgt
gcccagcaccacctgtggcaggaccgtcagtcttcctcttccccccaaaacccaaggacaccctcatgatctcccggacccctgaggtcacgtgcg
tggtggtggacgtgagccacgaagaccccgaggtccagttcaactggtacgtggacggcgtggaggtgcataatgccaagacaaagccacggg
aggagcagttcaacagcacgttccgtgtggtcagcgtcctcaccgtcgtgcaccaggactggctgaacggcaaggagtacaagtgcaaggtctcc
aacaaaggcctcccagcccccatcgagaaaaccatctccaaaaccaaagggcagccccgagaaccacaggtgtacaccctgcccccatcccg
ggaggagatgaccaagaaccaggtcagcctgacctgcctggtcaaaggcttctaccccagcgacatcgccgtggagtgggagagcaatgggca
gccggagaacaactacaagaccacacctcccatgctggactccgacggctccttcttcctctacagcaagctcaccgtggacaagagcaggtggc
agcaggggaacgtcttctcatgctccgtgatgcatgaggctctgcacaaccactacacacagaagagcctctccctgtctccgggtaaa SEQ ID NO 22: Recombinant 5.396.1 (Hc-S103N Lc-K61R) - Predicted Full-length Heavy-Chain amino-acid sequence QVQLQQWGAGLLKPSETLSLTCAVYGGSFSGYYWSWIRQPPGKGLEWIGEIHHSGSTNYNPSLKSRVTI
SVDTSKNQFSLKLSSVTAADTAVYYCARDNWNDNFYYYYGMDVWGQGTTVTVSSastkgpsvflplapcsrstse
staalgclvkdyfpepvtvswnsgaltsgvhtfpavlqssglyslssvvtvpssnfgtqtytcnvdhkpsntkvdktverkccvecppcpappvagps
vflfppkpkdtlmisrtpevtcvvvdvshedpevqfnwyvdgvevhnaktkpreeqfnstfrvvsvltvvhqdwlngkeykckvsnkglpapiektis
ktkgqprepqvytlppsreemtknqvsltclvkgfypsdiavewesngqpennykttppmldsdgsfflyskltvdksrwqqgnvfscsvmhealh
nhytqkslslspgk SEQ ID NO 23: Recombinant 5.396.1 (Hc-S103N Lc-K61R) - Heavy-Chain Variable-Domain Nucleotide sequence CAGGTGCAGCTACAGCAGTGGGGCGCAGGACTGTTGAAGCCTTCGGAGACCCTGTCCCTCACCTG
CGCTGTCTATGGTGGGTCCTTCAGTGGTTACTACTGGAGCTGGATCCGCCAGCCCCCAGGGAAGGG
GCTGGAGTGGATTGGGGAAATCCATCATAGTGGAAGCACCAACTACAACCCGTCCCTCAAGAGTCG
AGTCACCATATCAGTAGACACGTCCAAGAACCAGTTCTCCCTGAAGCTGAGCTCTGTGACCGCCGC
GGACACGGCTGTGTATTACTGTGCGAGA7777777GACAACTGGAACGACAACTTCTACTACTACGGTATG
GACGTCTGGGGCCAAGGGACCACGGTCACCGTCTCCTCA SEQ ID NO 24: Recombinant 5.396.1 (Hc-S103N Lc-K61R) - Predicted Heavy-Chain Variable-Domain amino-acid sequence QVQLQQWGAGLLKPSETLSLTCAVYGGSFSGYYWSWIRQPPGKGLEWIGEIHHSGSTNYNPSLKSRVTI
SVDTSKNQFSLKLSSVTAADTAVYYCARDNWNDNFYYYYGMDVWGQGTTVTVSS SEQ ID NO 25: Recombinant 5.396.1 (Hc-S103N Lc-K61R) - Heavy-Chain CDR1 Nucleotide sequence

GGTTACTACTGGAGC

SEQ ID NO 26: Recombinant 5.396.1 (Hc-S103N Lc-K61R) - Predicted Heavy-Chain CDR1 amino-acid sequence

GYYWS

SEQ ID NO 27: Recombinant 5.396.1 (Hc-S103N Lc-K61R) - Heavy-Chain CDR2 Nucleotide sequence

GAAATCCATCATAGTGGAAGCACCAACTACAACCCGTCCCTCAAGAGT

SEQ ID NO 28: Recombinant 5.396.1 (Hc-S103N Lc-K61R) - Predicted Heavy-Chain CDR2 amino-acid sequence

EIHHSGSTNYNPSLKS

SEQ ID NO 29: Recombinant 5.396.1 (Hc-S103N Lc-K61R) - Heavy-Chain CDR3 Nucleotide sequence

GACAACTGGAACGACAACTTCTACTACTACTACGGTATGGACGTC

SEQ ID NO 30: Recombinant 5.396.1 (Hc-S103N Lc-K61R) - Predicted Heavy-Chain CDR3 amino-acid sequence

DNWNDNFYYYGMDV

SEQ ID NO 31: Recombinant 5.396.1 (Hc-S103N Lc-K61R) - Full-length Light-Chain Nucleotide sequence GACATCCAGATGACCCAGTCTCCATCATCACTGTCTGCATCTGTAGGAGACAGAGTCACCATCACAT
GT<u>CGGGCGAGTCAGGGCATTAGCAATCATTTAGCC</u>TGGTTTCAGCAGAAACCAGGGAAAGCCCCTA
AGTCCCTGATCTAT<u>GCTGCATCCAGTTTGCAAAGT</u>GGGGTCCCATCAAGGTTCAGCGGCAGTGGATC
TGGGACAGATTTCACTCTCACCATCAGCAGCCTGCAGCCTGAAGATTTTGCAACTTATTACTGC<u>CAAC
AGTATAATAGGCACCCATTCACT</u>TTCGGCCCTGGGACCAAAGTGGATATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt SEQ ID NO 32: Recombinant 5.396.1 (Hc-S103N Lc-K61R) - Predicted Full-length Light-Chain amino-acid sequence DIQMTQSPSSLSASVGDRVTITC<u>RASQGISNHLA</u>WFQQKPGKAPKSLIY<u>AASSLQS</u>GVPSRFSGSGSGTD
FTLTISSLQPEDFATYYC<u>QQYNRHPFT</u>FGPGTKVDIKrtvaapsvfifppsdeqlksgtasvvcllnnfypreakvqwkvdnalq
sgnsqesvteqdskdstyslsstltlskadyekhkvyacevthqglsspvtksfnrgec SEQ ID NO 33: Recombinant 5.396.1 (Hc-S103N Lc-K61R) - Light-Chain Variable-Domain Nucleotide sequence GACATCCAGATGACCCAGTCTCCATCATCACTGTCTGCATCTGTAGGAGACAGAGTCACCATCACAT
GT<u>CGGGCGAGTCAGGGCATTAGCAATCATTTAGCC</u>TGGTTTCAGCAGAAACCAGGGAAAGCCCCTA
AGTCCCTGATCTAT<u>GCTGCATCCAGTTTGCAAAGT</u>GGGGTCCCATCAAGGTTCAGCGGCAGTGGATC
TGGGACAGATTTCACTCTCACCATCAGCAGCCTGCAGCCTGAAGATTTTGCAACTTATTACTGC<u>CAAC
AGTATAATAGGCACCCATTCACTTTCGGCCCTGGGACCAAAGTGGATATCAAA</u>

SEQ ID NO 34: Recombinant 5.396.1 (Hc-S103N Lc-K61R) - Predicted Light-Chain Variable-Domain amino-acid sequence DIQMTQSPSSLSASVGDRVTITC<u>RASQGISNHLA</u>WFQQKPGKAPKSLIY<u>AASSLQS</u>GVPSRFSGSGSGTD
FTLTISSLQPEDFATYYC<u>QQYNRHPFT</u>FGPGTKVDIK SEQ ID NO 35: Recombinant 5.396.1 (Hc-S103N Lc-K61R) - Light-Chain CDR1 Nucleotide sequence <u>CGGGCGAGTCAGGGCATTAGCAATCATTTAGCC</u>

SEQ ID NO 36: Recombinant 5.396.1 (Hc-S103N Lc-K61R) - Predicted Light-Chain CDR1 amino-acid sequence <u>RASQGISNHLA</u>

SEQ ID NO 37: Recombinant 5.396.1 (Hc-S103N Lc-K61R) - Light-Chain CDR2 Nucleotide sequence <u>GCTGCATCCAGTTTGCAAAGT</u>

SEQ ID NO 38: Recombinant 5.396.1 (Hc-S103N Lc-K61R) - Predicted Light-Chain CDR2 amino-acid sequence <u>AASSLQS</u>

SEQ ID NO 39: Recombinant 5.396.1 (Hc-S103N Lc-K61R) - Light-Chain CDR3 Nucleotide sequence <u>CAACAGTATAATAGGCACCCATTCACT</u>

SEQ ID NO 40: Recombinant 5.396.1 (Hc-S103N Lc-K61R) - Predicted Light-Chain CDR3 amino-acid sequence <u>QQYNRHPFT</u>

SEQ ID NO 41: Recombinant 6.605.1 - Full-length Heavy-Chain Nucleotide sequence

CAGGTTCACCTGGTGCAGTCTGGAGCTGAGGTGAAGATGCCTGGGGCCTCAGTGAAGGTCTCCTGC
AAGGCTTCTGGTTACACCTTTACC<u>AGCTATGGTATCAGC</u>TGGGTGCGACAGGCCCCTGGACAAGGG
CTTGAGTGGATGGGA<u>TGGATCAGCGCTTACAATGGTAACACAAACTATGCACAGAAGCTCCAGGGC</u>
AGAATCACCATGACCACAGACACATCCACGAGCACAGCCTACATGGACCTGAGGAGCCTGAGATCT
GACGACACGGCCGTGTATTACTGTGCGAGA<u>GATGGGGATTACTATGATCCTTTTGACTAC</u>TGGGGCC

-continued

```
AGGGAACCCTGGTCACCGTCTCCTCAgcctccaccaagggcccatcggtcttccccctggcgccctgctccaggagcacctccg
agagcacagcggccctgggctgcctggtcaaggactactt ccccgaaccggtgacggtgtcgtggaactcaggcgctctgaccagcggcgtgca
ccttcccggctgtcctacagtcctcaggactctactccctcagcagcgtagtgaccgtgccctccagcaacttcggcacccagacctacacctgc
aacgtagatcacaagcccagcaacaccaaggtggacaagacagttgagcgcaaagttgttgagcgcaaagttgttgagctgcaaatgttgtcgagtgccaccgtgccagcaccacctgt
gcaggaccgtcagtcttcctcttccccccaaaacccaaggacaccctcatgatctcccggacccctgaggtcacgtgcgtggtggtggacgtgagc
cacgaagaccccgaggtccagttcaactggtacgtggacggcgtggaggtgcataatgccaagacaaagccacgggaggagcagttcaacag
cacgttccgtgtggtcagcgtcctcaccgtcgtgcaccaggactggctgaacggcaaggagtacaagtgcaaggtctccaacaaaggcctcccag
ccccatcgagaaaaccatctccaaaaccaaagggcagccccgagaaccacaggtgtacaccctgcccccatcccgggaggagatgaccaa
gaaccaggtcagcctgacctgcctggtcaaaggcttctaccccagcgacatcgccgtggagtgggagagcaatgggcagccggagaacaacta
caagaccacacctcccatgctggactccgacggctccttcttcctctacagcaagctcaccgtggacaagagcaggtggcagcaggggaacgtct
tctcatgctccgtgatgcatgaggctctgcacaaccactacacacagaagagcctctccctgtctccgggtaaa
```

SEQ ID NO 42: Recombinant 6.605.1 - Predicted Full-length Heavy-Chain amino-acid sequence

```
QVHLVQSGAEVKMPGASVKVSCKASGYTFTSYGISWVRQAPGQGLEWMGWISAYNGNTNYAQKLQGR
ITMTTDTSTSTAYMDLRSLRSDDTAVYYCARDGDYYDPFDYWGQGTLVTVSSastkgpsvfplapcsrstsestaal
gclvkdyfpepvtvswnsgaltsgvhtfpavlqssglyslssvvtvpssnfgtqtytcnvdhkpsntkvdktverkccvecppcpappvagpsvflfp
pkpkdtlmisrtpevtcvvvdvshedpevqfnwyvdgvevhnaktkpreeqfnstfrvvsvltvvhqdwlngkeykckvsnkglpapiektisktkg
qprepqvytlppsreemtknqvsltclvkgfypsdiavewesngqpennykttppmldsdgsfflyskltvdksrwqqgnvfscsvmhealhnhyt
qkslslspgk
```

SEQ ID NO 43: Recombinant 6.605.1 - Heavy-Chain Variable-Domain Nucleotide sequence

```
CAGGTTCACCTGGTGCAGTCTGGAGCTGAGGTGAAGATGCCTGGGGCCTCAGTGAAGGTCTCCTGC
AAGGCTTCTGGTTACACCTTTACCAGCTATGGTATCAGCTGGGTGCGACAGGCCCCTGGACAAGGG
CTTGAGTGGATGGGATGGATCAGCGCTTACAATGGTAACACAAACTATGCACAGAAGCTCCAGGGC
AGAATCACCATGACCACAGACACATCCACGAGCACAGCCTACATGGACCTGAGGAGCCTGAGATCT
GACGACACGGCCGTGTATTACTGTGCGAGAGATGGGGATTACTATGATCCTTTTGACTACTGGGGCC
AGGGAACCCTGGTCACCGTCTCCTCA
```

SEQ ID NO 44: Recombinant 6.605.1 - Predicted Heavy-Chain Variable-Domain
amino-acid sequence

```
QVHLVQSGAEVKMPGASVKVSCKASGYTFTSYGISWVRQAPGQGLEWMGWISAYNGNTNYAQKLQGR
ITMTTDTSTSTAYMDLRSLRSDDTAVYYCARDGDYYDPFDYWGQGTLVTVSS
```

SEQ ID NO 45: Recombinant 6.605.1 - Heavy-Chain CDR1 Nucleotide sequence

AGCTATGGTATCAGC

SEQ ID NO 46: Recombinant 6.605.1 - Predicted Heavy-Chain CDR1 amino-acid sequence

SYGIS

SEQ ID NO 47: Recombinant 6.605.1 - Heavy-Chain CDR2 Nucleotide sequence

TGGATCAGCGCTTACAATGGTAACACAAACTATGCACAGAAGCTCCAGGGC

SEQ ID NO 48: Recombinant 6.605.1 - Predicted Heavy-Chain CDR2 amino-acid sequence

WISAYNGNTNYAQKLQG

SEQ ID NO 49: Recombinant 6.605.1 - Heavy-Chain CDR3 Nucleotide sequence

GATGGGGATTACTATGATCCTTTTGACTAC

SEQ ID NO 50: Recombinant 6.605.1 - Predicted Heavy-Chain CDR3 amino-acid sequence

DGDYYDPFDY

SEQ ID NO 51: Recombinant 6.605.1 - Full-length Light-Chain Nucleotide sequence

```
GACATCCAGATGACCCAGTCTCCATCCTCCCTGTCTGCATCTGTAGGAGACAGAGTCACCATCACTT
GCCGGACAAGTCAGAGTATTAGCAACTGGTTAAATTGGTATCAGCAGAAACCAGGGAAAGCCCCTAA
ACTCCTGATCTATGGTGCCTCCACTTTGAAAAGTGGGGTCCCATCAAGGTTCAGTGGCAGTGAATCT
GGGACAGATTTCACTCTCACCATCAGCAGTCTGCAACCTGAAGATTTTGCACTTACTACTGTCAACA
GAGTTACAGTACCCCTCCGACGTTCGGCCAAGGGACCAAGGTGGAAATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt
```

SEQ ID NO 52: Recombinant 6.605.1 - Predicted Full-length Light-Chain amino-acid sequence

```
DIQMTQSPSSLSASVGDRVTITCRTSQSISNWLNWYQQKPGKAPKLLIYGASTLKSGVPSRFSGSESGTD
FTLTISSLQPEDFATYYCQQSYSTPPTFGQGTKVEIKrtvaapsvfifppsdeqlksgtasvvcllnnfypreakvqwkvdnalq
sgnsqesvteqdskdstyslsstltlskadyekhkvyacevthqglsspvtksfnrgec
```

SEQ ID NO 53: Recombinant 6.605.1 - Light-Chain Variable-Domain Nucleotide sequence GACATCCAGATGACCCAGTCTCCATCCTCCCTGTCTGCATCTGTAGGAGACAGAGTCACCATCACTT
GC<u>CGGACAAGTCAGAGTATTAGCAACTGGTTAAAT</u>TGGTATCAGCAGAAACCAGGGAAAGCCCCTAA
ACTCCTGATCTATG<u>GTGCCTCCACTTTGAAAAGT</u>GGGGTCCCATCAAGGTTCAGTGGCAGTGAATCT
GGGACAGATTTCACTCTCACCATCAGCAGTCTGCAACCTGAAGATTTTGCAACTTACTACTGT<u>CAACA
GAGTTACAGTACCCCTCCGACG</u>TTCGGCCAAGGGACCAAGGTGGAAATCAAA SEQ ID NO 54: Recombinant 6.605.1 - Predicted Light-Chain Variable-Domain amino-acid sequence DIQMTQSPSSLSASVGDRVTITC<u>RTSQSISNWLN</u>WYQQKPGKAPKLLIY<u>GASTLKS</u>GVPSRFSGSESGTD
FTLTISSLQPEDFATYYC<u>QQSYSTPPT</u>FGQGTKVEIK SEQ ID NO 55: Recombinant 6.605.1 - Light-Chain CDR1 Nucleotide sequence <u>CGGACAAGTCAGAGTATTAGCAACTGGTTAAAT</u>

SEQ ID NO 56: Recombinant 6.605.1 - Predicted Light-Chain CDR1 amino-acid sequence <u>RTSQSISNWLN</u>

SEQ ID NO 57: Recombinant 6.605.1 - Light-Chain CDR2 Nucleotide sequence

<u>GGTGCCTCCACTTTGAAAAGT</u>

SEQ ID NO 58: Recombinant 6.605.1 - Predicted Light-Chain CDR2 amino-acid sequence <u>GASTLKS</u>

SEQ ID NO 59: Recombinant 6.605.1 - Light-Chain CDR3 Nucleotide sequence

<u>CAACAGAGTTACAGTACCCCTCCGACG</u>

SEQ ID NO 60: Recombinant 6.605.1 - Predicted Light-Chain CDR3 amino-acid sequence <u>QQSYSTPPT</u>

SEQ ID NO 61: Recombinant 6.605.1 (Hc-H3Q, M13K, D82E; Lc-T25A, T53S) - Full-length Heavy-Chain Nucleotide sequence CAGGTCCAGCTGGTGCAGTCTGGAGCTGAGGTGAAGAAGCCTGGGGCCTCAGTGAAGGTCTCCTG
CAAGGCTTCTGGTTACACCTTTACC<u>AGCTATGGTATCAGC</u>TGGGTGCGACAGGCCCCTGGACAAGG
GCTTGAGTGGATGGGAT<u>GGATCAGCGCTTACAATGGTAACACAAACTATGCACAGAAGCTCCAGGG
C</u>AGAATCACCATGACCACAGACACATCCACGAGCACAGCCTACATGGAACTGAGGAGCCTGAGATC
TGACGACACGGCCGTGTATTACTGTGCGAGA<u>GATGGGGATTACTATGATCCTTTTGACTAC</u>TGGGGC
CAGGGAACCCTGGTCACCGTCTCCTCAgcctccaccaagggcccatcggtcttccccctggcgccctgctccaggagcacctcc
gagagcacagcggccctgggctgcctggtcaaggactacttccccgaaccggtgacggtgtcgtggaactcaggcgctctgaccagcggcgtgc
acaccttcccggctgtcctacagtcctcaggactctactccctcagcagcgtagtgaccgtgccctccagcaacttcggcacccagacctacacctg
caacgtagatcacaagcccagcaacaccaaggtggacaagacagttgagcgcaaatgttgtgtcgagtgcccaccgtgcccagcaccacctgtg
gcaggaccgtcagtcttcctcttccccccaaaacccaaggacaccctcatgatctcccggacccctgaggtcacgtgcgtggtggtggacgtgagc
cacgaagaccccgaggtccagttcaactggtacgtggacggcgtggaggtgcataatgccaagacaaagccacgggaggagcagttcaacag
cacgttccgtgtggtcagcgtcctcaccgtcgtgcaccaggactggctgaacggcaaggagtacaagtgcaaggtctccaacaaaggcctcccag
ccccatcgagaaaaccatctccaaaaccaaagggcagccccgagaaccacaggtgtacaccctgcccccatcccgggaggagatgaccaa
gaaccaggtcagcctgacctgcctggtcaaaggcttctaccccagcgacatcgccgtggagtgggagagcaatgggcagccggagaacaacta
caagaccacacctcccatgctggactccgacggctccttcttcctctacagcaagctcaccgtggacaagagcaggtggcagcaggggaacgtct
tctcatgctccgtgatgcatgaggctctgcacaaccactacacacagaagagcctctccctgtctccgggtaaa SEQ ID NO 62: Recombinant 6.605.1 (Hc-H3Q, M13K, D82E; Lc-T25A, T53S) - Predicted Full-length Heavy-Chain amino-acid sequence QV<b>Q</b>LVQSGAEV<b>K</b>KPGASVKVSCKASGYTFT<u>SYGIS</u>WVRQAPGQGLEWMG<u>WISAYNGNTNYAQKLQGR
ITMTTDTSTSTAYM</u><b>E</b>LRSLRSDDTAVYYCAR<u>DGDYYDPFDY</u>WGQGTLVTVSSastkgpsvfplapcsrstsestaal
gclvkdyfpepvtvswnsgaltsgvhtfpavlqssglyslssvvtvpssnfgtqtytcnvdhkpsntkvdktverkccvecppcpappvagpsvflfp
pkpkdtlmisrtpevtcvvvdvshedpevqfnwyvdgvevhnaktkpreeqfnstfrvvsvltvvhqdwIngkeykckvsnkglpapiektisktkg
qprepqvytlppsreemtknqvsltclvkgfypsdiavewesngqpennykttppmldsdgsfflyskltvdksrwqqgnvfscsvmhealhnhyt
qkslslspgk SEQ ID NO 63: Recombinant 6.605.1 (Hc-H3Q, M13K, D82E; Lc-T25A, T53S) - Heavy-Chain Variable-Domain Nucleotide sequence CAGGTCCAGCTGGTGCAGTCTGGAGCTGAGGTGAAGAAGCCTGGGGCCTCAGTGAAGGTCTCCTG
CAAGGCTTCTGGTTACACCTTTACC<u>AGCTATGGTATCAGC</u>TGGGTGCGACAGGCCCCTGGACAAGG
GCTTGAGTGGATGGGAT<u>GGATCAGCGCTTACAATGGTAACACAAACTATGCACAGAAGCTCCAGGG
C</u>AGAATCACCATGACCACAGACACATCCACGAGCACAGCCTACATGGAACTGAGGAGCCTGAGATC
TGACGACACGGCCGTGTATTACTGTGCGAGA<u>GATGGGGATTACTATGATCCTTTTGACTAC</u>TGGGGC
CAGGGAACCCTGGTCACCGTCTCCTCA SEQ ID NO 64: Recombinant 6.605.1 (Hc-H3Q, M13K, D82E; Lc-T25A, T53S) - Predicted
Heavy-Chain Variable-Domain amino-acid sequence QVQLVQSGAEVKKPGASVKVSCKASGYTFT<u>SYGIS</u>WVRQAPGQGLEWMG<u>WISAYNGNTNYAQKLQ</u>GR
ITMTTDTSTSTAYMELRSLRSDDTAVYYCAR<u>DGDYYDPFDY</u>WGQGTLVTSS SEQ ID NO 65: Recombinant 6.605.1 (Hc-H3Q, M13K, D82E; Lc-T25A, T53S) - Heavy-Chain
CDR1 Nucleotide sequence <u>AGCTATGGTATCAGC</u>

SEQ ID NO 66: Recombinant 6.605.1 (Hc-H3Q, M13K, D82E; Lc-T25A, T53S) - Predicted
Heavy-Chain CDR1 amino-acid sequence <u>SYGIS</u>

SEQ ID NO 67: Recombinant 6.605.1 (Hc-H3Q, M13K, D82E; Lc-T25A, T53S) - Heavy-Chain
CDR2 Nucleotide sequence <u>TGGATCAGCGCTTACAATGGTAACACAAACTATGCACAGAAGCTCCAGGGC</u>

SEQ ID NO 68: Recombinant 6.605.1 (Hc-H3Q, M13K, D82E; Lc-T25A, T53S) - Predicted
Heavy-Chain CDR2 amino-acid sequence <u>WISAYNGNTNYAQKLQG</u>

SEQ ID NO 69: Recombinant 6.605.1 (Hc-H3Q, M13K, D82E; Lc-T25A, T53S) - Heavy-Chain
CDR3 Nucleotide sequence <u>GATGGGGATTACTATGATCCTTTTGACTAC</u>

SEQ ID NO 70: Recombinant 6.605.1 (Hc-H3Q, M13K, D82E; Lc-T25A, T53S) - Predicted
Heavy-Chain CDR3 amino-acid sequence <u>DGDYYDPFDY</u>

SEQ ID NO 71: Recombinant 6.605.1 (Hc-H3Q, M13K, D82E; Lc-T25A, T53S) - Full-length
Light-Chain Nucleotide sequence GACATCCAGATGACCCAGTCTCCATCCTCCCTGTCTGCATCTGTAGGAGACAGAGTCACCATCACTT
GCC<u>GGGCAAGTCAGAGTATTAGCAACTGGTTAAAT</u>TGGTATCAGCAGAAACCAGGGAAAGCCCCTAA
ACTCCTGATCTATGGTGCCTCCAGTTTGAAAAGTGGGGTCCCATCAAGGTTCAGTGGCAGTGAATCT
GGGACAGATTTCACTCTCACCATCAGCAGTCTGCAACCTGAAGATTTTGCAACTTACTACTGT<u>CAACA
GAGTTACAGTACCCCTCCGACGTTCGGCCAAGGGACCAAGGTGGAAATCAAA</u>cgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgcctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt SEQ ID NO 72: Recombinant 6.605.1 (Hc-H3Q, M13K, D82E; Lc-T25A, T53S) - Predicted Full-length
Light-Chain amino-acid sequence DIQMTQSPSSLSASVGDRVTITC<u>RASQSISNWLN</u>WYQQKPGKAPKLLIY<u>GASSLKS</u>GVPSRFSGSESGT
DFTLTISSLQPEDFATYYC<u>QQSYSTPPT</u>FGQGTKVEIKrtvaapsvfifppsdeqlksgtasvvcllnnfypreakvqwkvdnal
qsgnsqesvteqdskdstyslsstltlskadyekhkvyacevthqglsspvtksfnrgec SEQ ID NO 73: Recombinant 6.605.1 (Hc-H3Q, M13K, D82E; Lc-T25A, T53S) - Light-Chain
Variable-Domain Nucleotide sequence GACATCCAGATGACCCAGTCTCCATCCTCCCTGTCTGCATCTGTAGGAGACAGAGTCACCATCACTT
GCC<u>GGGCAAGTCAGAGTATTAGCAACTGGTTAAAT</u>TGGTATCAGCAGAAACCAGGGAAAGCCCCTAA
ACTCCTGATCTATGGTGCCTCCAGTTTGAAAAGTGGGGTCCCATCAAGGTTCAGTGGCAGTGAATCT
GGGACAGATTTCACTCTCACCATCAGCAGTCTGCAACCTGAAGATTTTGCAACTTACTACTGT<u>CAACA
GAGTTACAGTACCCCTCCGACGTTCGGCCAAGGGACCAAGGTGGAAATCAAA</u>

SEQ ID NO 74: Recombinant 6.605.1 (Hc-H3Q,M13K,D82E; Lc-T25A,T53S) - Predicted Light-Chain
Variable-Domain amino-acid sequence DIQMTQSPSSLSASVGDRVTITC<u>RASQSISNWLN</u>WYQQKPGKAPKLLIY<u>GASSLKS</u>GVPSRFSGSESGT
DFTLTISSLQPEDFATYYC<u>QQSYSTPPT</u>FGQGTKVEIK SEQ ID NO 75: Recombinant 6.605.1 (Hc-H3Q, M13K, D82E; Lc-T25A, T53S) - Light-
Chain CDR1 Nucleotide sequence <u>CGGGCAAGTCAGAGTATTAGCAACTGGTTAAAT</u>
SEQ ID NO 76: Recombinant 6.605.1 (Hc-H3Q, M13K, D82E; Lc-T25A, T53S) - Predicted
Light-Chain CDR1 amino-acid sequence <u>RASQSISNWLN</u>

SEQ ID NO 77: Recombinant 6.605.1 (Hc-H3Q, M13K, D82E; Lc-T25A, T53S) - Light-Chain CDR2
Nucleotide sequence

GGTGCCTCCAGTTTGAAAAGT

SEQ ID NO 78: Recombinant 6.605.1 (Hc-H3Q, M13K, D82E; Lc-T25A, T53S) - Predicted
Light-Chain CDR2 amino-acid sequence

GASSLKS

SEQ ID NO 79: Recombinant 6.605.1 (Hc-H3Q, M13K, D82E; Lc-T25A, T53S) - Light-Chain
CDR3 Nucleotide sequence

CAACAGAGTTACAGTACCCCTCCGACG

SEQ ID NO 80: Recombinant 6.605.1 (Hc-H3Q, M13K, D82E; Lc-T25A, T53S) - Predicted
Light-Chain CDR3 amino-acid sequence

QQSYSTPPT

SEQ ID NO 81: Recombinant 5.948.1 - Full-length Heavy-Chain Nucleotide sequence

CAGGTGCAGCTGGTGCAGTCTGGGGCTGAGGTGAAGAAGCCTGGGGCCTCAGTGAAGGTCTCCTG
CAAGGCTTCTGGATACACCTTCACCAGTTATGATATCAACTGGGTGCGACAGGCCACTGGACAAGG
GCTTGAGTGGATGGGATGGATGGACCCTAACAGTGGTAACACAGGCTATGCACAGAAGTTCCAGGG
CAGAGTCACCATGACCAGGAACACCTCCATAAGCACAGCCTACATGGAGCTGAGCAGCCTGAGATC
TGAGGACACGGCCGTGTATTACTGTGCGAGAGGCCACTATGATAGTGATGGTTATTACTCCTTCTCC
GGTATGGACGTCTGGGGCCAAGGGACCACGGTCACCGTCTCCTCAgcctccaccaagggcccatcggtcttcccc
ctggcgccctgctccaggagcacctccgagagcacagcggccctgggctgcctggtcaaggactacttccccgaaccggtgacggtgtcgtgga
actcaggcgctctgaccagcggcgtgcacaccttcccggctgtcctacagtcctcaggactctactccctcagcagcgtagtgaccgtgccctccag
caacttcggcacccagacctacacctgcaacgtagatcacaagcccagcaacaccaaggtggacaagacagttgagcgcaaatgttgtgtcga
gtgcccaccgtgcccagcaccacctgtggcaggaccgtcagtcttcctcttccccccaaaacccaaggacaccctcatgatctcccggacccctga
ggtcacgtgcgtggtggtggacgtgagccacgaagaccccgaggtccagttcaactggtacgtggacggcgtggaggtgcataatgccaagaca
aagccacgggaggagcagttcaacagcacgttccgtgtggtcagcgtcctcaccgtcgtgcaccaggactggctgaacggcaaggagtacaagt
gcaaggtctccaacaaaggcctcccagccccatcgagaaaaccatctccaaaaccaaagggcagccccgagaaccacaggtgtacaccctg
cccccatcccgggaggagatgaccaagaaccaggtcagcctgacctgcctggtcaaaggcttctaccccagcgacatcgccgtggagtgggag
agcaatgggcagccggagaacaactacaagaccacacctcccatgctggactccgacggctccttcttcctctacagcaagctcaccgtggacaa
gagcaggtggcagcaggggaacgtcttctcatgctccgtgatgcatgaggctctgcacaaccactacacacagaagagcctctccctgtctccggg
taaa SEQ ID NO 82: Recombinant 5.948.1 - Predicted Full-length Heavy-Chain amino-acid sequence QVQLVQSGAEVKKPGASVKVSCKASGYTFTSYDINWVRQATGQGLEWMGWMDPNSGNTGYAQKFQG
RVTMTRNTSISTAYMELSSLRSEDTAVYYCARGHYDSDGYYSFSGMDVWGQGTTVTVSSAstkgpsvfplap
csrstsestaalgclvkdyfpepvtvswnsgaltsgvhtfpavlqssglyslssvvtvpssnfgtqtytcnvdhkpsntkvdktverkccvecppcpap
pvagpsvflfppkpkdtlmisrtpevtcvvvdvshedpevqfnwyvdgvevhnaktkpreeqfnstfrvvsvltvvhqdwlngkeykckvsnkglp
apiektisktkgqprepqvytlppsreemtknqvsltclvkgfypsdiavewesngqpennykttppmldsdgsfflysklvdksrwqqgnvfscsv
mhealhnhytqkslslspgk SEQ ID NO 83: Recombinant 5.948.1 - Heavy-Chain Variable-Domain Nucleotide sequence CAGGTGCAGCTGGTGCAGTCTGGGGCTGAGGTGAAGAAGCCTGGGGCCTCAGTGAAGGTCTCCTG
CAAGGCTTCTGGATACACCTTCACCAGTTATGATATCAACTGGGTGCGACAGGCCACTGGACAAGG
GCTTGAGTGGATGGGATGGATGGACCCTAACAGTGGTAACACAGGCTATGCACAGAAGTTCCAGGG
CAGAGTCACCATGACCAGGAACACCTCCATAAGCACAGCCTACATGGAGCTGAGCAGCCTGAGATC
TGAGGACACGGCCGTGTATTACTGTGCGAGA888888GGCCACTATGATAGTGATGGTTATTACTCCTTCTCC
GGTATGGACGTCTGGGGCCAAGGGACCACGGTCACCGTCTCCTCA SEQ ID NO 84: Recombinant 5.948.1 - Predicted Heavy-Chain Variable-Domain amino-acid
sequence QVQLVQSGAEVKKPGASVKVSCKASGYTFTSYDINWVRQATGQGLEWMGWMDPNSGNTGYAQKFQG
RVTMTRNTSISTAYMELSSLRSEDTAVYYCARGHYDSDGYYSFSGMDVWGQGTTVTVSS SEQ ID NO 85: Recombinant 5.948.1 - Heavy-Chain CDR1 Nucleotide sequence

AGTTATGATATCAAC

SEQ ID NO 86: Recombinant 5.948.1 - Predicted Heavy-Chain CDR1 amino-acid sequence

SYDIN

SEQ ID NO 87: Recombinant 5.948.1 - Heavy-Chain CDR2 Nucleotide sequence

TGGATGGACCCTAACAGTGGTAACACAGGCTATGCACAGAAGTTCCAGGGC

SEQ ID NO 88: Recombinant 5.948.1 - Predicted Heavy-Chain CDR2 amino-acid sequence

WMDPNSGNTGYAQKFQG

SEQ ID NO 89: Recombinant 5.948.1 - Heavy-Chain CDR3 Nucleotide sequence

GGCCACTATGATAGTGATGGTTATTACTCCTTCTCCGGTATGGACGTC

SEQ ID NO 90: Recombinant 5.948.1 - Predicted Heavy-Chain CDR3 amino-acid sequence

GHYDSDGYYSFSGMDV

SEQ ID NO 91: Recombinant 5.948.1 - Full-length Light-Chain Nucleotide sequence

GATATTGTGATGACTCAGTCTCCACTCTCCCTGCCCGTCACCCCTGGAGAGCCGGCCTCCATCTCCT
GTAGGTCTAGTCAGAGCCTCCTGCATAGGAATGGATACAACTACTTGGATTGGTACCTGCAGAAGCC
AGGGCAGTCTCCACAGCTCCTGATCTATTTGGGTTCTAATCGGGCCTCCGGGGTCCCTGACAGGTT
CAGTGGCAGTGGATCAGGCACAGATTTTACACTGAAAATCAGCAGAGTGGAGGCTGAGGATGTTGG
GGTTTATTACTGCATGCAAGCTCTACAAACTCCTCCGGCCACTTTCGGCGGAGGGACCAAGGTGGA
GATCAAAcgaactgtggctgcaccatctgtcttcatcttcccgccatctgatgagcagttgaaatctggaactgcctctgttgtgtgcctgctgaataa
cttctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatcagg
gcctgagctcgcccgtcacaaagagcttcaacaggggagagtgt SEQ ID NO 92: Recombinant 5.948.1 - Predicted Full-length Light-Chain amino-acid sequence DIVMTQSPLSLPVTPGEPASISCRSSQSLLHRNGYNYLDWYLQKPGQSPQLLIYLGSNRASGVPDRFSGS
GSGTDFTLKISRVEAEDVGVYYCMQALQTPPATFGGGTKVEIKrtvaapsvfifppsdeqlksgtasvvclInnfypreakv
qwkvdnalqsgnsqesvteqdskdstysIsstItIskadyekhkvyacevthqgIsspvtksfnrgec SEQ ID NO 93: Recombinant 5.948.1 - Light-Chain Variable-Domain Nucleotide sequence GATATTGTGATGACTCAGTCTCCACTCTCCCTGCCCGTCACCCCTGGAGAGCCGGCCTCCATCTCCT
GTAGGTCTAGTCAGAGCCTCCTGCATAGGAATGGATACAACTACTTGGATTGGTACCTGCAGAAGCC
AGGGCAGTCTCCACAGCTCCTGATCTATTTGGGTTCTAATCGGGCCTCCGGGGTCCCTGACAGGTT
CAGTGGCAGTGGATCAGGCACAGATTTTACACTGAAAATCAGCAGAGTGGAGGCTGAGGATGTTGG
GGTTTATTACTGCATGCAAGCTCTACAAACTCCTCCGGCCACTTTCGGCGGAGGGACCAAGGTGGA
GATCAAA SEQ ID NO 94: Recombinant 5.948.1 - Predicted Light-Chain Variable-Domain amino-acid sequence DIVMTQSPLSLPVTPGEPASISCRSSQSLLHRNGYNYLDWYLQKPGQSPQLLIYLGSNRASGVPDRFSGS
GSGTDFTLKISRVEAEDVGVYYCMQALQTPPATFGGGTKVEIK SEQ ID NO 95: Recombinant 5.948.1 - Light-Chain CDR1 Nucleotide sequence

AGGTCTAGTCAGAGCCTCCTGCATAGGAATGGATACAACTACTTGGAT

SEQ ID NO 96: Recombinant 5.948.1 - Predicted Light-Chain CDR1 amino-acid sequence

RSSQSLLHRNGYNYLD

SEQ ID NO 97: Recombinant 5.948.1 - Light-Chain CDR2 Nucleotide sequence

TTGGGTTCTAATCGGGCCTCC

SEQ ID NO 98: Recombinant 5.948.1 - Predicted Light-Chain CDR2 amino-acid sequence

LGSNRAS

SEQ ID NO 99: Recombinant 5.948.1 - Light-Chain CDR3 Nucleotide sequence

ATGCAAGCTCTACAAACTCCTCCGGCCACT

SEQ ID NO 100: Recombinant 5.948.1 - Predicted Light-Chain CDR3 amino-acid sequence

MQALQTPPAT

SEQ ID NO 101: 5.396.1 from hybridoma - Heavy-Chain Nucleotide sequence

CAGGTGCAGCTACAGCAGTGGGGCGCAGGACTGTTGAAGCCTTCGGAGACCCTGTCCCTCACCTG
CGCTGTCTATGGTGGGTCCTTCAGTGGTTACTACTGGAGCTGGATCCGCCAGCCCCAGGGAAGGG
GCTGGAGTGGATTGGGAAATCCATCATAGTGGAAGCACCAACTACAACCCGTCCCTCAAGAGTCG
AGTCACCATATCAGTAGACACGTCCAAGAACCAGTTCTCCCTGAAGCTGAGCTCTGTGACCGCCGC
GGACACGGCTGTGTATTACTGTGCGAGAG8888GACAACTGGAACGACTCTTTCTACTACTACTACGGTATG
GACGTCTGGGGCCAAGGGACCACGGTCACCGTCTCCTCAgcctccaccaagggcccatcggtcttccccctggcgccc -continued

```
tgctccaggagcacctccgagagcacagcggccctgggctgcctggtcaaggactacttccccgaaccggtgacggtgtcgtggaactcaggcg
ctctgaccagcggcgtgcacaccttcccagctgtcctacagtcctcaggactctactccctcagcagcgtggtgaccgtgccctccagcaacttcggc
acccagacctacacctgcaacgtagatcacaagcccagcaacaccaaggtggacaagacagttgagcgcaaatgttgtgtcgagtgcccaccgt
gcccagcaccacctgtggcaggaccgtcagtcttcctcttccccccaaaacccaaggacaccctcatgatctcccggacccctgaggtcacgtgcg
tggtggtggacgtgagccacgaagacccggaggtccagttcaactggtacgtggacggcgtggaggtgcataatgccaagacaaagccacggg
aggagcagttcaacagcacgttccgtgtggtcagcgtcctcaccgttgtgcaccaggactggctgaacggcaaggagtacaagtgcaaggtctcc
aacaaaggcctcccagcccccatcgagaaaaccatctccaaaaccaaagggcagccccgagaaccacaggtgtacaccctgcccccatcccg
ggaggagatgaccaagaaccaggtcagcctgacctgcctggtcaaaggcttctaccccagcgacatcgccgtggagtgggagagcaatgggca
gccggagaacaactacaagaccacacctcccatgctggactccgacggctccttcttcctctacagcaagctcaccgtggacaagagcaggtggc
agcaggggaacgtcttctcatgctccgtgatgcatgaggctctgcacaaccactacacgcagaagagcctctccctgtctccgggtaaa
```

SEQ ID NO 102: 5.396.1 from hybridoma - Predicted Heavy-Chain amino-acid sequence QVQLQQWGAGLLKPSETLSLTCAVYGGSF<u>SGYYWS</u>WIRQPPGKGLEWIG<u>EIHHSGSTNYNPSLKSR</u>VTI
SVDTSKNQFSLKLSSVTAADTAVYYCAR<u>DNWNDSFYYYYGMDV</u>WGQGTTVTVSSastkgpsvfplapcsrstse
staalgclvkdyfpepvtvswnsgaltsgvhtfpavlqssglyslssvvtvpssngtqtytcnvdhkpsntkvdktverkccvecppcpappvagps
vflfppkpkdtlmisrtpevtcvvvdvshedpevqfnwyvdgvevhnaktkpreeqfnstfrvvsvltvvhqdwlngkeykckvsnkglpapiektis
ktkgqprepqvytlppsreemtknqvsltclvkgfypsdiavewesngqpennykttppmldsdgsfflyskltvdksrwqqgnviscsvmhealh
nhytqkslslspgk SEQ ID NO 103: 5.396.1 from hybridoma - Light-Chain Nucleotide sequence

```
GACATCCAGATGACCCAGTCTCCATCATCACTGTCTGCATCTGTAGGAGACAGAGTCACCATCACAT
GT<u>CGGGCGAGTCAGGGCATTAGCAATCATTTAGCCT</u>GGTTTCAGCAGAAACCAGGGAAAGCCCCTA
AGTCCCTGATCTAT<u>GCTGCATCCAGTTTGCAAAGT</u>GGGGTCCCATCAAAGTTCAGCGGCAGTGATC
TGGGACAGATTTCACTCTCACCATCAGCAGCCTGCAGCCTGAAGATTTTGCAACTTATTACTGC<u>CAAC
AGTATAATAGGCACCCATTCACT</u>TTCGGCCCTGGGACCAAAGTGGATATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt
```

SEQ ID NO 104: 5.396.1 from hybridoma - Predicted Light-Chain amino-acid sequence DIQMTQSPSSLSASVGDRVTITC<u>RASQGISNHLAW</u>FQQKPGKAPKSLIY<u>AASSLQS</u>GVPSKFSGSGSGTD
FTLTISSLQPEDFATYYC<u>QQYNRHPFT</u>FGPGTKVDIKrtvaapsvfifppsdeqlksgtasvvcllnnfypreakvqwkvdnalq
sgnsqesvteqdskdstyslsstltlskadyekhkvyacevthqglsspvtksfnrgec SEQ ID NO 105: 6.605.1 from hybridoma - Heavy-Chain Nucleotide sequence

```
CAGGTTCACCTGGTGCAGTCTGGAGCTGAGGTGAAGATGCCTGGGGCCTCAGTGAAGGTCTCCTGC
AAGGCTTCTGGTTACACCTTTACC<u>AGCTATGGTATCAGC</u>TGGGTGCGACAGGCCCCTGGACAAGGG
CTTGAGTGGATGGGA<u>TGGATCAGCGCTTACAATGGTAACACAAACTATGCACAGAAGCTCCAGGGC</u>
AGAATCACCATGACCACAGACACATCCACGAGCACAGCCTACATGGACCTGAGGAGCCTGAGATCT
GACGACACGGCCGTGTATTACTGTGCGAGA<u>GATGGGGATTACTATGATCCTTTTGACTAC</u>TGGGGCC
AGGGGAACCCTGGTCACCGTCTCCTCAgcctccaccaagggcccatcggtcttccccctggcgccctgctccaggagcacctccg
agagcacagcggccctgggctgcctggtcaaggactacttccccgaaccggtgacggtgtcgtggaactcaggcgctctgaccagcggcgtgca
caccttcccagctgtcctacagtcctcaggactctactccctcagcagcgtggtgaccgtgccctccagcaacttcggcacccagacctacacctgc
aacgtagatcacaagcccagcaacaccaaggtggacaagacagttgagcgcaaatgttgtgtcgagtgcccaccgtgcccagcaccacctgtg
gcaggaccgtcagtcttcctcttccccccaaaacccaaggacaccctcatgatctcccggacccctgaggtcacgtgcgtggtggtggacgtgagc
cacgaagaccccgaggtccagttcaactggtacgtggacggcgtggaggtgcataatgccaagacaaagccacgggaggagcagttcaacag
cacgttccgtgtggtcagcgtcctcaccgttgtgcaccaggactggctgaacggcaaggagtacaagtgcaaggtctccaacaaaggcctcccag
cccccatcgagaaaaccatctccaaaaccaaagggcagccccgagaaccacaggtgtacaccctgcccccatcccgggaggagatgaccaa
gaaccaggtcagcctgacctgcctggtcaaaggcttctaccccagcgacatcgccgtggagtgggagagcaatgggcagccggagaacaacta
caagaccacacctcccatgctggactccgacggctccttcttcctctacagcaagctcaccgtggacaagagcaggtggcagcaggggaacgtct
tctcatgctccgtgatgcatgaggctctgcacaaccactacacgcagaagagcctctccctgtctccgggtaaa
```

SEQ ID NO 106: 6.605.1 from hybridoma - Predicted Heavy-Chain amino-acid sequence QVHLVQSGAEVKMPGASVKVSCKASGYTFT<u>SYGIS</u>WVRQAPGQGLEWMG<u>WISAYNGNTNYAQKLQGR</u>
ITMTTDTSTSTAYMDLRSLRSDDTAVYYCAR<u>DGDYYDPFDY</u>WGQGTLVTVSSastkgpsvfplapcsrstsestaal
gclvkdyfpepvtvswnsgaltsgvhtfpavlqssglyslssvvtvpssnfgtqtytcnvdhkpsntkvdktverkccvecppcpappvagpsvflfp
pkpkdtlmisrtpevtcvvvdvshedpevqfnwyvdgvevhnaktkpreeqfnstfrvvsvltvvhqdwlngkeykckvsnkglpapiektisktkg
qprepqvytlppsreemtknqvsltclvkgfypsdiavewesngqpennykttppmldsdgsfflyskltvdksrwqqgnvfscsvmhealhnhyt
qkslslspgk SEQ ID NO 107: 6.605.1 from hybridoma - Light-Chain Nucleotide sequence

```
GACATCCAGATGACCCAGTCTCCATCCTCCCTGTCTGCATCTGTAGGAGACAGAGTCACCATCACTT
G<u>CCGGACAAGTCAGAGTATTAGCAACTGGTTAAAT</u>TGGTATCAGCAGAAACCAGGGAAAGCCCCTAA
ACTCCTGATCTAT<u>GGTGCCTCCACTTTGAAAAGT</u>GGGGTCCCATCAAGGTTCAGTGGCAGTGAATCT
GGGACAGATTTCACTCTCACCATCAGCAGTCTGCAACCTGAAGATTTTGCAACTTACTACTGT<u>CAACA
GAGTTACAGTACCCCTCCGACGTT</u>CGGCCAAGGGACCAAGGTGGAAATCAAAcgaactgtggctgcaccatct
gtcttcatcttcccgccatctgatgagcagttgaaatctggaactgcctctgttgtgtgcctgctgaataacttctatcccagagaggccaaagtacagtg
gaaggtggataacgccctccaatcgggtaactcccaggagagtgtcacagagcaggacagcaaggacagcacctacagcctcagcagcaccc
tgacgctgagcaaagcagactacgagaaacacaaagtctacgcctgcgaagtcacccatcagggcctgagctcgcccgtcacaaagagcttca
acaggggagagtgt
```

-continued

SEQ ID NO 108: 6.605.1 from hybridoma - Predicted Light-Chain amino-acid sequence DIQMTQSPSSLSASVGDRVTITC<u>RTSQSISNWLN</u>WYQQKPGKAPKLLIY<u>GASTLKS</u>GVPSRFSGSESGTD
FTLTISSLQPEDFATYYC<u>QQSYSTPPT</u>FGQGTKVEIKrtvaapsvfifppsdeqlksgtasvvcllnnfypreakvqwkvdnalq
sgnsqesvteqdskdstyslsstltlskadyekhkvyacevthqglsspvtksfnrgec SEQ ID NO 109: 5.948.1 from hybridoma - Heavy-Chain Nucleotide sequence CAGGTGCAGCTGGTGCAGTCTGGGGCTGAGGTGAAGAAGCCTGGGGCCTCAGTGAAGGTCTCCTG
CAAGGCTTCTGGATACACCTTCACC<u>AGTTATGATATCAACT</u>GGGTGCGACAGGCCACTGGACAAGG
GCTTGAGTGGATGGGA<u>TGGATGGACCCTAACAGTGGTAACACAGGCTATGCACAGAAGTTCCAGGG
C</u>AGAGTCACCATGACCAGGAACACCTCCATAAGCACAGCCTACATGGAGCTGAGCAGCCTGAGATC
TGAGGACACGGCCGTGTATTACTGTGCGAGA<u>7777777GGCTACTATGATAGTGATGGTTATTACTCCTTCTCC
GGTATGGACGTC</u>TGGGGCCAAGGGACCACGGTCACCGTCTCCTCAgcctccaccaagggcccatcggtcttccc
ctggcgccctgctccaggagcacctccgagagcacagcggccctgggctgcctggtcaaggactacttccccgaaccggtgacggtgtcgtgga
actcaggcgctctgaccagcggcgtgcacaccttcccggctgtcctacagtcctcaggactctactccctcagcagcgtggtgaccgtgccctccag
caacttcggcacccagacctacacctgcaacgtagatcacaagcccagcaacaccaaggtggacaagacagttgagcgcaaatgttgtgtcga
gtgcccaccgtgcccagcaccacctgtggcaggaccgtcagtcttcctcttccccccaaaacccaaggacaccctcatgatctcccggacccctga
ggtcacgtgcgtggtggtggacgtgagccacgaagaccccgaggtccagttcaactggtacgtggacggcgtggaggtgcataatgccaagaca
aagccacgggaggagcagttcaacagcacgttccgtgtggtcagcgtcctcaccgttgtgcaccaggactggctgaacggcaaggagtacaagt
gcaaggtctccaacaaaggcctcccagcccccatcgagaaaaccatctccaaaaccaaagggcagccccgagaaccacaggtgtacaccctg
cccccatcccgggaggagatgaccaagaaccaggtcagcctgacctgcctggtcaaaggcttctaccccagcgacatcgccgtggagtgggag
agcaatgggcagccggagaacaactacaagaccacacctcccatgctggactccgacggctccttcttcctctacagcaagctcaccgtggacaa
gagcaggtggcagcaggggaacgtcttctcatgctccgtgatgcatgaggctctgcacaaccactacacgcagaagagcctctccctgtctccggg
taaa SEQ ID NO 110: 5.948.1 from hybridoma - Predicted Heavy-Chain amino-acid sequence QVQLVQSGAEVKKPGASVKVSCKASGYTFT<u>SYDIN</u>WVRQATGQGLEWMG<u>WMDPNSGNTGYAQKFQG</u>
RVTMTRNTSISTAYMELSSLRSEDTAVYYCAR<u>GHYDSDGYYSFSGMDV</u>WGQGTTVTVSSastkgpsvfplap
csrstsestaalgclvkdyfpepvtvswnsgaltsgvhtfpavlqssglyslssvvtvpssnfgtqtytcnvdhkpsntkvdktverkccvecppcpap
pvagpsvflfppkpkdtlmisrtpevtcvvvdvshedpevqfnwyvdgvevhnakttkpreeqfnstfrvvsvltvvhqdwlngkeykckvsnklp
apiektisktkgqprepqvytlppsreemtknqvsltclvkgfypsdiavewesngqpennykttppmldsdgsfflysktltvdksrwqqgnvfscsv
mhealhnhytqkslslspgk SEQ ID NO 111: 5.948.1 from hybridoma - Light-Chain Nucleotide sequence GATATTGTGATGACTCAGTCTCCACTCTCCCTGCCCGTCACCCCTGGAGAGCCGGCCTCCATCTCCT
GT<u>AGGTCTAGTCAGAGCCTCCTGCATAGGAATGGATACAACTACTTGGAT</u>TGGTACCTGCAGAAGCC
AGGGCAGTCTCCACAGCTCCTGATCTATTT<u>GGGTTCTAATCGGGCCTC</u>CGGGGTCCCTGACAGGTT
CAGTGGCAGTGGATCAGGCACAGATTTTACACTGAAAATCAGCAGAGTGGAGGCTGAGGATGTTGG
GGTTTATTACTGC<u>ATGCAAGCTCTACAAACTCCTCCGGCCACTTTC</u>GGCGGAGGGACCAAGGTGGA
GATCAAAcgaactgtggctgcaccatctgtcttcatcttcccgccatctgatgagcagttgaaatctggaactgcctctgttgtgtgcctgctgaataa
cttctatcccagagaggccaaagtacagtggaaggtggataacgcctccaatcgggtaactcccaggagagtgtcacagagcaggacagcaa
ggacagcacctacagcctcagcagcacctgacgctgagcaaagcagactacgagaaacacaaagtctacgcctgcgaagtcacccatcagg
gcctgagctcgcccgtcacaaagagcttcaacaggggagagtgt SEQ ID NO 112: 5.948.1 from hybridoma - Predicted Light-Chain amino-acid sequence DIVMTQSPLSLPVTPGEPASISC<u>RSSQSLLHRNGYNYLD</u>WYLQKPGQSPQLLIY<u>LGSNRAS</u>GVPDRFSGS
GSGTDFTLKISRVEAEDVGVYYC<u>MQALQTPPAT</u>FGGGTKVEIKrtvaapsvfifppsdeqlksgtasvvcllnnfypreakv
qwkvdnalqsgnsqesvteqdskdstyslsstltlskadyekhkvyacevthqglsspvtksfnrgec SEQ ID NO 121: Recombinant 5.948.1(H100Y)- Full-length Heavy-Chain Nucleotide sequence CAGGTGCAGCTGGTGCAGTCTGGGGCTGAGGTGAAGAAGCCTGGGGCCTCAGTGAAGGTCTCCTG
CAAGGCTTCTGGATACACCTTCACC<u>AGTTATGATATCAACT</u>GGGTGCGACAGGCCACTGGACAAGG
GCTTGAGTGGATGGGA<u>TGGATGGACCCTAACAGTGGTAACACAGGCTATGCACAGAAGTTCCAGGG
C</u>AGAGTCACCATGACCAGGAACACCTCCATAAGCACAGCCTACATGGAGCTGAGCAGCCTGAGATC
TGAGGACACGGCCGTGTATTACTGTGCGAGA<u>7777777GGCTACTATGATAGTGATGGTTATTACTCCTTCTCC
GGTATGGACGTC</u>TGGGGCCAAGGGACCACGGTCACCGTCTCCTCAgcctccaccaagggcccatcggtcttccc
ctggcgccctgctccaggagcacctccgagagcacagcggccctgggctgcctggtcaaggactacttccccgaaccggtgacggtgtcgtgga
actcaggcgctctgaccagcggcgtgcacaccttcccggctgtcctacagtcctcaggactctactccctcagcagcgtagtgaccgtgccctccag
caacttcggcacccagacctacacctgcaacgtagatcacaagcccagcaacaccaaggtggacaagacagttgagcgcaaatgttgtgtcga
gtgcccaccgtgcccagcaccacctgtggcaggaccgtcagtcttcctcttccccccaaaacccaaggacaccctcatgatctccc
<u>Ggaccctgaggtcacgtgcgtggtggtggacgtgagccacgaagaccccgaggtccagttcaactggtacgtggacggcgtggaggtgcataa
tgccaagacaaagccacgggaggagcagttcaacagcacgttccgtgtggtcagcgtcctcaccgtcgtgcaccaggactggctgaacggcaa
ggagtacaagtgcaaggtctccaacaaaggcctcccagcccccatcgagaaaaccatctccaaaaccaaagggcagccccgagaaccacag
gtgtacaccctgcccccatcccgggaggagatgaccaagaaccaggtcagcctgacctgcctggtcaaaggcttctaccccagcgacatcgccgt
ggagtgggagagcaatgggcagccggagaacaactacaagaccacacctcccatgctggactccgacggctccttcttcctctacagcaagctc
accgtggacaagagcaggtggcagcaggggaacgtcttctcatgctccgtgatgcatgaggctctgcacaaccactacacacagaagagcctct
ccctgtctccgggtaaa</u>

SEQ ID NO 122: Recombinant 5.948.1 (H100Y) - Predicted Full-length Heavy-Chain amino-acid
sequence QVQLVQSGAEVKKPGASVKVSCKASGYTFT<u>SYDIN</u>WVRQATGQGLEWMG<u>WMDPNSGNTGYAQKFQG</u>
RVTMTRNTSISTAYMELSSLRSEDTAVYYCAR<u>GYDSDGYYSFSGMDV</u>WGQGTTVTVSSastkgpsvfplap csrstsestaalgclvkdyfpepvtvswnsgaltsgvhtfpavlqssglyslssvvtvpssnfgtqtytcnvdhkpsntkvdktverkccvecppcpap
pvagpsvflfppkpkdtlmisrtpevtcvvvdvshedpevqfnwyvdgvevhnaktkpreeqfnstfrvvsvltvvhqdwlngkeykckvsnkglp
apiektisktkgqprepqvytlppsreemtknqvsltclvkgfypsdiavewesngqpennykttppmldsdgsfflyskltvdksrwqqgnvfscsv
mhealhnhytqkslslspgk SEQ ID NO 123: Recombinant 5.948.1 (H100Y)- Heavy-Chain Variable-Domain Nucleotide sequence CAGGTGCAGCTGGTGCAGTCTGGGGCTGAGGTGAAGAAGCCTGGGGCCTCAGTAAGGTCTCCTG
CAAGGCTTCTGGATACACCTTCACC<u>AGTTATGATATCAAC</u>TGGGTGCGACAGGCCACTGGACAAGG
GCTTGAGTGGATGGA<u>ATGGATGGACCCTAACAGTGGTAACACAGGCTATGCACAGAAGTTCCAGGG</u>
<u>C</u>AGAGTCACCATGACCAGGAACACCTCCATAAGCACAGCCTACATGGAGCTGAGCAGCCTGAGATC
TGAGGACACGGCCGTGTATTACTGTGCGAGA<u>???????????GGCTACTATGATAGTGATGGTTATTACTCCTTCTCC</u>
<u>GGTATGGACGTC</u>TGGGGCCAAGGGACCACGGTCACCGTCTCCTCA SEQ ID NO 124: Recombinant 5.948.1 (H100Y) - Predicted Heavy-Chain Variable-Domain amino-acid sequence QVQLVQSGAEVKKPGASVKVSCKASGYTFT<u>SYDIN</u>WVRQATGQGLEWMG<u>WMDPNSGNTGYAQKFQG</u>
RVTMTRNTSISTAYMELSSLRSEDTAVYYCAR<u>GYYDSDGYYSFSGMDV</u>WGQGTTVTVSS SEQ ID NO 125: Recombinant 5.948.1 (H100Y) - Heavy-Chain CDR1 Nucleotide sequence <u>AGTTATGATATCAAC</u>

SEQ ID NO 126: Recombinant 5.948.1 (H100Y) - Predicted Heavy-Chain CDR1 amino-acid sequence <u>SYDIN</u>

SEQ ID NO 127: Recombinant 5.948.1 (H100Y) - Heavy-Chain CDR2 Nucleotide sequence <u>TGGATGGACCCTAACAGTGGTAACACAGGCTATGCACAGAAGTTCCAGGGC</u>

SEQ ID NO 128: Recombinant 5.948.1 (H100Y) - Predicted Heavy-Chain CDR2 amino-acid sequence <u>WMDPNSGNTGYAQKFQG</u>

SEQ ID NO 129: Recombinant 5.948.1 (H100Y) - Heavy-Chain CDR3 Nucleotide sequence <u>GGCTACTATGATAGTGATGGTTATTACTCCTTCTCCGGTATGGACGTC</u>

SEQ ID NO 130: Recombinant 5.948.1 (H100Y) - Predicted Heavy-Chain CDR3 amino-acid sequence <u>GYYDSDGYYSFSGMDV</u>

SEQ ID NO 131: Recombinant 5.948.1 (H100Y) - Full-length Light-Chain Nucleotide sequence GATATTGTGATGACTCAGTCTCCACTCTCCCTGCCCGTCACCCCTGGAGAGCCGGCCTCCATCTCCT
GT<u>AGGTCTAGTCAGAGCCTCCTGCATAGGAATGGATACAACTACTTGGATT</u>GGTACCTGCAGAAGCC
AGGGCAGTCTCCACAGCTCCTGATCTAT<u>TTGGGTTCTAATCGGGCCTCC</u>GGGGTCCCTGACAGGTT
CAGTGGCAGTGGATCAGGCACAGATTTTACACTGAAAATCAGCAGAGTGGAGGCTGAGGATGTTGG
GGTTTATTACTGC<u>ATGCAAGCTCTACAAACTCCTCCGGCCAC</u>TTTCGGCGGAGGGACCAAGGTGGA
GATCAAAcgaactgtggctgcaccatctgtcttcatcttcccgccatctgatgagcagttgaaatctggaactgcctctgttgtgtgcctgctgaataa
cttctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatcagg
gcctgagctcgcccgtcacaaagagcttcaacaggggagagtgt SEQ ID NO 132: Recombinant 5.948.1 (H100Y) - Predicted Full-length Light-Chain amino-acid sequence DIVMTQSPLSLPVTPGEPASISCR<u>SSQSLLHRNGYNYLD</u>WYLQKPGQSPQLLIY<u>LGSNRAS</u>GVPDRFSGS
GSGTDFTLKISRVEAEDVGVYYC<u>MQALQTPPAT</u>FGGGTKVEIKrtvaapsvfifppsdeqlksgtasvvcllnnfypreakv
qwkvdnalqsgnsqesvteqdskdstyslsstltlskadyekhkvyacevthqglsspvtksfnrgec SEQ ID NO 133: Recombinant 5.948.1 (H100Y) - Light-Chain Variable-Domain Nucleotide sequence GATATTGTGATGACTCAGTCTCCACTCTCCCTGCCCGTCACCCCTGGAGAGCCGGCCTCCATCTCCT
GT<u>AGGTCTAGTCAGAGCCTCCTGCATAGGAATGGATACAACTACTTGGATT</u>GGTACCTGCAGAAGCC
AGGGCAGTCTCCACAGCTCCTGATCTAT<u>TTGGGTTCTAATCGGGCCTCC</u>GGGGTCCCTGACAGGTT
CAGTGGCAGTGGATCAGGCACAGATTTTACACTGAAAATCAGCAGAGTGGAGGCTGAGGATGTTGG
GGTTTATTACTGC<u>ATGCAAGCTCTACAAACTCCTCCGGCCAC</u>TTTCGGCGGAGGGACCAAGGTGGA
GATCAAA -continued SEQ ID NO 134: Recombinant 5.948.1 (H100Y) - Predicted Light-Chain Variable-Domain amino-acid sequence DIVMTQSPLSLPVTPGEPASISCRSSQSLLHRNGYNYLDWYLQKPGQSPQLLIYLGSNRASGVPDRFSGS
GSGTDFTLKISRVEAEDVGVYYCMQALQTPPATFGGGTKVEIK SEQ ID NO 135: Recombinant 5.948.1 (H100Y) - Light-Chain CDR1 Nucleotide sequence

AGGTCTAGTCAGAGCCTCCTGCATAGGAATGGATACAACTACTTGGAT

SEQ ID NO 136: Recombinant 5.948.1 (H100Y) - Predicted Light-Chain CDR1 amino-acid sequence

RSSQSLLHRNGYNYLD

SEQ ID NO 137: Recombinant 5.948.1 (H100Y) - Light-Chain CDR2 Nucleotide sequence

TTGGGTTCTAATCGGGCCTCC

SEQ ID NO 138: Recombinant 5.948.1 (H100Y) - Predicted Light-Chain CDR2 amino-acid sequence

LGSNRAS

SEQ ID NO 139: Recombinant 5.948.1 (H100Y) - Light-Chain CDR3 Nucleotide sequence

ATGCAAGCTCTACAAACTCCTCCGGCCACT

SEQ ID NO 140: Recombinant 5.948.1 (H100Y) - Predicted Light-Chain CDR3 amino-acid sequence

MQALQTPPAT

The invention claimed is:

1. An isolated monoclonal antibody directed against human IgE or an antigen-binding portion of said antibody, said antibody comprising a set of H-CDRs (H-CDR1, H-CDR2, and H-CDR3) respectively having the sequences of SEQ ID NOs: 126, 128, and 130; and a set of L-CDRs (L-CDR1, L-CDR2, and L-CDR3) respectively having the sequences of SEQ ID NOs: 136, 138, and 140.

2. An isolated monoclonal antibody directed against human IgE or an antigen-binding portion of said antibody, said antibody comprising a set of H-CDRs (H-CDR1, H-CDR2, and H-CDR3) from the heavy chain of antibody 5.948.1 H100Y, and a set of L-CDRs (L-CDR1, L-CDR2, and L-CDR3) from the light chain of antibody 5.948.1H100Y.

3. An isolated monoclonal antibody directed against human IgE or an antigen-binding portion of said antibody, said antibody comprising a heavy chain comprising the amino acid sequence of SEQ ID NO: 124, and a light chain comprising the amino acid sequence of SEQ ID NO: 134.

4. A human monoclonal antibody directed against human IgE or an antigen-binding portion of said antibody, said antibody comprising a heavy chain comprising the amino acid sequence of SEQ ID NO: 122, and a light chain comprising the amino acid sequence of SEQ ID NO: 132.

5. A human monoclonal antibody consisting of a heavy chain whose amino acid sequence is SEQ ID NO: 122 and a light chain whose amino acid sequence is SEQ ID NO: 132.

6. A pharmaceutical composition comprising an antibody according to claim 5.

7. The antibody according to claim 1, wherein said antibody is of the IgG1 or IgG2 subtype.

8. An isolated antibody comprising the heavy chain and light chain amino acid sequences of antibody 5.948.1 H100Y.

9. An isolated antibody comprising the heavy chain variable domain and light chain variable domain amino acid sequences of antibody 5.948.1 H100Y, or an antigen-binding portion of said isolated antibody.

10. An isolated monoclonal antibody directed against human IgE or an antigen-binding portion of said antibody, said antibody comprising a heavy chain comprising the amino acid sequence of SEQ ID NO: 124.

11. An isolated monoclonal antibody directed against human IgE or an antigen-binding portion of said antibody, said antibody comprising a light chain comprising the amino acid sequence of SEQ ID NO: 134.

12. A method for treating an IgE-mediated disorder selected from the group consisting of asthma, allergic asthma, allergic rhinitis and food allergies in a subject in need thereof, comprising administering to said subject a therapeutically effective amount of an antibody or portion thereof according to claim 1.

13. A method for reducing IgE binding to FcεR1 comprising contacting the IgE with an anti-IgE antibody or antigen-binding portion according to claim 1.

14. A method for reducing IgE-mediated degranulation by a cell comprising contacting the cell with an anti-IgE antibody or antigen-binding portion according to claim 1.

* * * * *